(12) United States Patent
Hung et al.

(10) Patent No.: US 9,885,088 B2
(45) Date of Patent: Feb. 6, 2018

(54) RAPID PHENOTYPIC DIAGNOSIS OF PATHOGENS AND DRUG RESISTANCE USING TRANSCRIPTIONAL EXPRESSION SIGNATURES

(75) Inventors: Deborah Hung, Lexington, MA (US); James Gomez, Jamaica Plain, MA (US); Amy Barczak, Medford, MA (US)

(73) Assignees: The Broad Institute, Inc., Cambridge, MA (US); The General Hospital Corporation, Boston, MA (US); The Brigham and Women's Hospital, Inc., Boston, MA (US)

( * ) Notice: Subject to any disclaimer, the term of this patent is extended or adjusted under 35 U.S.C. 154(b) by 98 days.

(21) Appl. No.: 13/580,618

(22) PCT Filed: Feb. 24, 2011

(86) PCT No.: PCT/US2011/026092
§ 371 (c)(1),
(2), (4) Date: Apr. 8, 2013

(87) PCT Pub. No.: WO2011/106536
PCT Pub. Date: Sep. 1, 2011

(65) Prior Publication Data
US 2013/0190196 A1 Jul. 25, 2013

Related U.S. Application Data

(60) Provisional application No. 61/307,669, filed on Feb. 24, 2010, provisional application No. 61/323,252, filed on Apr. 12, 2010.

(51) Int. Cl.
*C12Q 1/68* (2006.01)
*C12Q 1/70* (2006.01)
*C12Q 1/02* (2006.01)

(52) U.S. Cl.
CPC ............ *C12Q 1/689* (2013.01); *C12Q 1/025* (2013.01); *C12Q 1/6809* (2013.01); *C12Q 1/6888* (2013.01); *C12Q 1/6895* (2013.01); *C12Q 1/70* (2013.01); *C12Q 2600/112* (2013.01); *C12Q 2600/158* (2013.01); *G01N 2333/35* (2013.01); *G01N 2800/52* (2013.01); *G01N 2800/56* (2013.01)

(58) Field of Classification Search
None
See application file for complete search history.

(56) References Cited

U.S. PATENT DOCUMENTS

2008/0113342 A1 * 5/2008 Cao et al. .................. 435/6

FOREIGN PATENT DOCUMENTS

| JP | 07-506482 | 7/1995 |
|---|---|---|
| JP | H09-509663 | 9/1997 |
| JP | 2001-103981 | 4/2001 |
| JP | 2009-017836 | 7/2007 |
| KR | 10-2003-0030266 | 4/2003 |
| WO | 1993/15221 | 8/1993 |
| WO | WO 95/23160 | 8/1995 |
| WO | WO2001021839 | * 3/2001 |
| WO | 2001/36683 | 5/2001 |
| WO | 2002/077183 | 10/2002 |
| WO | WO2005/017193 | 2/2005 |
| WO | WO2008/124847 | 10/2008 |
| WO | 2009/054957 | 4/2009 |
| WO | WO2009/054957 | 4/2009 |

OTHER PUBLICATIONS

Wilson et al. Proceedings of the National Academy of Sciences 96.22 (1999): 12833-12838.*
Arnold et al. Clin Microbiol Infect 2005; 11: 122-130.*
Blast analysis(SEQID 115 and SEQID116).*
Geiss et al. Nature biotechnology 26.3 (2008): 317-325.*
Wilson et al. Proceedings of the National Academy of Sciences 96.22(1999): 12833-12838.*
Malkov et al. BMC Research Notes 2009, 2:80; 9 pages.*
Arnold et al. Clin Microbiol Infect 2005;11:122-130.*
Lowe et al. Nucleic Acids Research, vol. 18, No. 7, p. 1757-1761,1990.*
Blast analysis.*
Goldman et al., "Discovery and Validation of New Antitubercular Compounds as Potential Drug Leads and Probes," Tuberculosis (Edinb) 89:331-333, 2009.
International Search Report and Written Opinion; Application No. PCT/US2011/026092; dated Jan. 2, 2012; 15 pages.
Mdivani et al., "Monitoring Therapeutic Efficacy by Real-Time Detection of *Mycobacterium tuberculosis* MRNA in Sputum," Clin. Chem. 55:1694-1700, 2009.
NCBI Reference Sequence: NC_000913.1. Oct. 15, 2001; 778 pages.
Raman et al., "Target TB: A Target Identification Pipeline for *Mycobacterium tuberculosis* Through an Interactome, Reactome, and Genome-Scale Structural Analysis," BMC Syst. Biol. 2:109-129, 2008.
Waddell et al., "The Use of Microarray Analysis to Determine the Gene Expression Profiles of *Mycobacterium tuberculosis* in Response to Anti-Bacterial Compounds," Tuberculosis (Edinb) 84:263-274, 2004.
Brem, "The landscape of genetic complexity across 5,700 gene expression traits in yeast," Proc Natl Acad Sci USA 102(5):1572-1577 (2005).
Chinese Office Action issued in CN201180020693.5 dated Oct. 8, 2013 (with translation—19 pages).
European Search Report issued in EP11748072.3 dated Aug. 23, 2013 (9 pages).

(Continued)

*Primary Examiner* — Antonio Galisteo Gonzalez
(74) *Attorney, Agent, or Firm* — Fish & Richardson P.C.

(57) ABSTRACT

The specification relates generally to methods of detecting, diagnosing, and/or identifying pathogens, e.g., infectious disease pathogens and determining their drug sensitivity and appropriate methods of treatment. This invention also relates generally to methods of monitoring pathogen infection in individual subjects as well as larger populations of subjects.

19 Claims, 30 Drawing Sheets

(56) References Cited

OTHER PUBLICATIONS

Perlstein et al., "Genetic basis of individual differences in the response to small-molecule drugs in yeast," Nature Genetics, 39(4):496-502 (2007).
Ruderfer et al., "Using Expression and Genotype to Predict Drug Response in Yeast," PLOS One, 4(9):e6907 (2009).
Zeng, "Genome-wide expression profiling of the response to terbinafine in Candida albicans using a cDNA microarray analysis," Chinese Medical Journal, 120(9):807-813 (2007).
Boshoff et al., "The Transcriptional Responses of *Mycobacterium tuberculosis* to Inhibitors of Metabolism," The Journal of Biological Chemistry, 279(38):40174-40184 (2004).
Communication issued in EP11748072.3 dated Dec. 11, 2014 (5 pages).
European Search Report issued in EP14181061 dated Nov. 25, 2014 (9 pages).
Fenhalls et al., "Localisation of mycobacterial DNA and mRNA in human tuberculous granulomas," Journal of Microbiological Methods, 51:197-208 (Apr. 2002).
Office Action issued in AU2011220736 dated Mar. 13, 2014 (5 pages).
Office Action issued in CN201180020693.5 dated Apr. 11, 2014 with English Translation (14 pages).
Office Action issued in CN201180020693.5 dated Nov. 4, 2014 with English Translation (11 pages).
Final Rejection issued in CN201180020693.5 dated Jan. 18, 2016 with English translation (15 pages).
Office Action issued in AU2014210639 dated Feb. 24, 2010 (4 pages).
Office Action issued in CN201180020693.5 dated May 20, 2015 with English translation (14 pages).
Office Action issued in CN201410415201.8 dated Aug. 5, 2015 with English Translation (20 pages).
Office Action issued in EP14181061.4 dated Oct. 2, 2015 (5 pages).
Office Action issued in JP2012-555149 dated Apr. 21, 2015 with English Translation, 12 pages.
Office Action issued in JP2012-555149 dated Feb. 1, 2016 with English Translation (6 pages).
Office Action issued in RU2012140430 dated Jun. 1, 2015 with English Translation (7 pages).
Rincones et al., Molecular Plant-Microbe Interactions, 21(7):891-908 (2008).
Stabler et al., "Development and application of the active surveillance of pathogens microarray to monitor bacterial gene flux," BMC Microbiology, 8(1):177 (2008).
Strommenger et al., "DNA microarray for the detection of therapeutically relevant antibiotic resistance determinant sin clinical isolates of *Staphylococcus aureus*," Molecular and Cellular Probes, 21(3):161-170 (2007).
Waddell et al., "The use of microarray analysis to determine the gene expression profiles of *Mycobacterium tuberculosis* in response to anti-bacterial compounds," Tuberculosis, 84(3-4):263-274 (2004).
European Office Action in European Application No. 14181061, dated Sep. 20, 2016, 4 pages.
Japanese Office Action in Japanese Application No. 2012-555149, dated Oct. 18, 2016, 6 pages (with English translation).
Canadian Office Action in Canadian Application No. 2,791,228, dated Nov. 17, 2016, 4 pages.
Clancy Suzanne & William Brown, Translation: DNA to mRNA to Protein, Nature Education, 2008, 1(1):101, 7 pages, found from the Internet on May 19, 2016; <URL: http://www.nature.com/scitable/topicpage/translation-dna-to-mrna-to-protein-393>).
Office Action issued in JP2015-207253 dated Aug. 19, 2016 with English Translation (8 pages).
Office Action issued in AU2014210639 dated Sep. 2, 2016 (3 pages).
Office Action issued in RU2012140430 dated Aug. 31, 2016 with English Translation (9 pages).
Lullmann et al., Illustrative Pharmacology, Moscow, 2008, 383 pages, see p. 290 (with English Summary).
Office Action in Russian Application No. 2012140430, dated Jan. 20, 2017, 8 pages (with English translation).
Song et al., "Detection of oligonucleotide hybridization at femtomolar level and sequence-specific gene analysis of the *Arabidopsis thaliana* leaf extract with an ultrasensitive surface plasmon resonance spectrometer," Nucleic Acids Res, Jul. 2002, 30(14): e72, 11 pages.
Office Action in Korean Application No. 10-2012-7024419, dated Oct. 30, 2017, 13 pages (with English translation).
Office Action in Canadian Application No. 2,791,228, dated Dec. 11, 2017, 3 pages.

* cited by examiner mecA expression in methicillin-sensitive vs. methicillin-resistant S. aureus vanA expression in vancomycin-sensitive vs. vancomycin-resistant enterococcus

RAPID PHENOTYPIC DIAGNOSIS OF PATHOGENS AND DRUG RESISTANCE USING TRANSCRIPTIONAL EXPRESSION SIGNATURES

CROSS REFERENCE TO RELATED APPLICATIONS

This application is the U.S. national stage under 35 USC § 371 of International Application Number PCT/US2011/026092, filed on Feb. 24, 2011 which claims priority to U.S. Application No. 61/307,669, filed on Feb. 24, 2010, and U.S. Application No. 61/323,252, filed on Apr. 12, 2010, the entire contents of which applications is hereby incorporated by reference.

FEDERALLY SPONSORED RESEARCH OR DEVELOPMENT

This invention was made with Government support under Grant Number AI057159 and Grant Number AI08002 awarded by the National Institutes of Health. The Government has certain rights in the invention.

TECHNICAL FIELD

The invention relates, inter alia, to methods of detecting, diagnosing, and/or identifying pathogens, e.g., infectious disease pathogens, and determining their sensitivity to known or potential treatments.

BACKGROUND

The development of molecular diagnostics has revolutionized care in most medical disciplines except infectious disease, where they have failed to play a widespread, transforming role. The reliance on slow culture methods is particularly frustrating in the current crisis of antibiotic resistance as the development of molecular tools to rapidly diagnose the inciting pathogen and its drug resistance profile would transform the management of bacterial, fungal, viral, and parasitic infections, guiding rapid, informed drug treatment in an effort to decrease mortality, control health care costs, and improve public health control of escalating resistance among pathogens. In U.S. hospitals alone, 1.7 million people acquire nosocomial bacterial infection and 99,000 die every year, with 70% of these infections due to bacteria resistant to at least one drug and an estimated annual cost of $45 billion (Klevens et al., 2002. Public Health Rep. 2007; 122(2):160-6; Klevens et al., Clin Infect Dis. 2008; 47(7):927-30; Scott, The Direct Medical Costs of Healthcare-Associated Infection in U.S. Hospitals and the Benefits of Prevention. In: Division of Healthcare Quality Promotion NCfP, Detection and Control of Infectious Diseases, editor. Atlanta: CDC, 2009). However, the problem is not limited to the U.S. and microbial resistance now impacts the majority of common bacterial infections globally. Global spread of methicillin-resistant *S. aureus* (MRSA), multi-drug resistant tuberculosis (MDR-TB), and increasingly drug resistant Gram-negative organisms prompted the formulation of an action plan focusing on surveillance, prevention and control, research and product development (US action plan to combat antimicrobial resistance. Infect Control Hosp Epidemiol. 2001; 22(3):183-4). However, minimal progress has been made on any of these fronts.

Prompt administration of the appropriate antibiotic has repeatedly been shown to minimize mortality in patients with severe bacterial infections, whether within the hospital setting with nosocomial pathogens such as *E. faecium, S. aureus, K. pneumoniae, A. baumanii, P. aeruginosa*, and *Enterobacter* species, or in resource-poor settings with pathogens such as tuberculosis (TB) (Harbarth et al., Am J. Med. 2003; 115(7):529-35; Harries et al., Lancet. 2001; 357(9267):1519-23; Lawn et al., Int J Tuberc Lung Dis. 1997; 1(5):485-6). However, because current diagnostic methods involving culture and sub-culture of organisms can take several days or more to correctly identify both the organism and its drug susceptibility pattern, physicians have resorted to increasing use of empiric broad-spectrum antibiotics, adding to the selective pressure for resistance and increasing the associated health-care costs. A point of care diagnostic to rapidly (e.g., less than 1 hour) detect pathogens and their resistance profiles is urgently needed and could dramatically change the practice of medicine. Some effort into designing DNA- or PCR-based tests has resulted in tools that are able to identify pathogens rapidly with low detection limits. However, global use of these tools is currently limited due to cost and demand for laboratory infrastructure and to the inherent insensitivity of PCR-based methods in the setting of crude samples that are not easily amenable to the required enzymology. Molecular approaches to determining drug resistance have been even more limited, available for some organisms (e.g., MRSA, TB) in very limited ways, based on defining the genotype of the infecting bacteria relative to known resistance conferring mutations. This method however, requires fairly comprehensive identification of all resistance conferring single nucleotide polymorphisms (SNPs) for the test to have high sensitivity (Carroll et al., Mol Diagn Ther. 2008; 12(1):15-24).

SUMMARY

The present invention is based, at least in part, on the discovery of new methods of diagnosing disease, identifying pathogens, and optimizing treatment based on detection of mRNA, e.g., in crude, non-purified samples. The methods described herein provide rapid and accurate identification of pathogens in samples, e.g., clinical samples, and allow for the selection of optimal treatments based on drug sensitivity determinations.

In one aspect, the invention features methods of determining the drug sensitivity of a pathogen, e.g., a disease-causing organism such as a bacterium, fungus, virus, or parasite. The methods include providing a sample comprising a pathogen and contacting the sample with one or more test compounds, e.g., for less than four hours, to provide a test sample. The test sample can be treated under conditions that release mRNA from the pathogen into the test sample and the test sample is exposed to a plurality of nucleic acid probes, comprising a plurality of subsets of probes, wherein each subset comprises one or more probes that bind specifically to a target mRNA that is differentially expressed in organisms that are sensitive to a test compound as compared to organisms that are resistant, wherein the exposure occurs for a time and under conditions in which binding between the probe and target mRNA can occur. The method comprises determining a level of binding between the probe and target mRNA, thereby determining a level of the target mRNA; and comparing the level of the target mRNA in the presence of the test compound to a reference level, e.g., the level of the target mRNA in the absence of the test compound, wherein a difference in the level of target mRNA relative to the reference level of target mRNA indicates whether the pathogen is sensitive or resistant to the test compound.

In one embodiment, the pathogen is known, e.g., an identified pathogen. In some embodiments, the methods determine the drug sensitivity of an unknown pathogen, e.g., a yet to be identified pathogen.

In some embodiments, the sample comprising the pathogen is contacted with two or more test compounds, e.g., simultaneously or in the same sample, e.g., contacted with known or potential treatment compounds, e.g., antibiotics, antifungals, antivirals, and antiparasitics. A number of these compounds are known in the art, e.g., isoniazid, rifampicin, pyrazinamide, ethambutol streptomycin, amikacin, kanamycin, capreomycin, viomycin, enviomycin, ciprofloxacin, levofloxacin, moxifloxacin, ethionamide, prothionamide, cycloserine, p-aminosalicylic acid, rifabutin, clarithromycin, linezolid, thioacetazone, thioridazine, arginine, vitamin D, R207910, ofloxacin, novobiocin, tetracycline, merepenem, gentamicin, neomycin, netilmicin, streptomycin, tobramycin, paromomycin, geldanamycin, herbimycin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, methicillin, nafcillin, oxacillin, penicillin, piperacillin, ticarcillin, bacitracin, colistin, polymyxin B, enoxacin, gatifloxacin, lomefloxacin, norfloxacin, trovafloxacin, grepafloxacin, sparfloxacin, mafenide, prontosil, sulfacetamide, sulfamethizole, sulfanilimide, sulfasalazine, sulfisoxazole, trimethoprim, trimethoprim-sulfamethoxazole (co-trimoxazole), demeclocycline, doxycycline, minocycline, oxytetracycline, arsphenamine, chloramphenicol, clindamycin, lincomycin, ethambutol, fosfomycin, fusidic acid, furazolidone, metronidazole, mupirocin, nitrofurantoin, platensimycin, quinupristin/dalfopristin, rifampin, thiamphenicol, tinidazole, cephalosporin, teicoplatin, augmentin, cephalexin, rifamycin, rifaximin, cephamandole, ketoconazole, latamoxef, or cefmenoxime.

In some embodiments, the sample is contacted with the compound for less than four hours, e.g., less than three hours, less than two hours, less than one hour, less than 30 minutes, less than 20 minutes, less than 10 minutes, less than five minutes, less than two minutes, less than one minute.

In another aspect, the invention features methods of identifying an infectious disease pathogen, e.g., a bacterium, fungus, virus, or parasite, e.g., *Mycobacterium tuberculosis*, e.g., detecting the presence of the pathogen in a sample, e.g., a clinical sample. The methods include:

providing a test sample from a subject suspected of being infected with a pathogen;
treating the test sample under conditions that release messenger ribonucleic acid (mRNA);
exposing the test sample to a plurality of nucleic acid probes, comprising a plurality of subsets of probes, wherein each subset comprises one or more probes that bind specifically to a target mRNA that uniquely identifies a pathogen, wherein the exposure occurs for a time and under conditions in which binding between the probe and the target mRNA can occur; and
determining a level of binding between the probe and target mRNA, thereby determining a level of target mRNA. An increase in the target mRNA of the test sample, relative to a reference sample, indicates the identity of the pathogen in the test sample.

In some embodiments, the methods identify an infectious disease pathogen in or from a sample that is or comprises sputum, blood, urine, stool, joint fluid, cerebrospinal fluid, and cervical/vaginal swab. Such samples may include a plurality of other organisms (e.g., one or more non-disease causing bacteria, fungi, viruses, or parasites) or pathogens. In some embodiments, the sample is a clinical sample, e.g., a sample from a patient or person who is or may be undergoing a medical treatment by a health care provider.

In some embodiments of the invention, the one or more nucleic acid probes are selected from Table 2.

In some embodiments, the mRNA is crude, e.g., not purified, before contact with the probes and/or does not include amplifying the mRNA, e.g., to produce cDNA.

In some embodiments, the methods comprise lysing the cells enzymatically, chemically, and/or mechanically.

In some embodiments, the methods comprise use of a microfluidic device.

In some embodiments, the methods are used to monitor pathogen infection, e.g., incidence, prevalence, for public health surveillance of an outbreak of a pathogen, e.g., a sudden rise in numbers of a pathogen within a particular area.

The methods described herein are effective wherein the pathogen is in a sample from a subject, including humans and animals, such as laboratory animals, e.g., mice, rats, rabbits, or monkeys, or domesticated and farm animals, e.g., cats, dogs, goats, sheep, pigs, cows, horses, and birds, e.g., chickens.

In some embodiments, the methods further feature determining and/or selecting a treatment for the subject and optionally administering the treatment to the subject, based on the outcome of an assay as described herein.

In another general aspect, the invention features methods of selecting a treatment for a subject. The methods include:

optionally identifying an infectious disease pathogen (e.g., detecting the presence and/or identity of a specific pathogen in a sample), e.g., using a method described herein;
determining the drug sensitivity of the pathogen using the methods described herein; and
selecting a drug to which the pathogen is sensitive for use in treating the subject.

In yet another aspect, the invention provides methods for monitoring an infection with a pathogen in a subject. The methods include:

obtaining a first sample comprising the pathogen at a first time;
determining the drug sensitivity of the pathogen in the first sample using the method described herein;
optionally selecting a treatment to which the pathogen is sensitive and administering the selected treatment to the subject;
obtaining a second sample comprising the pathogen at a second time;
determining the drug sensitivity of the pathogen in the second sample using the method described herein; and
comparing the drug sensitivity of the pathogen in the first sample and the second sample, thereby monitoring the infection in the subject.

In some embodiments of the methods described herein, the subject is immune compromised.

In some embodiments of the methods described herein, the methods include selecting a treatment to which the pathogen is sensitive and administering the selected treatment to the subject, and a change in the drug sensitivity of the pathogen indicates that the pathogen is or is becoming resistant to the treatment, e.g., the methods include determining the drug sensitivity of the pathogen to the treatment being administered.

In some embodiments, a change in the drug sensitivity of the pathogen indicates that the pathogen is or is becoming resistant to the treatment, and the method further comprises administering a different treatment to the subject.

In yet another aspect, the invention features methods of monitoring an infection with a pathogen in a population of subjects. The methods include:

- obtaining a first plurality of samples from subjects in the population at a first time;
- determining the drug sensitivity of pathogens in the first plurality of samples using the method described herein, and optionally identifying an infectious disease pathogen in the first plurality of samples using the method described herein;
- optionally administering a treatment to the subjects;
- obtaining a second plurality of samples from subjects in the population at a second time;
- determining the drug sensitivity of pathogens in the second plurality of samples using the method described herein, and optionally identifying an infectious disease pathogen in the first plurality of samples using the method described herein;
- comparing the drug sensitivity of the pathogens, and optionally the identity of the pathogens, in the first plurality of samples and the second plurality of samples, thereby monitoring the infection in the population of subject.

In yet another aspect, a plurality of polynucleotides bound to a solid support are provided. Each polynucleotide of the plurality selectively hybridizes to one or more genes from Table 2. In some embodiments, the plurality of polynucleotides comprise SEQ ID NOs:1-227, and any combination thereof.

"Infectious diseases" also known as communicable diseases or transmissible diseases, comprise clinically evident illness (i.e., characteristic medical signs and/or symptoms of disease) resulting from the infection, presence, and growth of pathogenic biological agents in a subject (Ryan and Ray (eds.) (2004). Sherris Medical Microbiology (4th ed.). McGraw Hill). A diagnosis of an infectious disease can confirmed by a physician through, e.g., diagnostic tests (e.g., blood tests), chart review, and a review of clinical history. In certain cases, infectious diseases may be asymptomatic for some or all of their course. Infectious pathogens can include viruses, bacteria, fungi, protozoa, multicellular parasites, and prions. One of skill in the art would recognize that transmission of a pathogen can occur through different routes, including without exception physical contact, contaminated food, body fluids, objects, airborne inhalation, and through vector organisms. Infectious diseases that are especially infective are sometimes referred to as contagious and can be transmitted by contact with an ill person or their secretions.

As used herein, the term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" as used herein refers to an oligonucleotide that binds specifically to a target mRNA. A probe can be single stranded at the time of hybridization to a target.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

*P. aeruginosa*: ciprofloxacin, and (C) *M. tuberculosis*: isoniazid (INH), streptomycin (SM), or ciprofloxacin (CIP). Each strain was tested in duplicate; error bars represent standard deviation of two biological replicates of one representative strain. See Table 6 for a full list of strains tested.

Figure 24:
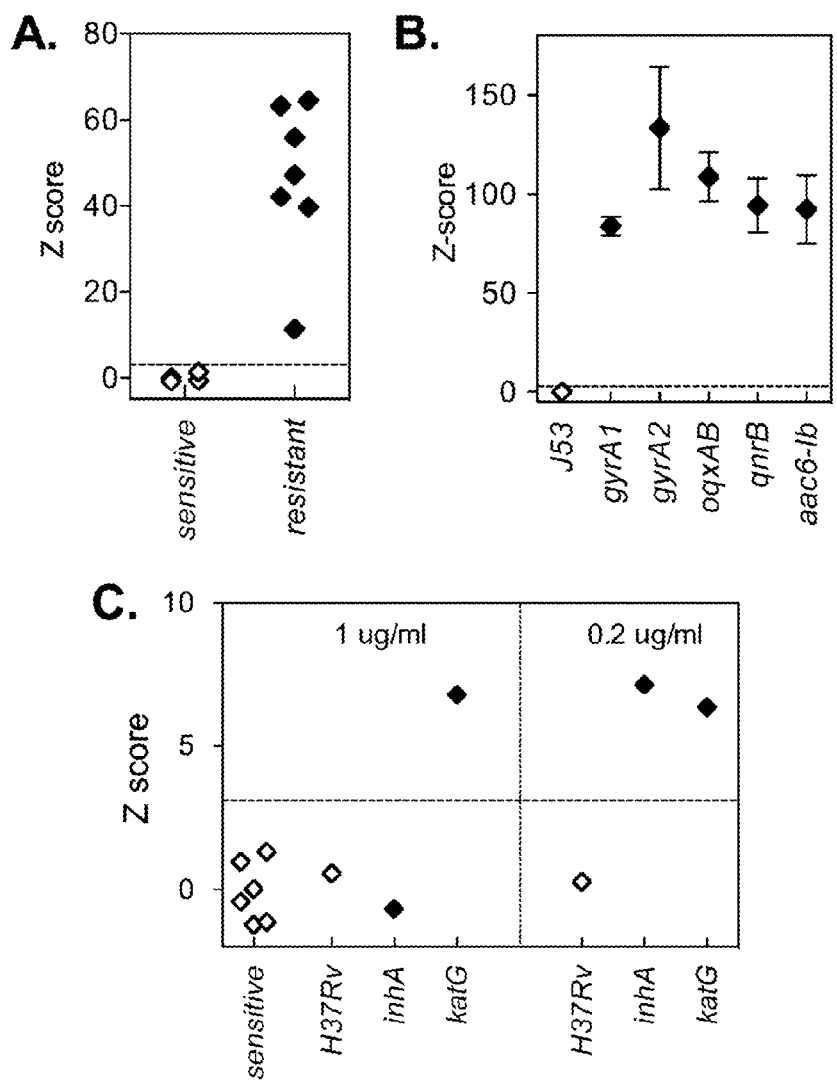

FIG. 24 is a panel of three scatter plots showing statistical separation of antibiotic-resistant and sensitive bacterial strains using mean squared distance of the induction levels of expression signatures. Mean squared distance (MSD) is represented as Z-scores showing deviation of each tested strain from the mean signal for susceptible strains exposed to antibiotic. Susceptible strains: open diamonds; resistant strains: solid diamonds. Dashed line: Z=3.09 (p=0.001) (A) *E. coli* clinical isolates. Each point represents 2 to 4 biological replicates of one strain. (B and C) Expression-signature response to antibiotic exposure is independent of resistance mechanism. (B) *E. coli*. Parent strain J53 and derivatives containing either a chromosomal fluoroquinolone resistance-conferring mutation in gyrA or plasmid-mediated quinolone resistance determinants (aac(6)-Ib, qnrB, or oqxAB) were exposed to ciprofloxacin, then analyzed as above. Error bars represent standard deviation of four biological replicates. (C) *M. tuberculosis*. Isoniazid-sensitive and high- or low-level resistant strains were exposed to isoniazid. At 1 µg/mL, the low-level INH-resistant inhA displays a susceptible signature, but at 0.2 µg/mL, it shows a resistant signature.

Figure 25:
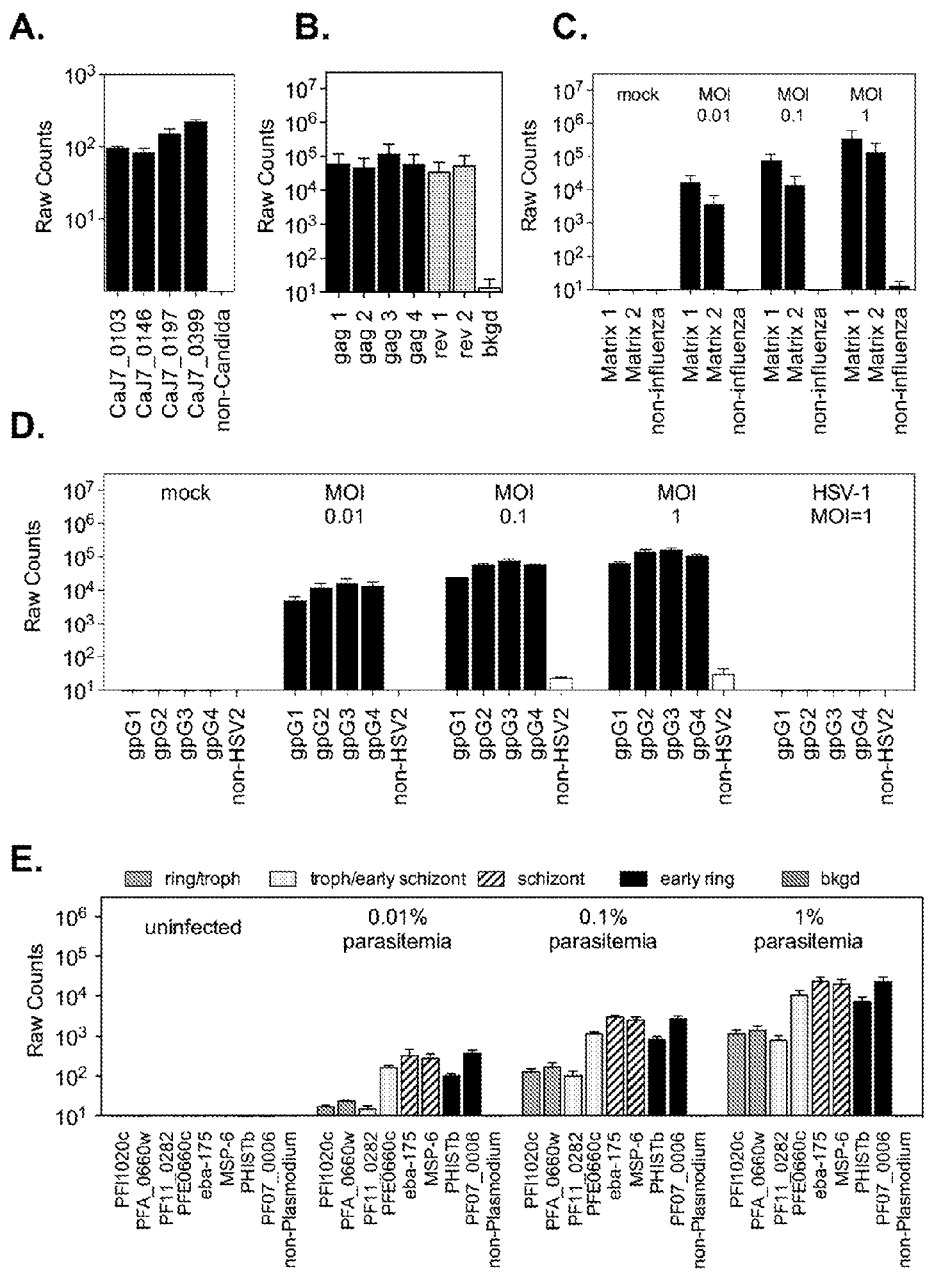

FIG. 25 is a panel of five bar graphs depicting detection of viruses and parasites. Cells were lysed, pooled probe sets added, and samples hybridized according to standard NanoString™ protocols. (A) *Candida albicans* detected from axenic culture. (B) HIV-1. Detection from PBMC lysates with probes designed to HIV-1 gag and rev. (C) Influenza A. Detection of PR8 influenza virus in 293T cell lysates with probes designed to matrix proteins 1 and 2. (D) HSV-1 and HSV-2. Detection of HSV-2 strain 186 Syn+ in HeLa cell lysates with probes designed to HSV-2 glycoprotein G. There was little cross-hybridization of the HSV-2 specific probes with HSV-1 even at high MOI. (E) *Plasmodium falciparum*. Detection of *P. falciparum* strain 3D7 from red blood cells harvested at the indicated levels of parasitemia. Probes were designed to the indicated blood stage for *P. falciparum*.

Figure 26:
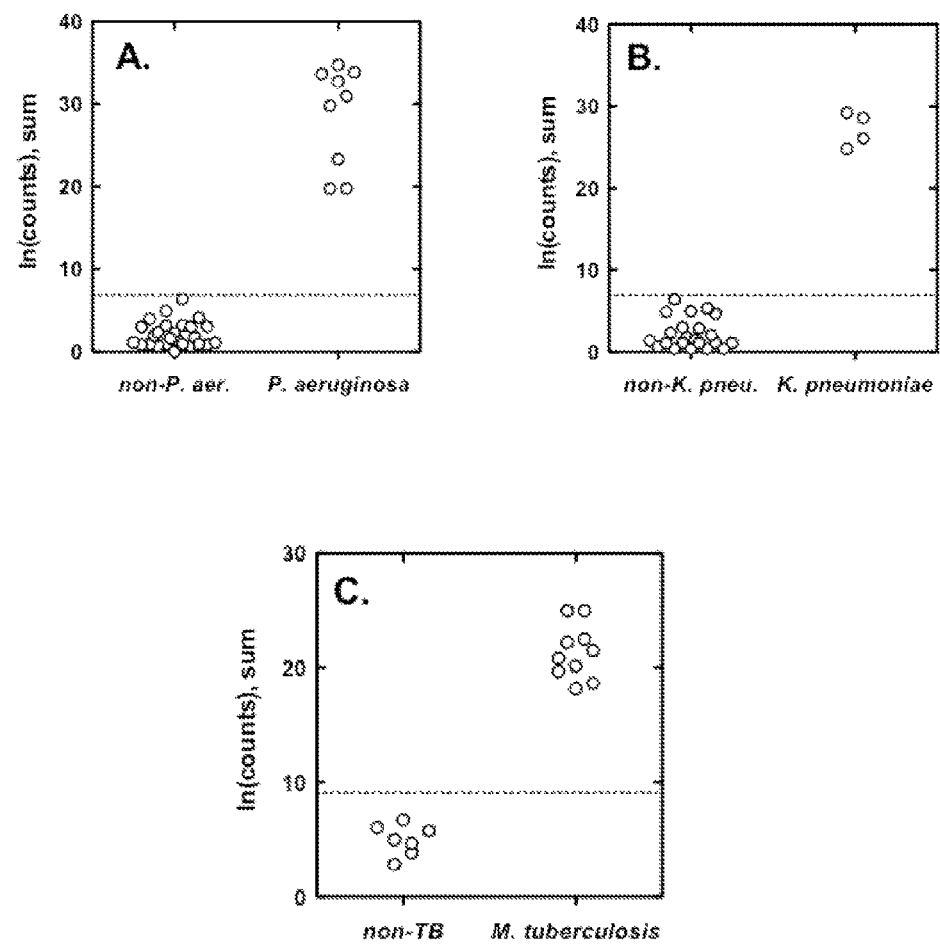

FIG. 26 is a panel of three scatter plots showing organism identification of clinical isolates. Bacterial cultures were lysed and probes that were designed to detect species-specific transcripts were added, hybridized, and detected by standard NanoString™ protocol. A pooled probe-set containing probes that identify *E. coli*, *K. pneumoniae*, or *P. aeruginosa* were used in A and B. In C, species-specific probes for *M. tuberculosis* were among a larger set of probes against microbial pathogens. The left Y-axis shows the sum of the log-transformed counts from 1-5 independent transcripts for each organism and X-axis indicates the species tested. The dashed line delineates a p value of 0.001 based on the number of standard deviations that the score of a given sample falls from the mean of the control ("non-organism") samples. "Non-organism" samples indicate samples tested that contained other bacterial organisms but where the defined organism was known to be absent. For (C), non-organism samples were non-tuberculous mycobacteria including *M. intracellulare, M. paratuberculosis, M. abscessus, M. marinum, M. gordonae*, and *M. fortuitum*. Numbers of strains and clinical isolates tested are shown in Table 4 and genes used for pathogen identification (for which 50 nt probes were designed) are listed in Table 5.

Figure 27:
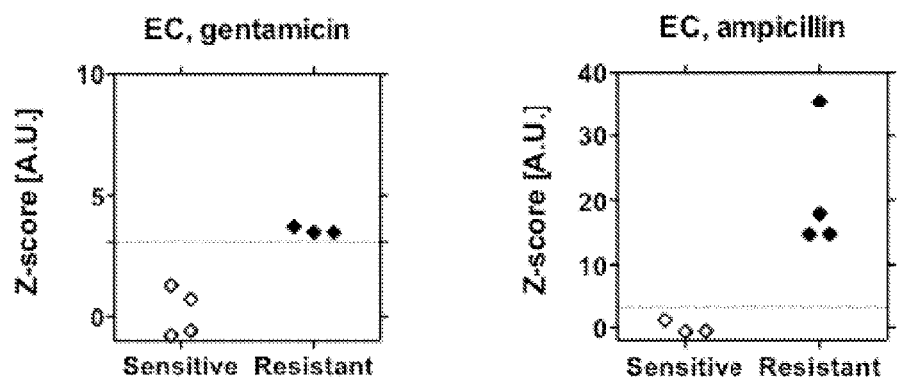

FIG. 27 depicts the mean square distance (MSD) comparison of gentamicin (left panel) or ampicillin (left panel) sensitive and resistant *E. coli* strains. The Y axis shows the Z score of the MSD of each sample relative to the centroid of the response of known sensitive strains. The dotted line delineates Z=3.09, which corresponds to a p value of 0.001.

Figure 28:
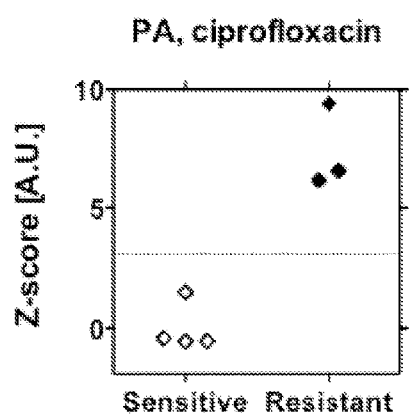

FIG. 28 is a scatter plot showing mean square distance comparison of ciprofloxacin sensitive and resistant *P. aeruginosa* strains. The Y axis shows the Z score of the MSD of each sample relative to the centroid of the response of known sensitive strains.

Figure 29:
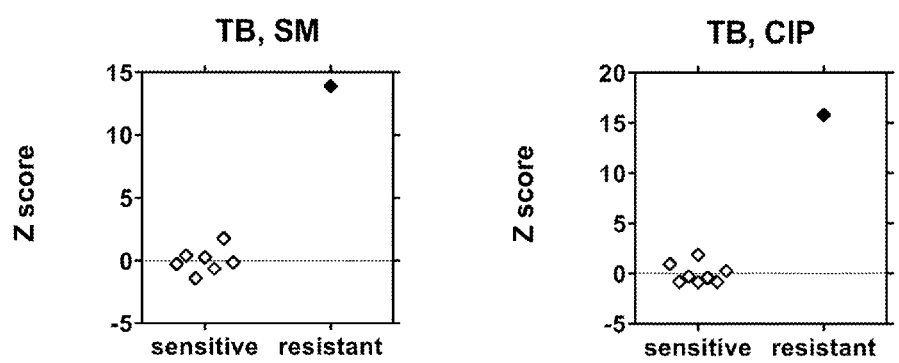

FIG. 29 is a panel of two scatter plots showing mean square distance comparison of streptomycin (SM) or ciprofloxacin (CIP) sensitive and resistant *M. tuberculosis* strains. The Y axis shows the Z score of the MSD of each sample relative to the centroid of the response of known sensitive strains.

Figure 30:
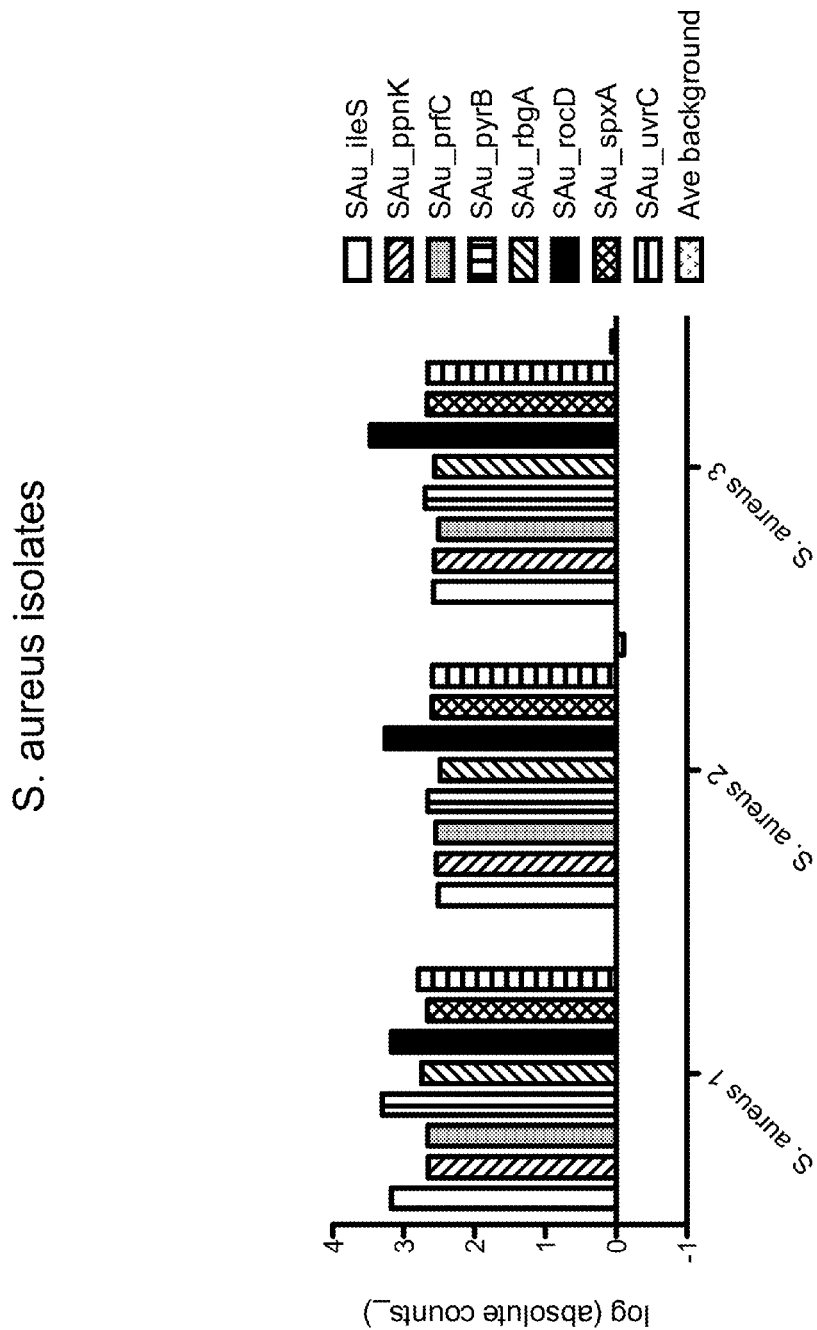

FIG. 30 is a bar graph showing positive identification of *S. aureus* isolates. Using probes designed to five *S. aureus* genes (ileS, ppnK, pyrB, rocD, and uvrC), three *S. aureus* isolates were positively identified.

Figure 31:
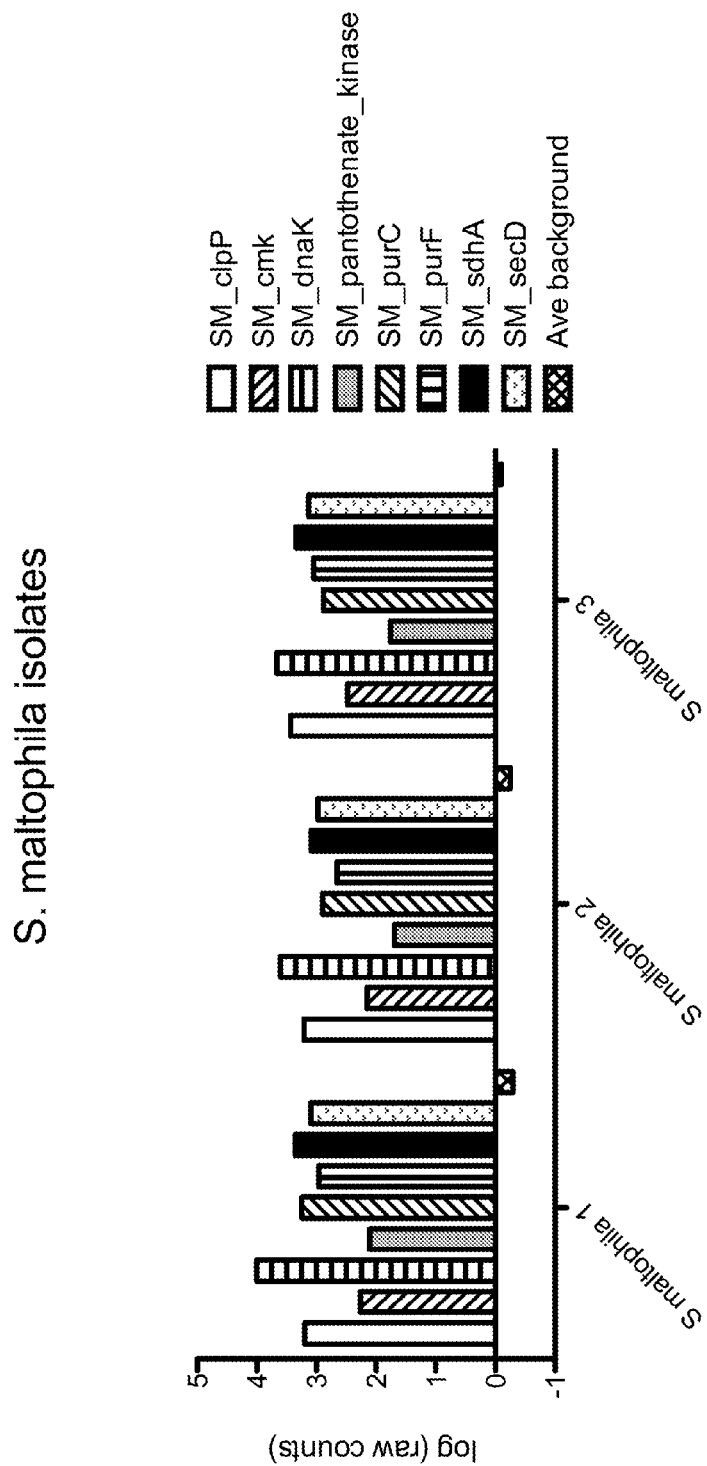

FIG. 31 is a bar graph showing positive identification of *Stenotrophomonas maltophilia* isolates. Using probes designed to six *S. maltophilia* genes (clpP, dnaK, purC, purF, sdhA, and secD), three isolates were positively identified as *S. maltophilia*.

DETAILED DESCRIPTION

Described herein are rapid, highly sensitive, phenotypic-based methods for both identifying a pathogen, e.g., bacterium, fungus, virus, and parasite, and its drug resistance pattern based on transcriptional expression profile signatures. Sensitive and resistant pathogens respond very differently to drug exposure with one of the earliest, most rapid responses reflected in alterations in their respective expression profiles. Digital gene expression with molecular barcodes can be used to detect these early transcriptional responses to drug exposure to distinguish drug sensitive and resistant pathogens in a rapid manner that requires no enzymology or molecular biology. The invention is applicable to a broad range of microbial pathogens in a variety of clinical samples and can be used in conjunction with current diagnostic tools or independently. The methods will be described primarily for use with tuberculosis ("TB;" *Mycobacterium tuberculosis*), although it will be understood by skilled practitioners that they may be adapted for use with other pathogens and their associated clinical syndromes (e.g., as listed in Table 1).

The diagnosis and the identification of drug resistance is especially challenging regarding TB due to the extremely slow growth of TB that is required for culture testing even using the more rapid "microscopic-observation drug-susceptibility" (MODS) culture method, phage-delivered reporters, or colorimetric indicators. An alternative approach to determining drug resistance is based on defining the genotype of the infecting pathogen relative to known resistance conferring mutations, however, this approach requires a fairly comprehensive identification of all resistance-conferring single nucleotide polymorphisms (SNPs) in order for the test to have high sensitivity.

The methods described herein can be used, e.g., for identifying a pathogen in a sample, e.g., a clinical sample, as well as determining the drug sensitivity of a pathogen based on expression profile signatures of the pathogen. One of the earliest, most rapid responses that can be used to distinguish drug sensitive and resistant pathogens is their respective transcriptional profile upon exposure to a drug of interest. Pathogens respond very differently to drug exposure depending on whether they are sensitive or resistant to that particular drug. For example, in some cases drug sensitive or drug resistant bacteria will respond within minutes to hours to drug exposure by up- and down-regulating genes, perhaps attempting to overcome the drug as well as the more non-specific stresses that follow while resistant bacteria have no such response. This rapid response is in contrast to the longer time that is required by a compound to kill or inhibit growth of a pathogen. Detecting death or growth inhibition of a pathogen in an efficient manner from clinical samples represents an even greater challenge. Digital gene expression can be used, e.g., with molecular barcodes, to detect these early transcriptional responses to drug exposure to distinguish drug sensitive and resistant pathogens in a rapid manner that requires no enzymology or molecular biology, and thus can be performed directly on crude clinical samples collected from patients. This readout is phenotypic and thus requires no comprehensive definition of SNPs accounting for, e.g., TB drug resistance. Described herein are a set of genes that will provide high specificity for a pathogen, e.g., TB bacillus, and for distinguishing sensitive and resistant pathogens. Based on the selection of genes that constitute the expression signature distinguishing sensitive and resistant pathogens, the sensitivity of the detection limit is optimized by choosing transcripts that are abundantly induced, and thus not limited solely by the number of pathogens within a clinical sample. The size of this set is determined to minimize the numbers of genes required. Thus, the current invention can be used as a highly sensitive, phenotypic test to diagnose a pathogen with its accompanying resistance pattern that is rapid (e.g., a few hours), sensitive, and specific. This test can transform the care of patients infected with a pathogen and is a cost-effective, point-of-care diagnostic for, e.g., TB endemic regions of the world.

Figure 1:
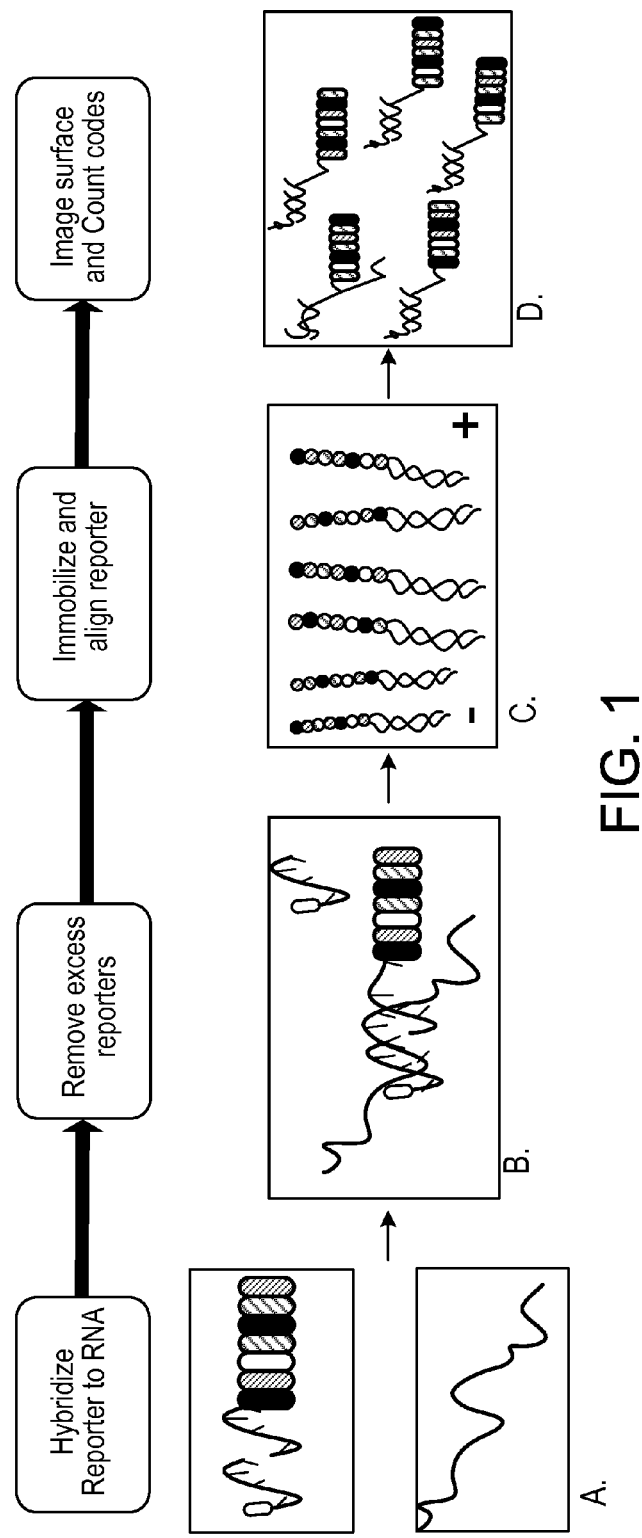
FIGS. 1A to 1D are a flowchart illustrating an exemplary method to quantify mRNA molecules in a sample using NanoString™ (direct multiplexed measurement of gene expression with color-coded probe pairs) technology. 1A. Two molecular probes corresponding to each mRNA of interest are added to crude sample lysate. The capture probe consists of a 50 bp oligomer complementary to a given mRNA molecule, conjugated to biotin. The reporter probe consists of a different 50 bp oligomer complementary to a different part of the same mRNA molecule, conjugated to a fluorescent tag. Each tag uniquely identifies a given mRNA molecule. The capture and reporter probes hybridize to their corresponding mRNA molecules within the lysate. 1B. Excess reporter is removed by bead purification that hybridizes to a handle on each oligomer, leaving only the hybridized mRNA complexes. 1C. The mRNA complexes are immobilized and aligned on a surface. The mRNA complexes are captured by the biotin-conjugated captures probes onto a strepavidin-coated surface. An electric field is applied to align the complexes all in the same direction on the surface. 1D. Surface is imaged and codes counted. The mRNA complexes are microscopically imaged and the aligned reporter tags can be counted, thus providing a quantitative measure of mRNA molecules. (Images obtained from nanostring.com).

The present methods allow the detection of nucleic acid signatures, specifically RNA levels, directly from crude cellular samples with a high degree of sensitivity and specificity. This technology can be used to identify TB and determine drug sensitivity patterns through measurement of distinct expression signatures with a high degree of sensitivity and with rapid, simple processing directly from clinical samples, e.g. sputum, urine, blood, or feces; the technology is also applicable in other tissues such as lymph nodes. High sensitivity can be attained by detecting mRNA rather than DNA, since a single cell can carry many more copies of mRNA per cell ($>10^3$) compared to a single genomic DNA copy (which typically requires amplification for detection), and by the high inherent sensitivity of the technology (detects <2000 copies mRNA). The rapid, simple sample processing is possible due to the lack of enzymology and molecular biology required for detection of mRNA molecules; instead, in some embodiments, the methods make use of hybridization of bar-coded probes to the mRNA molecules in crude lysates followed by direct visualization (e.g., as illustrated in FIG. 1). Because hybridization is used in these embodiments, mRNA can be detected directly without any purification step from crude cell lysates, fixed tissue samples, and samples containing guanidinium isothiocyanate, polyacrylamide, and Trizol®. Crude mRNA samples can be obtained from biological fluids or solids, e.g., sputum, blood, urine, stool, joint fluid, cerebrospinal fluid, cervical/vaginal swab, biliary fluid, pleural fluid, peritoneal fluid, or pericardial fluid; or tissue biopsy samples, e.g., from bone biopsy, liver biopsy, lung biopsy, brain biopsy, lymph node biopsy, esophageal biopsy, colonic biopsy, gastric biopsy, small bowel biopsy, myocardial biopsy, skin biopsy, and sinus biopsy can also be used.

RNA Extraction

RNA can be extracted from cells in a sample, e.g., a pathogen cell or clinical sample, by treating the sample enzymatically, chemically, or mechanically to lyse cells in the sample and release mRNA. It will be understood by skilled practitioners that other disruption methods may be used in the process.

The use of enzymatic methods to remove cell walls is well-established in the art. The enzymes are generally commercially available and, in most cases, were originally isolated from biological sources. Enzymes commonly used include lysozyme, lysostaphin, zymolase, mutanolysin, glycanases, proteases, and mannose.

Chemicals, e.g., detergents, disrupt the lipid barrier surrounding cells by disrupting lipid-lipid, lipid-protein and protein-protein interactions. The ideal detergent for cell lysis depends on cell type and source. Bacteria and yeast have differing requirements for optimal lysis due to the nature of their cell wall. In general, nonionic and zwitterionic detergents are milder. The Triton X series of nonionic detergents and 3-[(3-Cholamidopropyl)dimethylammonio]-1-propane-sulfonate (CHAPS), a zwitterionic detergent, are commonly used for these purposes. In contrast, ionic detergents are strong solubilizing agents and tend to denature proteins, thereby destroying protein activity and function. SDS, an ionic detergent that binds to and denatures proteins, is used extensively in the art to disrupt cells.

Physical disruption of cells may entail sonication, French press, electroporation, or a microfluidic device comprising fabricated structures can be used to mechanically disrupt a cell. These methods are known in the art.

Digital Gene Expression with Molecular Barcodes

A flow diagram is shown in FIG. 1 of an exemplary procedure to identify a pathogen based on its gene expression profile. Oligonucleotide probes to identify each pathogen of interest were selected by comparing the coding sequences from the pathogen of interest to all gene sequences in other organisms by BLAST software. Only probes of about 50 nucleotides, e.g., 80 nucleotides, 70 nucleotides, 60 nucleotides, 40 nucleotides, 30 nucleotides, and 20 nucleotides, with a perfect match to the pathogen of interest, but no match of >50% to any other organism were selected. Two probes corresponding to each mRNA of interest and within 100 base pairs of each other are selected.

Two molecular probes are added to a crude sample lysate containing mRNA molecules. A capture probe comprises 50 nucleotides complementary to a given mRNA molecule, and can be conjugated to biotin. A reporter probe comprises a different 50 nucleotides complementary to a different part of the same mRNA molecule, and can be conjugated to a reporter molecule, e.g., a fluorescent tag or quantum dot. Each reporter molecule uniquely identifies a given mRNA molecule. The capture and reporter probes hybridize to their corresponding mRNA molecules within the lysate. Excess reporter is removed by bead purification that hybridizes to a handle on each oligomer, leaving only the hybridized mRNA complexes. The mRNA complexes can be captured and immobilized on a surface, e.g., a streptavidin-coated surface. An electric field can be applied to align the complexes all in the same direction on the surface before the surface is microscopically imaged.

The reporter molecules can be counted to provide a quantitative measure of mRNA molecules. A commercially available nCounter™ Analysis System (NanoString, Seattle, Wash.) can be used in the procedure. However, it will be understood by skilled practitioners that other systems may be used in the process. For example, rather than bar codes the probes can be labeled with quantum dots; see, e.g., Sapsford et al., "Biosensing with luminescent semiconductor quantum dots." Sensors 6(8): 925-953 (2006); Stavis et al., "Single molecule studies of quantum dot conjugates in a submicrometer fluidic channel." Lab on a Chip 5(3): 337-343 (2005); and Liang et al., "An oligonucleotide microarray for microRNA expression analysis based on labeling RNA with quantum dot and nanogold probe." Nucleic Acids Research 33(2): e17 (2005).

In some embodiments, microfluidic (e.g., "lab-on-a-chip") devices can be used in the present methods for detection and quantification of mRNA in a sample. Such devices have been successfully used for microfluidic flow cytometry, continuous size-based separation, and chromatographic separation. In particular, such devices can be used for the detection of specific target mRNA in crude samples as described herein. A variety of approaches may be used to detect changes in levels of specific mRNAs. Accordingly, such microfluidic chip technology may be used in diagnostic and prognostic devices for use in the methods described herein. For examples, see, e.g., Stavis et al., Lab on a Chip 5(3): 337-343 (2005); Hong et al., Nat. Biotechnol. 22(4): 435-439 (2004); Wang et al., Biosensors and Bioelectronics 22(5): 582-588 (2006); Carlo et al., Lab on a Chip 3(4): 287-291 (2003); Lion et al., Electrophoresis 24 21 3533-3562 (2003); Fortier et al., Anal. Chem., 77(6):1631-1640 (2005); U.S. Patent Publication No. 2009/0082552; and U.S. Pat. No. 7,611,834. Also included in the present application are microfluidic devices comprising binding moieties, e.g., antibodies or antigen-binding fragments thereof that bind specifically to the pathogens as described herein.

These microfluidic devices can incorporate laser excitation of labeled quantum dots and other reporter molecules. The devices can also incorporate the detection of the resulting emission through a variety of detection mechanisms including visible light and a variety of digital imaging sensor methods including charge-coupled device based cameras. These devices can also incorporate image processing and analysis capabilities to translate the resulting raw signals and data into diagnostic information.

Rapid, Phenotypic Diagnosis of Pathogen Identity and Pathogen Drug Resistance Using Expression Signatures This technology can be applied to obtain a rapid determination of identity or drug resistance of a pathogen.

A pathogen can be identified in a sample based on detection of unique genes. Thus, for example, a sputum sample may be obtained from a subject who has symptoms associated with a respiratory disease such as pneumonia or bronchitis, and an assay is performed to determine which disease is present and what pathogen is the cause of that disease (see, e.g., Table 1). Urine samples may be obtained to diagnose cystitis, pyelonephritis, or prostatitis (see, e.g., Table 1). A skilled practitioner will appreciate that a particular type of sample can be obtained and assayed depending on the nature of the symptoms exhibited by the patient and the differential diagnosis thereof. Specific genes for identifying each organism can be identified by methods described herein; exemplary genes for identifying certain pathogens are included in Table 2.

The principle for greatly accelerated resistance testing is based on detecting the differences in transcriptional response that occur between drug sensitive and resistant strains of a pathogen upon exposure to a particular drug of interest. These transcriptional profiles are the earliest phenotypic response to drug exposure that can be measured and they can be detected long before bacillary death upon drug exposure. This transcription-based approach also carries the distinct advantage over genotype-based approaches in that it measures direct response of the pathogen to drug exposure rather than a surrogate SNP.

Figure 2:
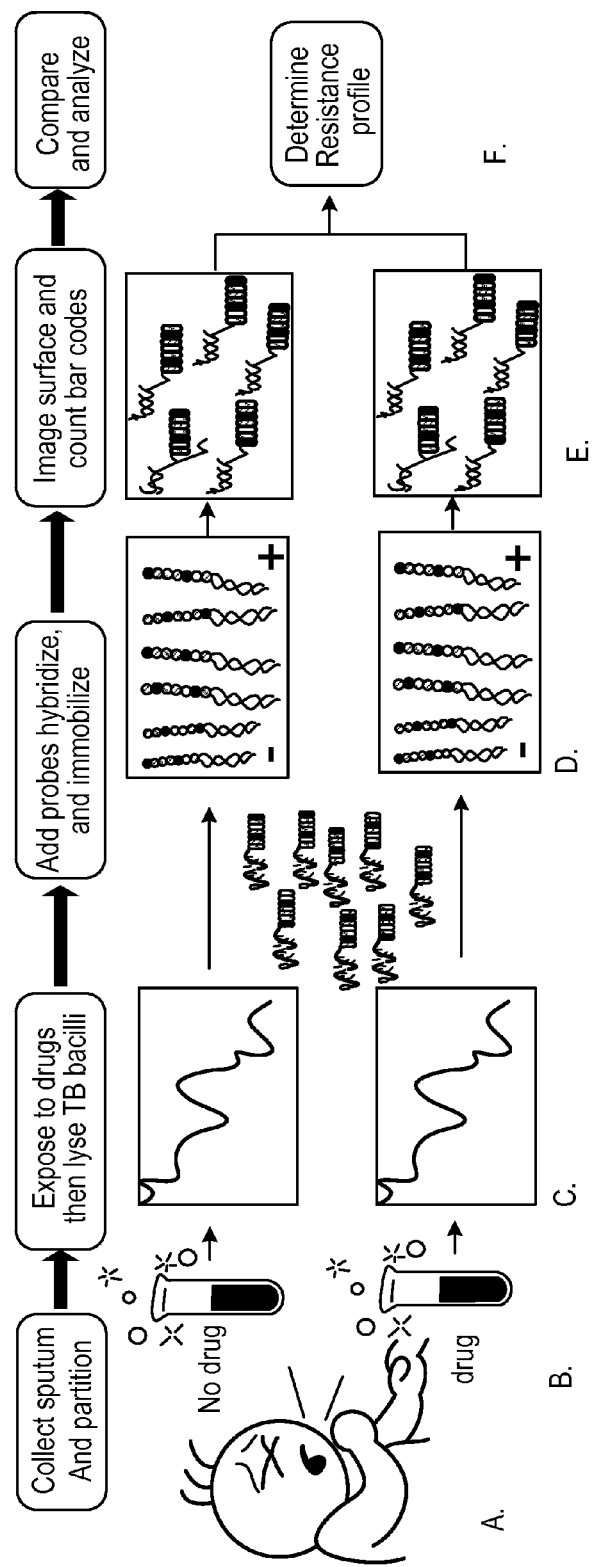
FIGS. 2A to 2F are a panel of figures showing diagnosis of a gene expression signature of drug resistance. 2A. Sample from a patient, e.g., sputum. 2B. Induction of expression program to distinguish drug sensitive and resistant strains. Sample is partitioned and exposed to different drugs to induce an expression program depending on whether the strain is drug resistant or sensitive. 2C. Barcoded probes hybridize to mRNA molecules. Cells are lysed and probes added to the crude sample. 2D. mRNA complexes are captured and aligned. 2E. Complexes are imaged and counted. 2F. Analysis of signatures. The measured mRNA levels will be normalized and compared to the no drug control and drug sensitive and resistant standards to define a resistance profile across all drugs.

In some embodiments, the test can be performed as described in FIG. 2. A sample, e.g., a sputum sample from a patient with TB, is partitioned into several smaller sub-samples. The different sub-samples are exposed to either no drug or different, known or potential drugs (e.g., in the case of a TB sample, isoniazid, rifampin, ethambutol, moxifloxacin, streptomycin) for a determined period of time (e.g., less than four hours, less than three hours, less than two hours, less than one hour, less than 30 minutes, less than 20 minutes, less than 10 minutes, less than five minutes, less than two minutes, less than one minute), during which an expression profile is induced in drug sensitive strains that distinguishes it from drug resistant strains. The TB bacilli in the sub-samples are then lysed, the bar-coded molecular probes added for hybridization, and the sub-samples analyzed after immobilization and imaging. The set of transcriptional data is then analyzed to determine resistance to a panel of drugs based on expression responses for drug sensitive and drug resistant strains of TB. Thus, an expression signature to uniquely identify TB and its response to individual antibiotics can be determined, a probe set for the application of digital gene expression created, and sample processing and collection methods optimized.

Two issues that should be taken into account in defining the expression signatures and optimizing the transcriptional signal are: 1. the currently undefined metabolic state of the bacilli in sputum since the cells may be in either a replicating or non-replicating state, and 2. the possibility that the TB bacilli in collected sputum have been pre-exposed to antibiotics (i.e., the patient has already been treated empirically with antibiotics).

In some embodiments, the methods of identifying a pathogen and the methods of determining drug sensitivity are performed concurrently, e.g., on the same sample, in the same microarray or microfluidic device, or subsequently, e.g., once the identity of the pathogen has been determined, the appropriate assay for drug sensitivity is selected and performed.

An exemplary set of genes and probes useful in the methods described herein is provided in Table 2 submitted herewith.

Methods of Treatment

The methods described herein include, without limitation, methods for the treatment of disorders, e.g., disorders listed in Table 1. Generally, the methods include using a method described herein to identify a pathogen in a sample from a subject, or identify a drug (or drugs) to which a pathogen in a subject is sensitive, and administering a therapeutically effective amount of therapeutic compound that neutralizes the pathogen to a subject who is in need of, or who has been determined to be in need of, such treatment. As used in this context, to "treat" means to ameliorate at least one symptom of the disorder associated with one of the disorders listed in Table 1. For example, the methods include the treatment of TB, which often results in a cough, chest pain, fever, fatigue, unintended weight loss, loss of appetite, chills and night sweats, thus, a treatment can result in a reduction of these symptoms. Clinical symptoms of the other diseases are well known in the art.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week, including once every other day. The compositions can also be administered from one or more times per month to one or more times per year. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Methods of Diagnosis

Included herein are methods for identifying a pathogen and/or determining its drug sensitivity. The methods include obtaining a sample from a subject, and evaluating the presence and/or drug sensitivity of a pathogen in the sample, and comparing the presence and/or drug sensitivity with one or more references, e.g., a level in an unaffected subject or a wild type pathogen. The presence and/or level of a mRNA can be evaluated using methods described herein and are known in the art, e.g., using quantitative immunoassay methods. In some embodiments, high throughput methods, e.g., gene chips as are known in the art (see, e.g., Ch. 12, Genomics, in Griffiths et al., Eds. Modern Genetic Analysis, 1999, W.H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of mRNA.

In some embodiments, the sample includes biological fluids or solids, e.g., sputum, blood, urine, stool, joint fluid, cerebrospinal fluid, cervical/vaginal swab, biliary fluid, pleural fluid, peritoneal fluid, or pericardial fluid; or tissue biopsy samples, e.g., from a bone biopsy, liver biopsy, lung biopsy, brain biopsy, lymph node biopsy, esophageal biopsy, colonic biopsy, gastric biopsy, small bowel biopsy, myocardial biopsy, skin biopsy, and sinus biopsy. In some embodiments, once it has been determined that a person has a pathogen, e.g., a pathogen listed in Table 1, or has a drug-resistant pathogen, then a treatment, e.g., as known in the art or as described herein, can be administered.

Kits

Also within the scope of the invention are kits comprising a probe that hybridizes with a region of gene as described herein and can be used to detect a pathogen described herein. The kit can include one or more other elements including: instructions for use; and other reagents, e.g., a label, or an agent useful for attaching a label to the probe. Instructions for use can include instructions for diagnostic applications of the probe for predicting response to treatment in a method described herein. Other instructions can include instructions for attaching a label to the probe, instructions for performing analysis with the probe, and/or instructions for obtaining a sample to be analyzed from a subject. As discussed above, the kit can include a label, e.g., a fluorophore, biotin, digoxygenin, and radioactive isotopes such as $^{32}$P and $^{3}$H. In some embodiments, the kit includes a labeled probe that hybridizes to a region of gene as described herein, e.g., a labeled probe as described herein.

The kit can also include one or more additional probes that hybridize to the same gene or another gene or portion thereof that is associated with a pathogen. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of sputum, buccal cells, or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

In some embodiments, the kits can include one or more reagents for processing a sample. For example, a kit can include reagents for isolating mRNA from a sample. The kits can also, optionally, contain one or more reagents for detectably-labeling an mRNA or mRNA amplicon, which reagents can include, e.g., an enzyme such as a Klenow fragment of DNA polymerase, T4 polynucleotide kinase, one or more detectably-labeled dNTPs, or detectably-labeled gamma phosphate ATP (e.g., $^{33}$P-ATP).

In some embodiments, the kits can include a software package for analyzing the results of, e.g., a microarray analysis or expression profile.

The invention is further described in the following examples, which do not limit the scope of the invention described in the claims.

EXAMPLES

Example 1

Pathogen Identification

Figure 3:
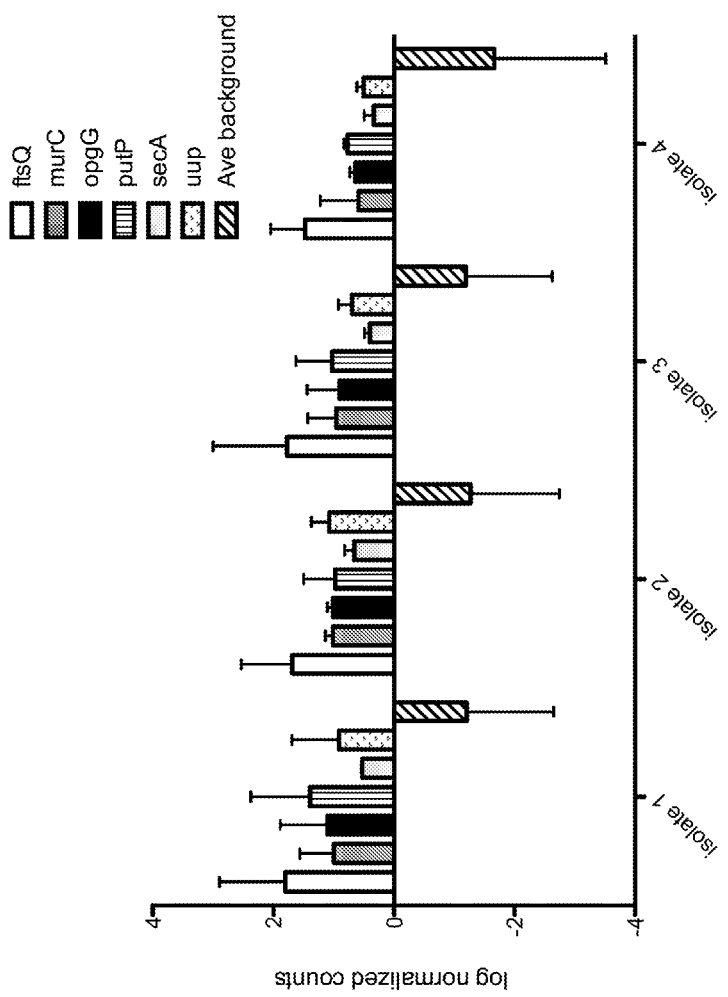
FIG. 3 is a bar graph showing positive identification of *E. coli* clinical isolates. Using probes designed to six *E. coli* genes (ftsQ, murC, opgG, putP, secA, and uup), four clinical isolates were positively identified as *E. coli*. Each value represents average and standard deviation of 4 to 6 replicates.
Figure 4:
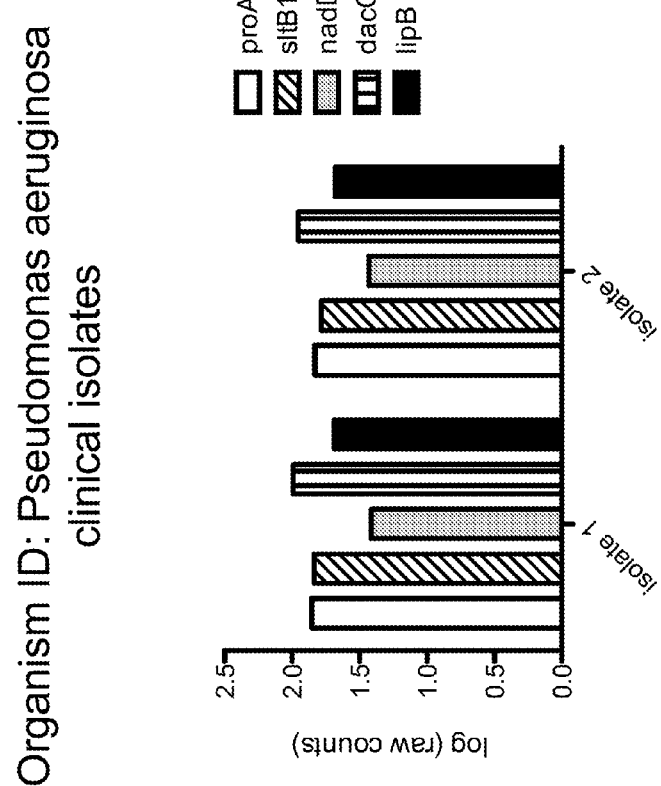
FIG. 4 is a bar graph showing positive identification of *Pseudomonas aeruginosa* clinical isolates. Using probes designed to five *P. aeruginosa* genes (proA, sltB1, nadD, dacC, and lipB), two clinical isolates were positively identified as *P. aeruginosa*.
Figure 5:
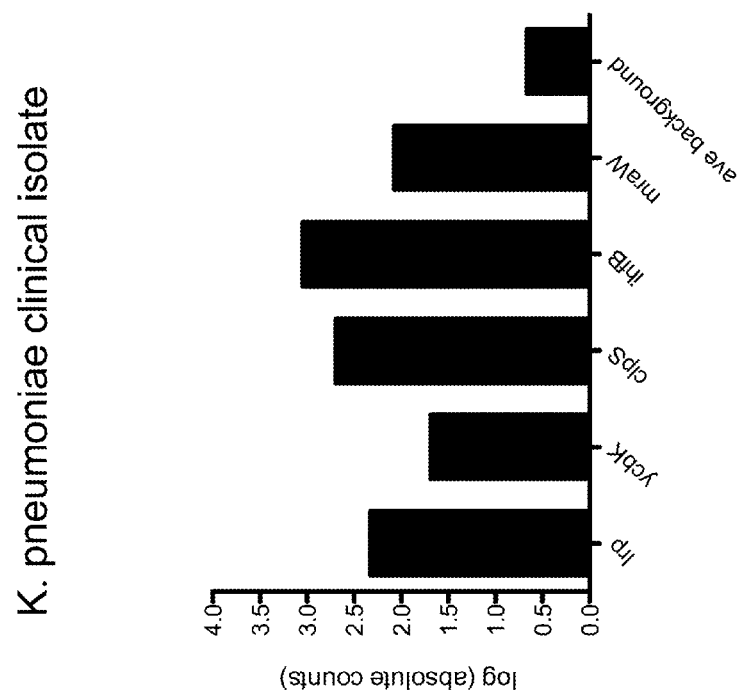
FIG. 5 is a bar graph showing positive identification of a *Klebsiella pneumoniae* clinical isolate. Using probes designed to five *K. pneumoniae* genes (lrp, ycbK, clpS, ihfB, mraW) a clinical isolate was positively identified.
Figure 6:
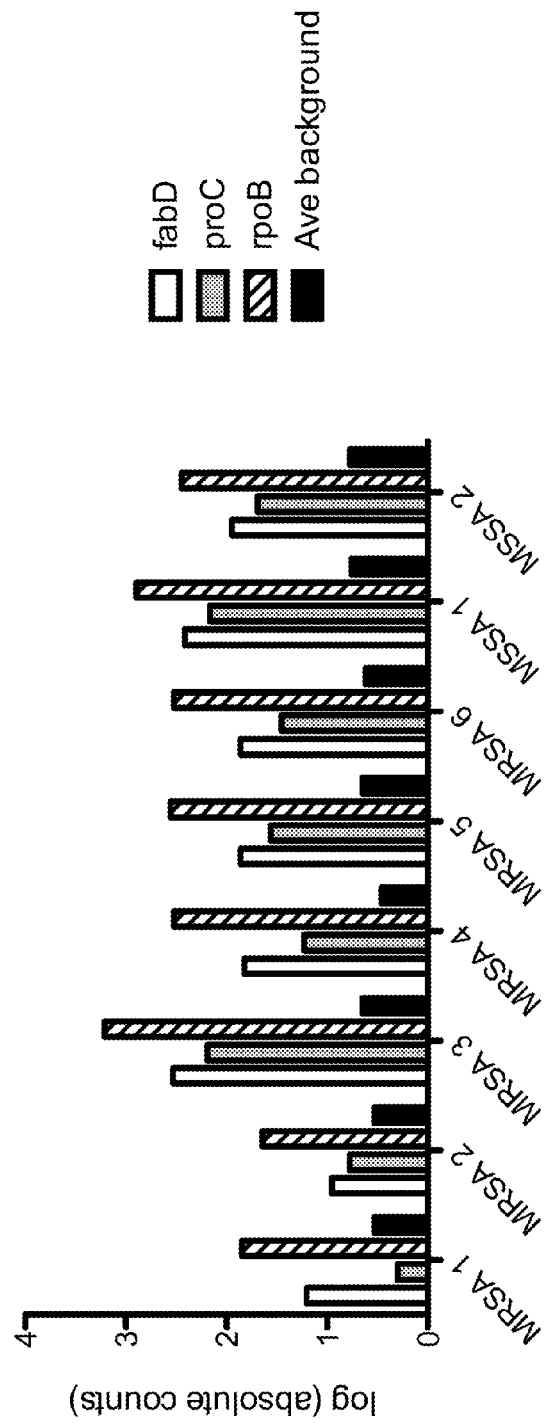
FIG. 6 is a bar graph showing positive identification of *S. aureus* clinical isolates. Using probes designed to three *S. aureus* genes (proC, rpoB, and fabD), four clinical isolates were positively identified.
Figure 7:
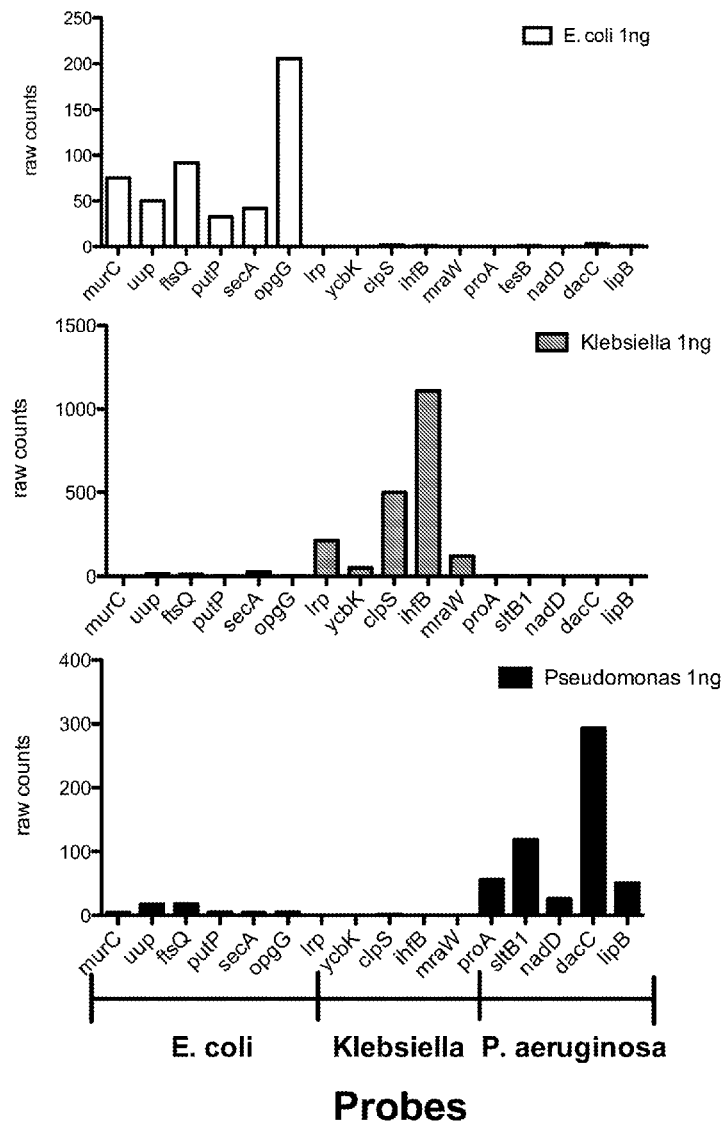
FIG. 7 is a panel of three bar graphs showing pathogen identification using pathogen specific probes.

*Escherichia coli, Pseudomonas aeruginosa, Klebsiella pneumoniae*, and *Staphylococcus aureus*. Unique coding sequences in *Escherichia coli, Pseudomonas aeruginosa, Klebsiella pneumoniae, Staphylococcus aureus*, and *Enterococcus faecalis* were identified (Table 2) and used to positively identify these organisms (FIGS. 3-6). Clinical isolates were grown in LB media at 37° C. to log phase. Five microliters of each culture were then added to 100 microliters of guanidinium isothiocyanate lysis buffer (RLT buffer, Qiagen) and vortexed for 5 seconds. Four microliters of each lysate preparation were then used in the nCounter™ System assay according to the manufacturer's standard protocol for lysates. Criteria for identification were counts for all five (for *P. aeruginosa* or *K. pneumoniae*) or six (for *E. coli*) organism identification probes at least two-fold above the average background (the average of counts for all organism identification probes for the other two organisms). To compare between replicates, counts were normalized to counts of proC. Using the organism identification probes described in Table 2, four *E. coli* clinical isolates were correctly identified using probes designed to six *E. coli* genes (ftsQ, murC, opgG, putP, secA, and uup) (FIG. 3). Two clinical isolates were correctly identified as *P. aeruginosa* using probes designed to five *P. aeruginosa* genes (proA, sltB1, nadD, dacC, and lipB) as shown in FIG. 4. As shown in FIG. 5, probes designed to five *K. pneumoniae* genes (lrp, ycbK, clpS, ihfB, and mraW) positively identified a *K. pneumoniae* clinical isolate. Using probes designed to three *S. aureus* genes (proC, rpoB, and fabD), four clinical isolates were positively identified (FIG. 6). Cut-off criteria for identification were that counts for rpoB and fabD are at least two-fold above the average background (the average of counts for all organism identification probes for *E. coli, P. aeruginosa*, and *K. pneumoniae*).

Figure 22:
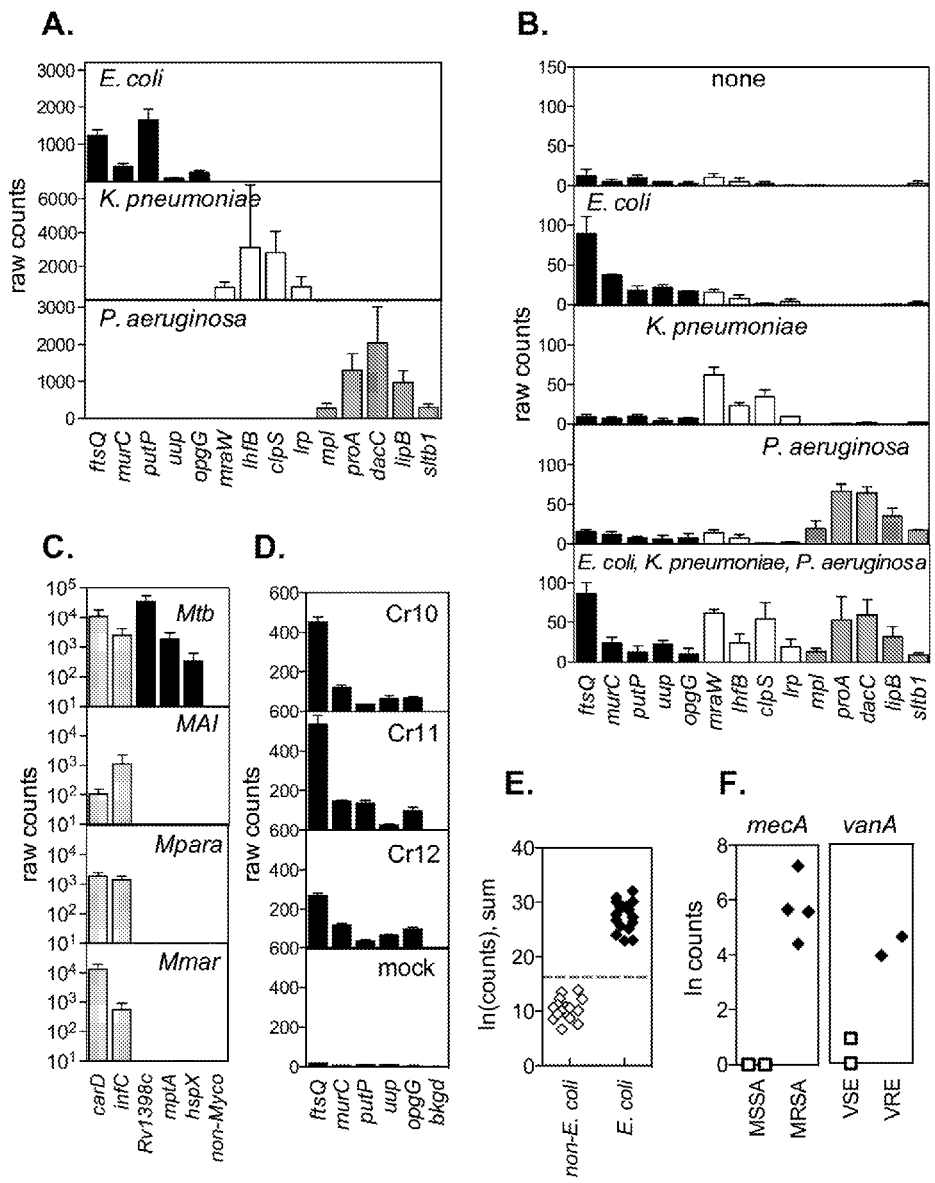
FIG. 22 is a panel of bar and scatter plots showing positive identification of bacterial species directly from culture or patient specimens. Bacterial samples were analyzed with NanoString™ probes designed to detect species-specific transcripts. Y-axis: transcript raw counts; X-axis: gene name. Probes specific for *E. coli* (black), *K. pneumoniae* (white), *P. aeruginosa* (grey). Error bars reflect the standard deviation of two biological replicates. (A) Detection from culture of Gram-negative bacteria. (B) Detection within mixed culture (*Providencia stuartii, Proteus mirabilis, Serratia marcescens, Enterobacter aerogenes, Enterobacter cloacae, Morganella morganii, Klebsiella oxytoca, Citrobacter freundii*). (C) Genus- and species-specific detection of mycobacteria in culture. *M. tuberculosis* (Mtb), *M. avium* subsp. *intracellulare* (MAI), *M. paratuberculosis* (Mpara), and *M. marinum* (Mmar). Genus-wide probes (grey), *M. tuberculosis*-specific probes (black). (D) Detection of *E. coli* directly from clinical urine specimens. (E) Statistical determination of identity of *E. coli* samples in comparison with non-*E. coli* samples. Counts for each probe were averaged, log transformed and summed. (F) Detection of mecA mRNA, which confers resistance to methicillin in Staphylococci, and vanA mRNA, which confers resistance to vancomycin in Enterococci. Each point represents a different clinical isolate.

On average, 4-5 sequences for each organism were included in the larger pool to obtain desired levels of specificity. Using this technology, each of these three organisms were detected, identified, and distinguished in axenic culture and in a complex mixture including eight additional Gram-negative pathogens by directly probing crude lysates (FIGS. 22A and 22B).

TB. Probes to Rv1641.1 and Rv3583c.1 detect highly abundant transcripts in *M. tuberculosis* (reference 8) and will detect orthologous transcripts in *M. avium*, and *M. avium* subsp. *paratuberculosis*, thus can be used for detection of any of these three species. Further, probes to three TB genes (Rv1980c.1, Rv1398c.1, and Rv2031c.1) can be used to differentially identify *M. tuberculosis*, i.e., they will not detect *M. avium* or *M. avium* subsp. *paratuberculosis*. Probes to MAP_2121c.1, MAV_3252.1, MAV_3239.1, and MAV_1600.1 can be used to detect *M. avium* or *M. avium* subsp. *paratuberculosis*, but will not detect *M. tuberculosis*. Thus, maximum sensitivity is achieved with the Rv1980c and Rv3853 probes, while the probes to Rv1980c.1, Rv1398c.1, and Rv2031c.1, and MAP_2121c.1, MAV_3252.1, MAV_3239.1, and MAV_1600.1, enable the distinction between *M. tuberculosis* infection and *M. avium* or *M. avium* subsp. *paratuberculosis* infection.

Probes were designed to genes both conserved throughout the mycobacterium genus and specific only to *Mycobacterium tuberculosis*. The pan-mycobacterial probes recognized multiple species, while the *M. tuberculosis* probes were highly specific (FIG. 22C).

*Staphylococcus aureus* and *Stenotrophomonas maltophilia*

Using the organism identification probes described Table 2, three *S. aureus* isolates were correctly identified using probes designed to five *S. aureus* genes (ileS, ppnK, pyrB, rocD, and uvrC) (FIG. 30). Similarly, three *Stenotrophomonas maltophilia* isolates were correctly identified using probes designed to six *S. maltophilia* genes (clpP, dnaK, purC, purF, sdhA, and secD) (Table2; and FIG. 31).

Example 2

Sensitivity of the Methods

As shown in FIGS. 7-10, the present methods are specific for each pathogen of interest and sensitive to detect less than 100 cells in clinical samples, e.g., blood and urine.

RNA isolated from each of the three pathogens (1 ng) was probed with a 24 gene probe set (FIG. 7). *E. coli* genes, left; *K. pneumoniae* genes, middle; and *P. aeruginosa* genes, right. *E. coli* RNA, top. *K. pneumoniae*, middle; and *P. aeruginosa*, bottom. The y-axis shows number of counts for each gene as detected by using digital gene expression technology. RNA from each of the organisms shows distinct expression signatures that allow facile identification of each of the pathogens.

Figure 8:
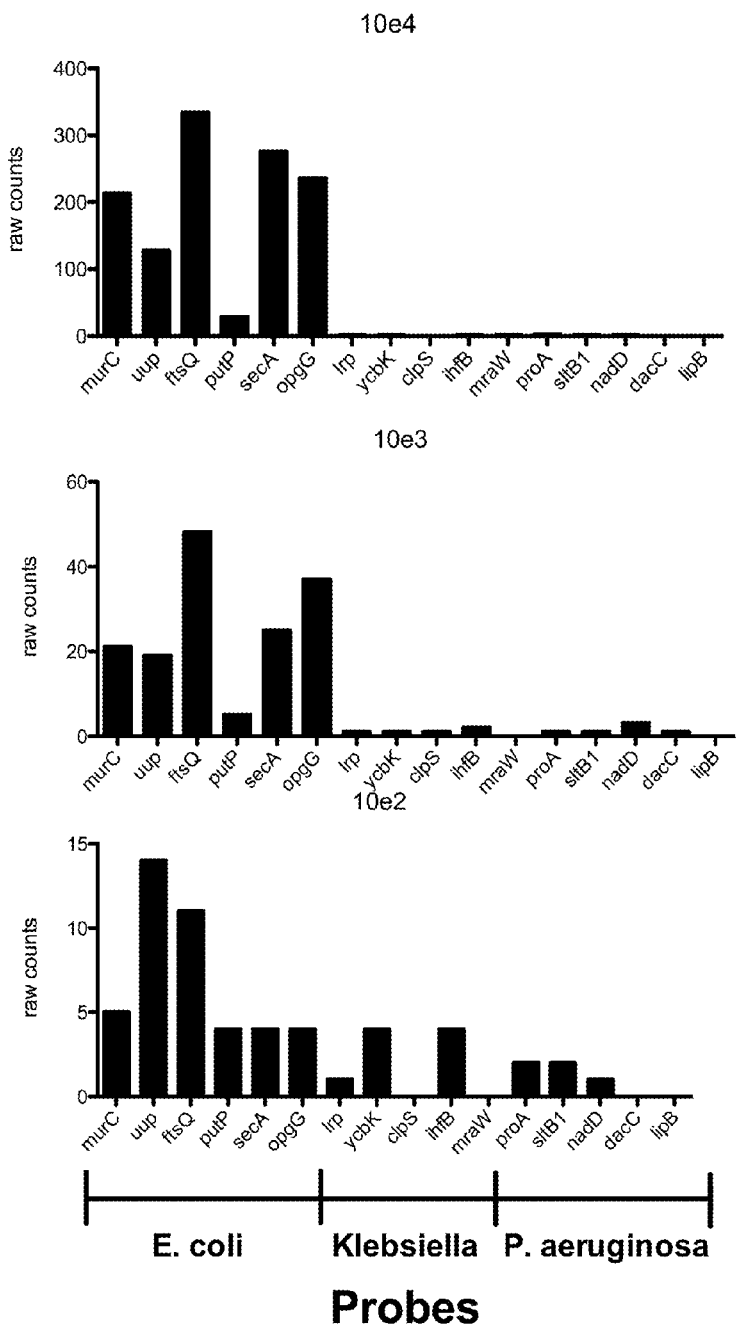
FIG. 8 is a panel of three bar graphs showing pathogen identification sensitivity.

This 24 gene probe set was used to probe crude *E. coli* lysates from 10,000 cells, 1000 cells, and 100 cells (FIG. 8). The distinct *E. coli* expression signature could be distinguished for down to 100 cells.

Figure 9A:
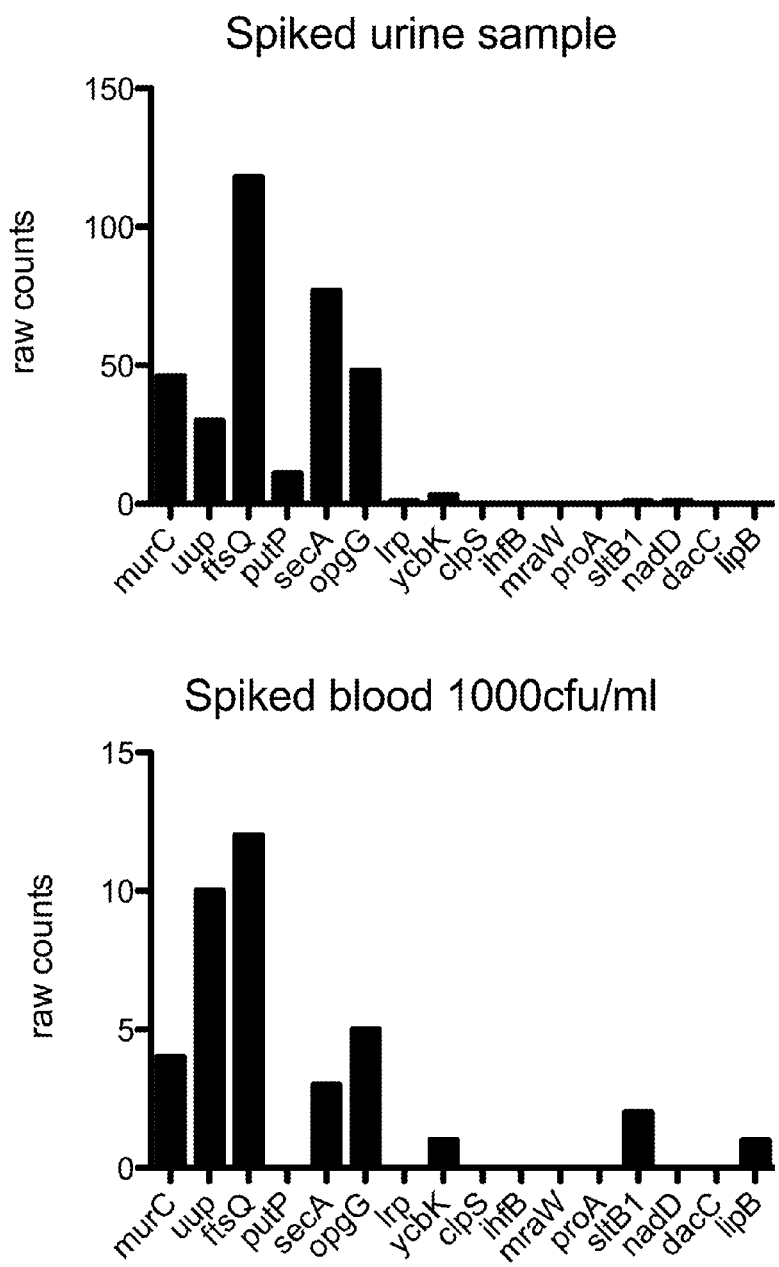
FIGS. 9A and 9B are panels of three bar graphs showing pathogen identification from simulated clinical samples.
Figure 9B:
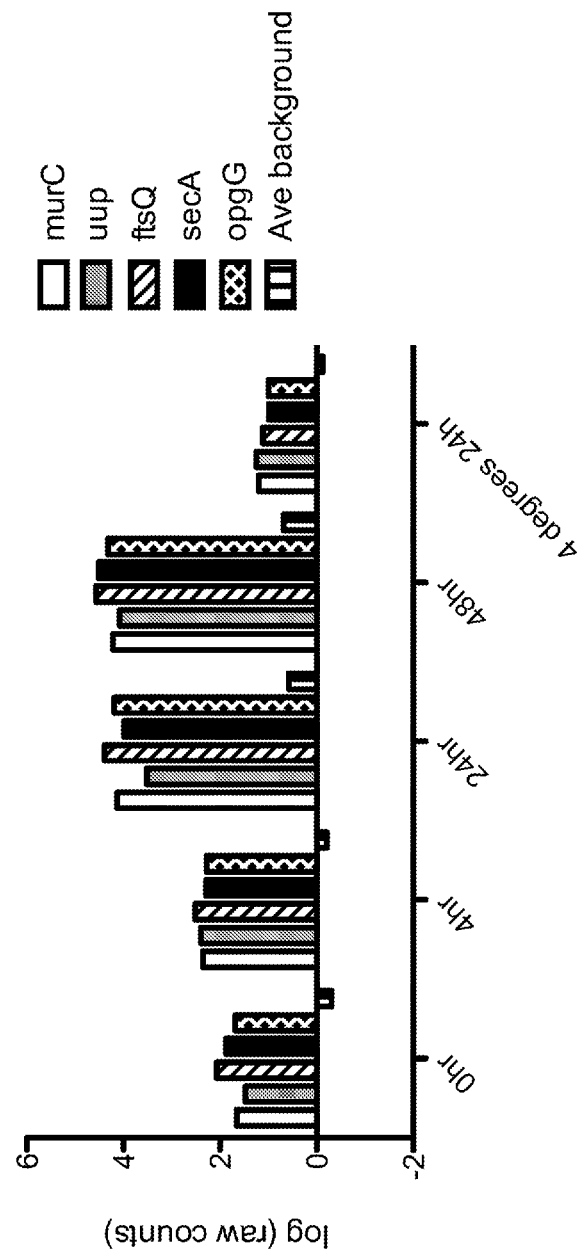

Clinical samples were simulated in spiked urine and blood samples. In the spiked urine sample, a urine sample was spiked with 105 *E. coli* bacteria/mL of urine. The sample was refrigerated overnight at 4° C. and then the crude bacterial sample was lysed and probed with the 24-gene probe set used for the Gram negative bacteria to identify *E. coli* (FIGS. 9A, top panel, and 9B). Blood was spiked with 1000 cfu/ml and also detected with the 24-gene probe set (FIG. 9A, bottom panel).

Figure 10:
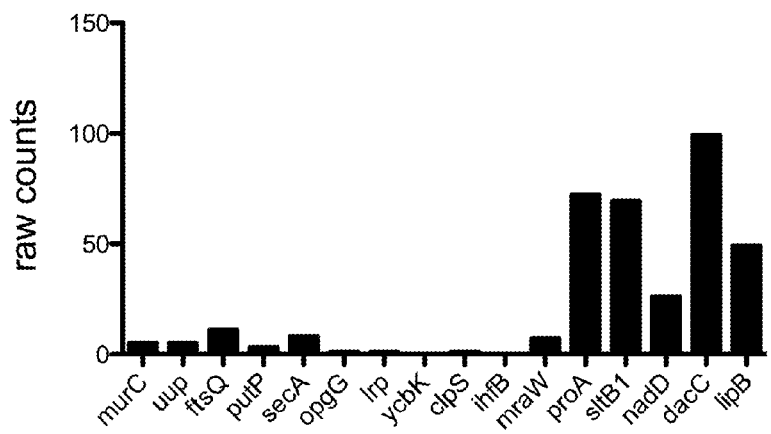
FIG. 10 is a panel of two bar graphs showing identification of two clinical isolates of *P. aeruginosa*.
Figure 10:
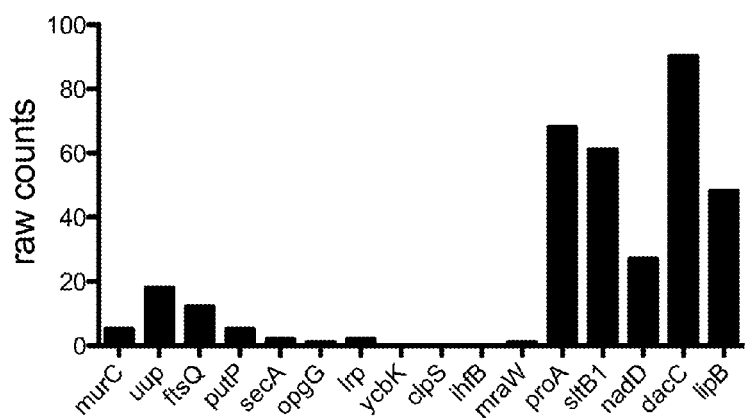

Two clinical isolates of *P. aeruginosa* (obtained from Brigham and Women's clinical microbiology lab) were probed with the 24-gene probe set used for the Gram negative bacteria to demonstrate that the gene set is able to identify clinical diverse strains of the same bacterial genus (FIG. 10).

Identification of *Escherichia coli* directly in urine samples. *E. coli* strain K12 was grown in LB media at 37° C. to late log phase culture. Bacteria were then added to urine specimens from healthy donors to a final concentration of 100,000 cfu/ml (as estimated by $OD_{600}$). Urine samples were then left at room temperature for 0 hours, 4 hours, 24 hours, or 48 hours or placed at 4° C. for 24 hours. 1 ml of spiked urine was centrifuged at 13,000×g for 1 minute. The supernatant was removed; pellets were resuspended in 100 microliters of LB media. Bacteria were treated with Bacteria RNase Protect (Qiagen), and then lysed in guianidinium isothiocyanate lysis buffer (RLT buffer, Qiagen). Lysates were used in the nCounter™ System assays per manufacturer's protocol.

Aliquots of patient urine specimens were directly assayed to detect *E. coli* transcripts in urinary tract infections (FIG. 22D). To condense the signals from multiple transcripts into a single metric that assesses the presence or absence of an organism, the raw counts from each probe were log transformed and summed. When applied to a set of 17 clinical *E. coli* isolates, every isolate was easily differentiated from a set of 13 non-*E. coli* samples (Z score>6.5 relative to non-*E. coli* controls, FIG. 22E).

Example 3

Drug Sensitivity of a Pathogen

Figure 11:
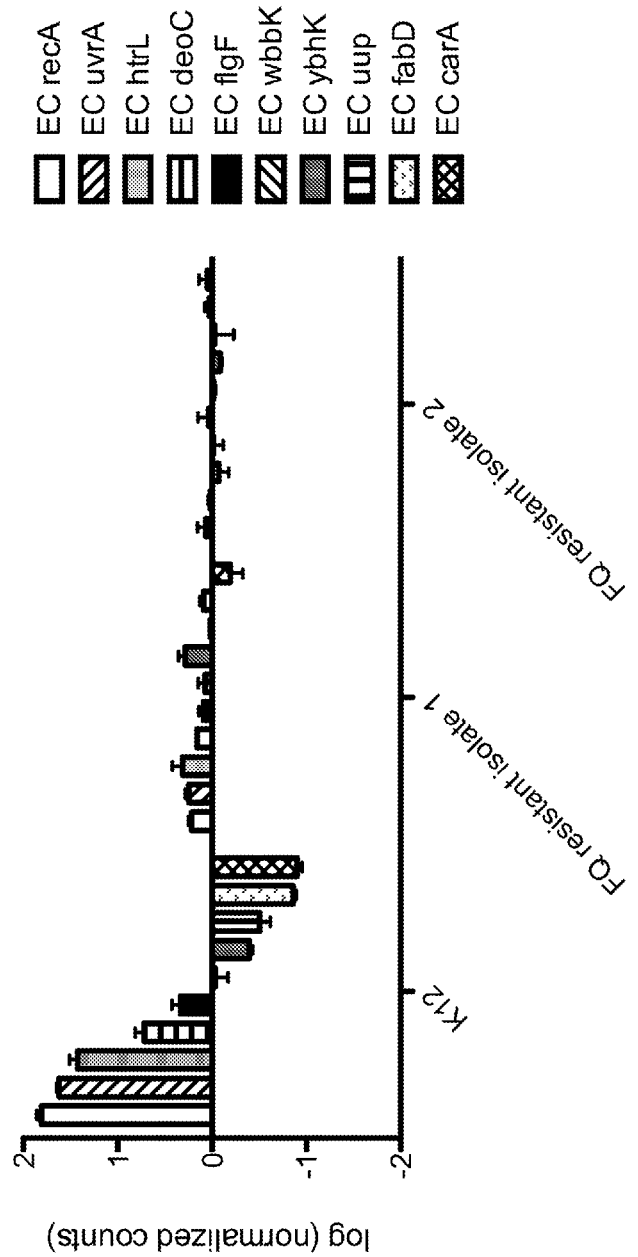
FIG. 11 is a bar graph showing the identification of fluoroquinolone resistance in *E. coli*.
Figure 12:
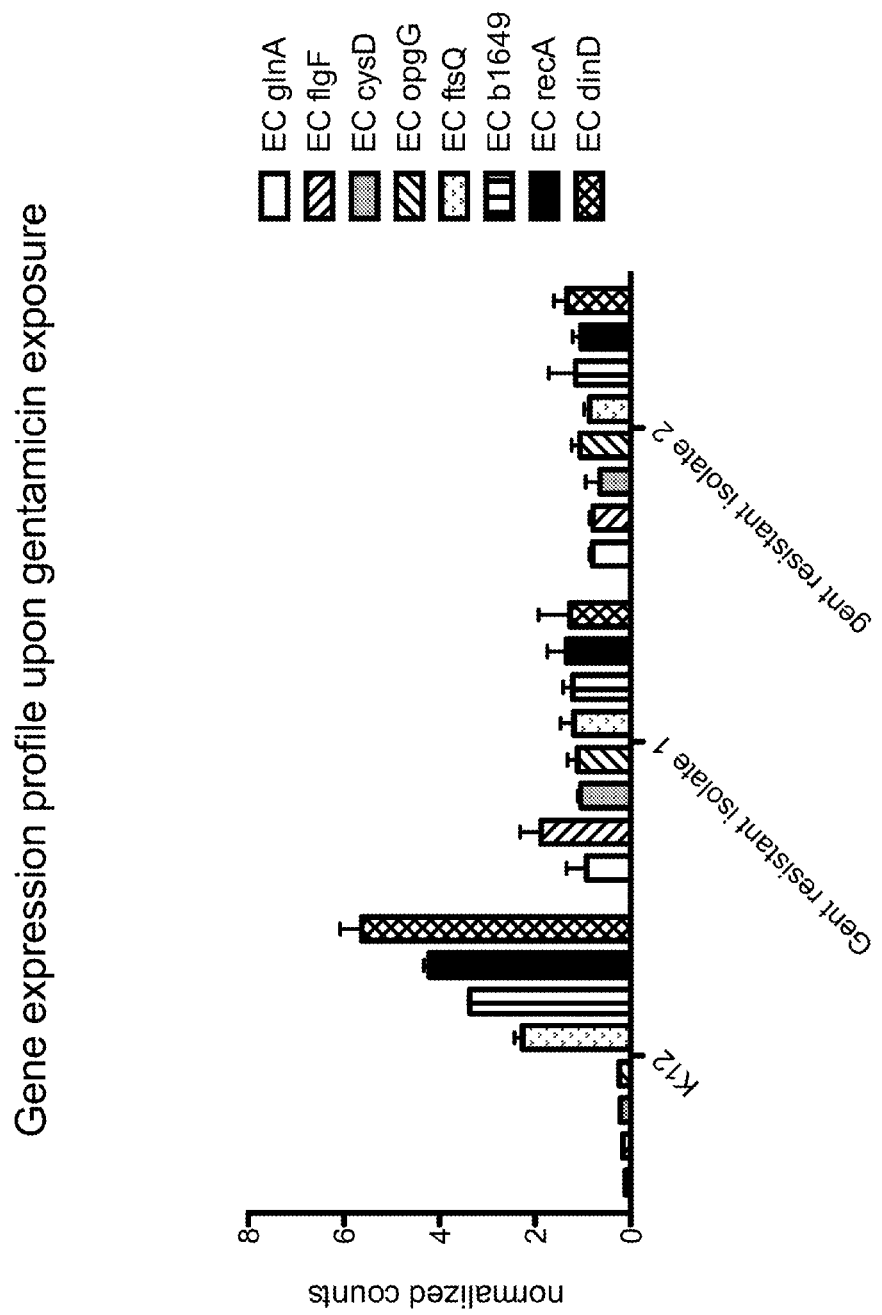
FIG. 12 is a bar graph showing the identification of aminoglycoside resistance in *E. coli*.

Identification of fluoroquinolone and aminoglycoside resistance in *Escherichia coli*. Using published expression array data for *E. coli* upon exposure to fluoroquinolones and aminoglycosides (Sangurdekar D P, Srienc F, Khodursky A B. A classification based framework for quantitative description of large-scale microarray data. *Genome Biol* 2006; 7(4):R32) sets of genes expected to be significantly down- or up-regulated upon exposure to fluoroquinolones and aminoglycosides were chosen. The pan-sensitive lab strain (K12), fluoroquinolone-resistant clinical isolates 1 and 2, and gentamicin-resistant clinical isolates (E2729181 and EB894940) were grown in LB media to log phase at 37° C. A 2 ml aliquot of each culture was taken, and antibiotics were added to those aliquots at a final concentration of 8 µg/ml ciprofloxacin or 128 µg/ml gentamicin. Cultures were incubated at 37° C. for 10 minutes. Five microliters of each culture was added to 100 microliters of guanidinium isothiocyanate lysis buffer and vortexed for 5 seconds. Lysates were used in the nCounter™ System assays per manufacturer's protocol. Counts were normalized to counts of proC; again proC appeared to be most comparable between experiments; fold induction for each gene was determined by comparing counts in the presence and absence of antibiotic exposure. There were clear signals from 9 probes (carA, deoC, flgF, htrL, recA, uvrA, ybhK, uup, and fabD) that show induction or repression in the drug sensitive K12 strain that distinguishes it from the two resistant clinical isolates (FIG. 11). A tenth probe, wbbK, was neither induced nor repressed, offering a useful comparison for genes with changes expression. Similarly, probes to eight genes show that these genes are either repressed (flgF, cysD, glnA, opgG) induced (ftsQ, b1649, recA, dinD) in the drug sensitive K12 strain that distinguishes it from the two resistant clinical isolates (FIG. 12)

Figure 13:
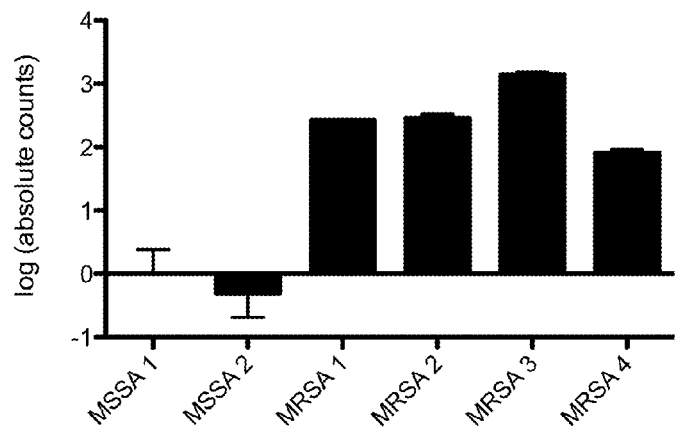
FIG. 13 is a bar graph showing the identification of methicillin resistance in *S. aureus*.

Identification of methicillin resistance in *Staphylococcus*. Six *S. aureus* clinical isolates were grown to log phase at 37° C. in LB media. A 2 ml aliquot of each culture was then taken; cloxacillin was added to a final concentration of 25 µg/ml. Cultures were incubated at 37° C. for 30 minutes. Five microliters of each culture was added to 100 microliters of guanidinium isothiocyanate lysis buffer and vortexed for 5 seconds. Lysates were used in the nCounter™ System assays per manufacturer's protocol. Using two independent probes (Table 2), expression of mecA was identified in the four isolates known to be methicillin-resistant. In contrast, there was no detectable mecA expression in the two isolates known to be methicillin-sensitive and minimal mecA expression in the absence of cloxacillin (FIG. 13).

Figure 14:
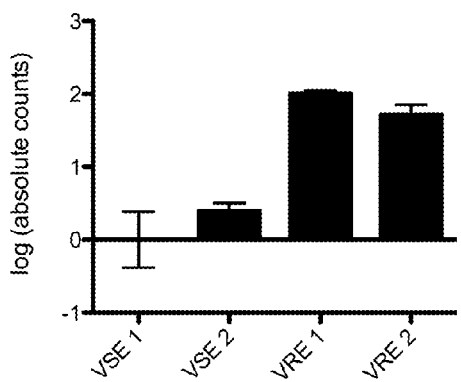
FIG. 14 is a bar graph showing the identification of vancomycin resistance in *Enterococcus*.
Figure 15:
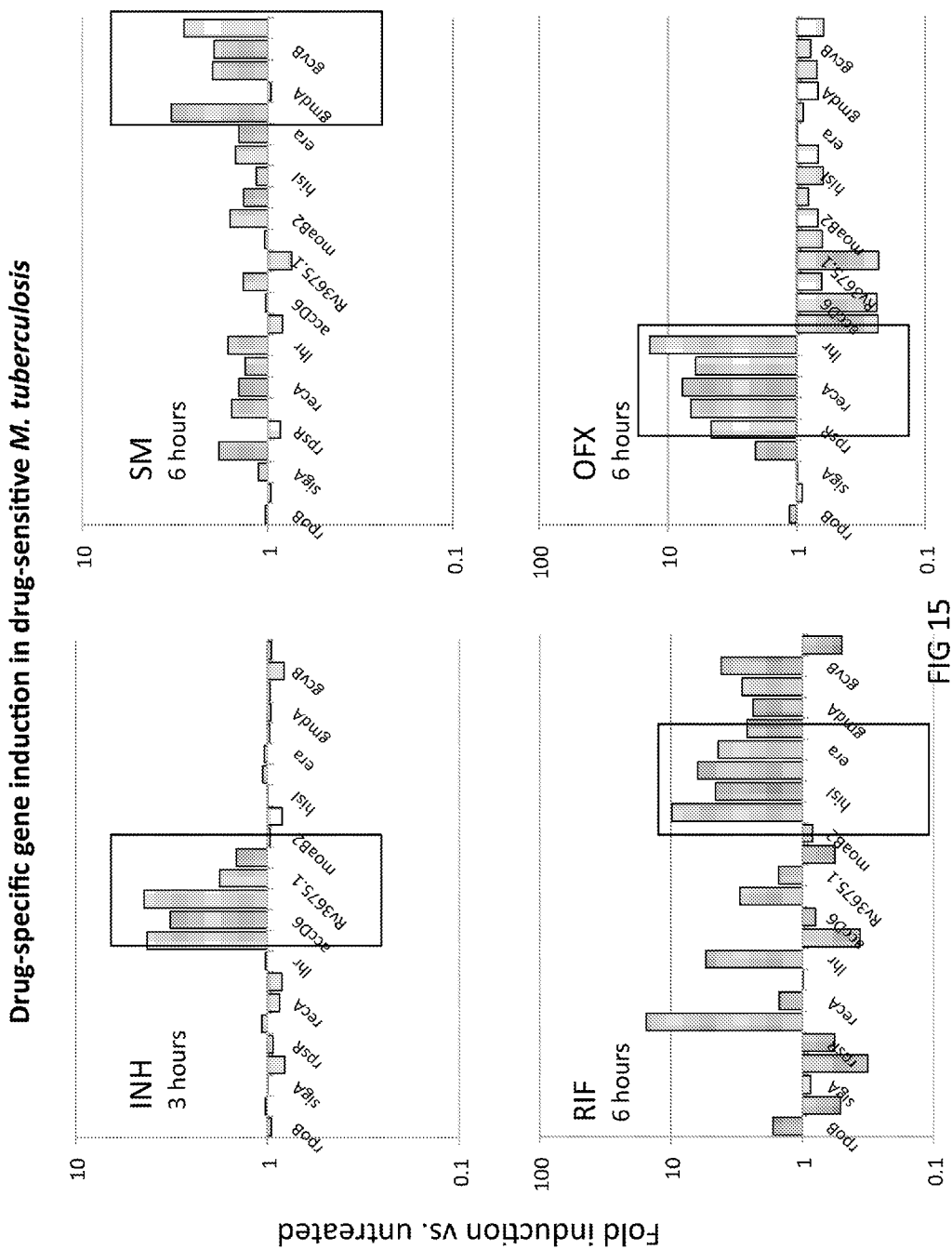
FIG. 15 is a panel of four bar graphs showing drug-specific gene induction in drug-sensitive *M. tuberculosis*.

Identification of vancomycin resistance in *Enterococcus*. Four *Enterococcus* clinical isolates were grown in LB media to log phase at 37° C. A 2 ml aliquots were taken; vancomycin was added to a final concentration of 128 µg/ml. Cultures were incubated at 37° C. for 30 minutes. Five microliters of each culture was added to 100 microliters of guanidinium isothiocyanate lysis buffer and vortexed for 5 seconds. Lysates were used in the nCounter™ System assays per manufacturer's protocol. Using two independent probes (Table 2), expression of vanA was identified in the two isolates known to be vancomycin resistant. In contrast, there was no detectable vanA expression in the two isolates known to be vancomycin sensitive and minimal expression of vanA in the absence of vancomycin (FIG. 14). There was no detectable vanB expression in any of the four isolates.

Beyond the detection of transcripts for organism identification, detection of genes encoded on mobile genetic elements can provide greater genomic detail about a particular isolate. For example, bacterial isolates were probed for mecA mRNA, which confers resistance to methicillin in Staphylococci, and vanA mRNA, which confers resistance to vancomycin in Enterococci. In both cases, relevant transcripts were detected that allowed for rapid identification of MRSA and vancomycin-resistant *Enterococcus* (VRE) (FIG. 22F). Thus, direct detection of RNA is able to detect known resistance elements. In addition, this approach is able to discriminate isolates by other genetic factors, such as virulence factors acquired through horizontal genetic exchange in food-borne pathogens, i.e., Shiga toxin in Enterohemorrhagic or Shigatoxigenic *E. coli*.

Identification of drug resistance in TB. A 24 gene probe set was identified from published gene expression data to identify an expression signature that would allow identification of expression changes of drug sensitive TB upon exposure to different antibiotics, including isoniaid, rifampin, streptomycin, and fluoroquinolones (FIGS. 15-18). The magnitude of induction or repression after drug exposure is shown in Table 3.

Log phase *M. tuberculosis* cells at $A_{600}$ 0.3 were grown in inkwell bottles (10 ml volume, parallel cultures) in the presence of one of four different drugs (isoniazid, 0.4 µg/ml; streptomycin, 2 µg/ml; ofloxacin, 5 µg/ml; rifampicin 0.5 µg/ml). At the indicated time after the initiation of drug treatment (FIG. 15), cultures were harvested by centrifugation (3000×g, 5 minutes), resuspended in 1 ml Trizol, and bead beaten (100 nm glass beads, max speed, two one-minute pulses). Chloroform (0.2 ml) was added to the samples, and following a five minute centrifugation at 6000×g, the aqueous phase was collected for analysis.

Samples were diluted 1:10 and analyzed using NanoString™ probeset described in Table 2 per the manufacturer's protocol. The relative abundance of each transcript is first calculated by normalizing to the average counts of three housekeeping genes (sigA, rpoB, and mpt64), and then the data is plotted as a fold change relative to samples from untreated controls. The boxes indicate probes that were selected based on previous evidence of drug-specific induction (Boshoff et al., J Biol. Chem. 2004, 279(38):40174-84.)

Figure 16:
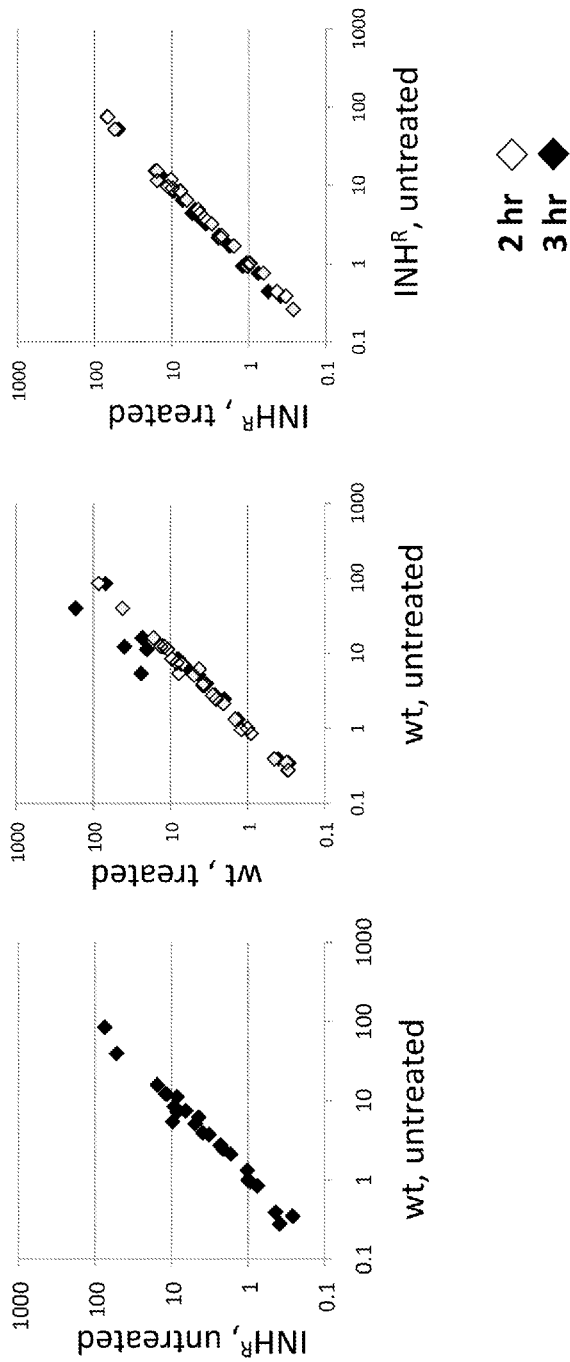
FIG. 16 is panel of three scatter plots comparing isoniazid sensitive and resistant TB strains. Each dot represents one of the 24 gene probes. The axes report number of transcripts as measured by digital gene expression technology (NanoString™). Left—Comparison of expression in isoniazid resistant and isoniazid sensitive strains in the absence of drug treatment. Middle—Comparison of expression in drug treated vs. drug untreated isoniazid sensitive strain. Right—Comparison of expression in drug treated vs. drug untreated isoniazid resistant strain.

The drug resistant TB strain shows no expression signature induction upon exposure to isoniazid, in contrast to a drug sensitive strain, which clearly shows induction of an expression signature upon isoniazid exposure (FIG. 16). Three scatter plots comparing isoniazid sensitive and resistant TB strains are shown in FIG. 16, with each dot representing one of the 24 gene probes. The axes report number of transcripts as measured by digital gene expression technology (NanoString™). Left—Comparison of expression in isoniazid resistant and isoniazid sensitive strains in the absence of drug treatment. Middle—Comparison of expression in drug treated vs. drug untreated isoniazid sensitive strain. Right—Comparison of expression in drug treated vs. drug untreated isoniazid resistant strain.

Figure 17:
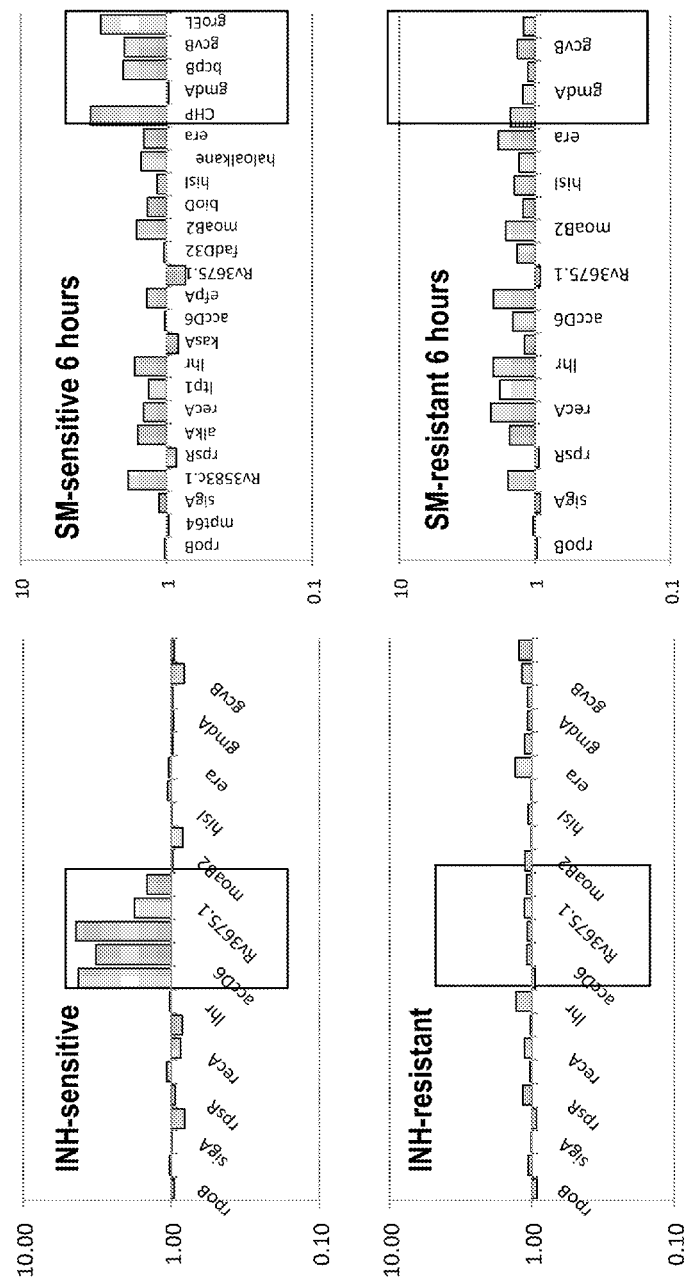
FIG. 17 is a panel of four bar graphs comparing the transcriptional responses of drug-sensitive and drug-resistant *M. tuberculosis* using NanoString™. (A) Strain A50 (INH-R) was treated with INH (0.4 µg/ml) as described herein. (B) The SM-R clone S10 was treated with 2 µg/ml streptomycin.
Figure 18:
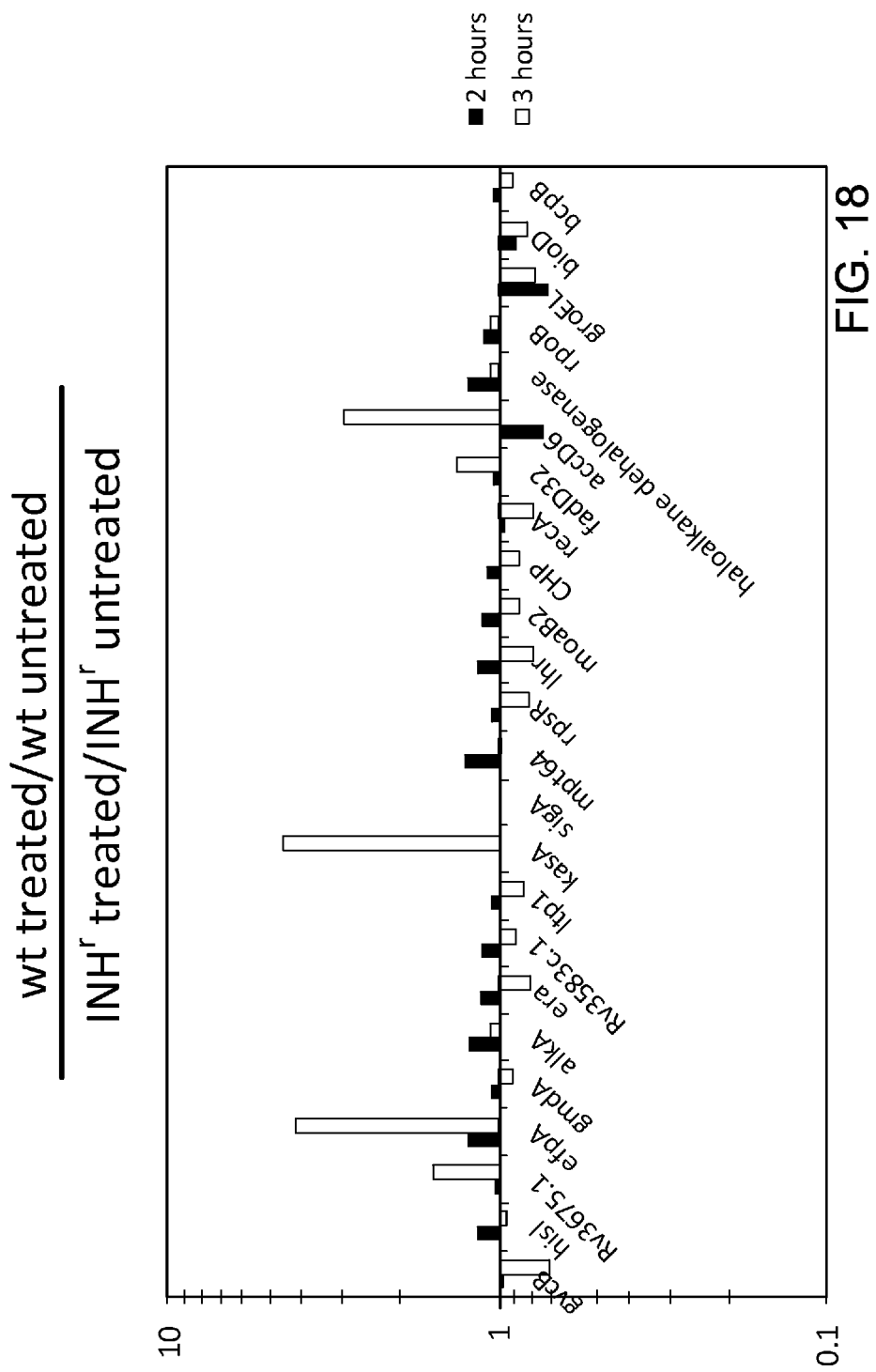
FIG. 18 is bar graph showing differential gene induction in sensitive vs. resistant TB strain. The ratio of expression of each gene in INH sensitive (wt) cells treated with INH/untreated cells is divided by the expression of each gene in INH resistant cells treated with INH/untreated cells.

Different sets of genes are induced in drug-sensitive *M. tuberculosis* depending on the drug as seen in FIG. 17. The transcriptional responses of drug-sensitive and drug-resistant *M. tuberculosis* (A) Strain A50 (INH-R) treated with INH (0.4 µg/ml) as described herein. (B) The SM-R clone S10 was treated with 2 µg/ml streptomycin. Differential gene induction can be measured by digital gene expression of the TB 24 gene probe set to reveal a clear signature and allow identification of drug sensitivity (FIG. 18).

Three housekeeping genes, mpt64, rpoB, and sigA, were used for normalization. For each experimental sample, the raw counts for the experimental genes were normalized to the average of the raw counts of these three housekeeping genes, providing a measure of the abundance of the test genes relative to the control genes. Induction or repression is defined as a change in these normalized counts in drug-exposed samples as compared to non-drug-exposed samples. Using this methodology, the following genes were found to be induced or repressed in drug-sensitive TB after exposure to isoniazid, rifampin, fluoroquinolones, and streptomycin.

Isoniazid: For drug-dependent induction: kasA, fadD32, accD6, efpA, and Rv3675.1.

Rifampin: For drug-dependent induction: bioD, hisI, era, and Rv2296.

Fluoroquinolones: For drug-dependent induction: rpsR, alkA, recA, ltp1, and lhr; for drug-dependent repression: kasA and accD6.

Streptomycin: For drug-dependent induction: CHP, bcpB, gcvB, and groEL.

Example 4

A Phenotypic Expression Signature-Based Test to Identify Drug Sensitive and Resistant TB Using Digital Gene Expression with Molecular Barcodes This example describes a phenotypic expression-signature-based test for the diagnosis of TB in sputum and rapid determination of resistance profile. The method is based on detection of genes whose expression profiles will uniquely detect TB and distinguish drug resistant and sensitive strains, with the creation of a probe set of bar-coded, paired molecular probes. The choice of genes was determined through bioinformatic analysis of expression profile data obtained using microarrays under a variety of growth conditions, including TB in axenic culture (both replicating and non-replicating states), TB in cell cultured macrophages, and TB spiked in sputum.

A. Define Signature for Identification of TB

A set of molecular probes have been identified that will specifically hybridize to mRNA from both replicating and non-replicating TB. The probes are specific for mRNA that is highly abundant under all growth conditions and is conserved across all TB strains. While unique DNA sequences have been previously defined to identify TB recognizing 16S rRNA (Amplicor, Roche) or the IS6110 region (Gen-probe), these defined regions do not have the optimal characteristics required for signatures in digital gene expression. The 16S rRNA is not sufficiently divergent among mycobacterial species that could distinguish between the different species using 50-base oligomer gene probes, which can tolerate low levels of genetic variability due to their length. The IS6110 region of the genome is not expressed at high enough levels under all growth conditions that would allow it to be used it as a robust signal to identify TB. Thus, an expression signature that will allow identification of TB from other mycobacterial species is described.

i. Bioinformatic gene analysis for conserved TB genes. Unique expression signatures for the detection of TB over other mycobacteria species have been defined. In general, the optimal genes for inclusion in a signature will fulfill the criteria of 1. having high expression levels (high mRNA copy number) to increase sensitivity, 2. being highly conserved across all TB strains as well as having highly conserved sequence, and 3. being highly specific for TB genome over all other mycobacteria species. Such genes were identified using a bioinformatic analysis of conserved genes in the available TB genomes that are not present in all other sequenced mycobacteria species (i.e., *M. marinum, M. avium-intracellulaire, M. kansaii, M. fortuitum, M. abscessus*). Over 40 TB genomes from clinically isolated strains that have been sequenced at the Broad Institute are available for analysis.

ii. Expression profile analysis of mRNA levels of candidate genes. A second criterion for selection of molecular probes for the detection of TB bacilli in sputum is that they hybridize to highly abundant, stable mRNAs to allow maximum sensitivity. Such mRNAs are anticipated to correspond to essential housekeeping genes. Genes have been selected using a combination of bioinformatic analysis of existing, publicly available expression data in a database created at the Broad Institute and Stanford University (tbdb.org) and experimental expression profiles on TB strain H37Rv using expression profiling to confirm a high level of expression of candidate genes under conditions permissive for replication (logarithmic growth) and non-replication induced by carbon starvation, stationary phase, and hypoxia. Expression profiling experiments on H37Rv are performed using a carbon starvation model of TB that has been established (starvation for 5 weeks in 7H9/tyloxapol), stationary phase growth, and the Wayne model for anaerobic growth (slowly agitated cultures in sealed tubes). Solexa/Illumina sequencing is used to determine expression profiles by converting mRNA to cDNA and using sequencing to count cDNA molecules. This quantitative method for identifying expression levels is more likely to reflect levels obtained using digital gene expression than microarray data and is a method that has been established with the Broad Institute Sequencing Platform. It is possible to multiplex 12 samples per sequencing lane given 75 bp reads and 10 million reads per lane.

iii. Probe selection of expression signature identifying TB. Because the digital gene expression technology is based on the hybridization of two 50 nucleotide probes to the mRNA of interest, two 50 base pair regions in the genes are identified from (Ai) and (Aii) that are unique within the genome to minimize non-specific hybridization and that contain minimal polymorphisms as evidenced from sequenced TB genomes. The probes are selected bioinformatically to fit within a 5 degree melting temperature window and with minimal mRNA secondary structure. The probes are tested against mRNA isolated from replicating and non-replicating TB (including multiple strains i.e., H37Rv, CDC1551, F11, Erdman), *M. marinum, M. avium-intracellulaire, M. kansaii,* and *M. fortuitum* to confirm the specificity of the entire probe set using available technology. Probes may be selected for these other mycobacterial species, which will allow for identification of these pathogens from sputum as well. The ability to identify intracellular bacilli is tested in a macrophage model of infection, to demonstrate the ability to detect TB mRNA in the presence of host mRNA. Finally, the sensitivity of the assay was determined by titrating down the number of TB bacilli (and thus mRNA present in cell lysates) in the sample tested. All experiments using digital gene expression is confirmed using quantitative RT-PCR against the same gene set. Improvement and refinement of the set will occur in an iterative manner.

B. Define Signature to Distinguish Sensitive and Resistant TB

A set of molecular probes that hybridizes to mRNAs that are specifically induced upon exposure to each individual TB drug has been identified, allowing a profile to be obtained that distinguishes drug sensitive and resistant strains. Signatures have been determined for exposure to isoniazid, rifampin, ethambutol, streptomycin, and moxifloxacin.

Figure 19:
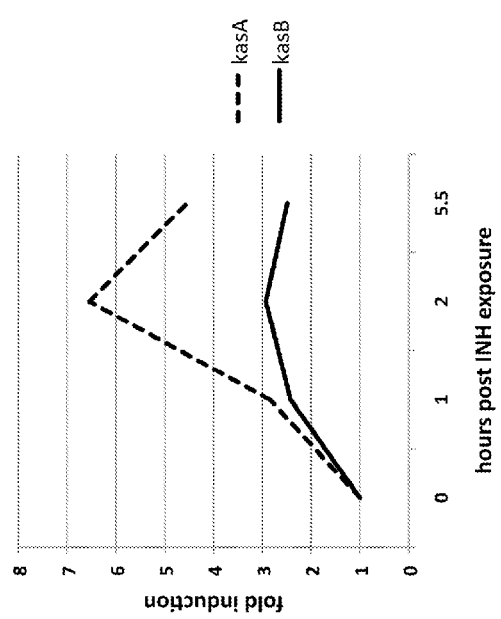
FIG. 19 is a line graph showing the time course of induction of INH-induced genes in *M. tuberculosis*. Isoniazid sensitive H37Rv was exposed to 0.4 µg/ml INH (5×MIC), and RNA was prepared from 10 ml of culture at 1, 2, and 5 hours. qRT-PCR was then used to quantify the abundance of transcripts to kasA, kasB, and sigA, Levels are normalized to sigA and compared to t=0.
Figure 20:
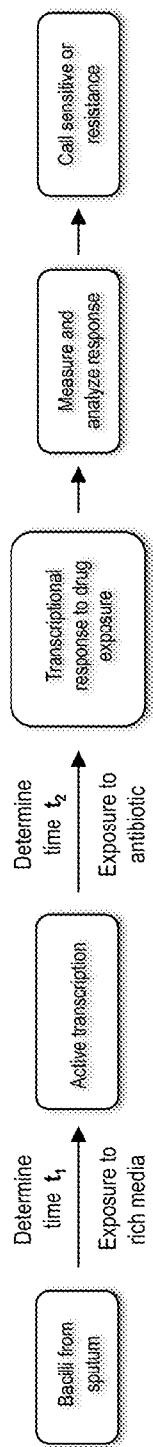
FIG. 20 is an exemplary work flow for detecting expression signatures. Because the actual physiologic state of bacilli in sputum is unknown, both replicating and non-replicating bacteria are modeled in process development. H37Rv grown in axenic culture (either in rich 7H9/OADC/ SDS media or starved in 7H9/tyloxapol) represent bacilli in sputum in these experiments. The bacilli are pulsed for some time $t_1$ with exposure to rich media to stimulate resuscitation from a dormant state and to active transcription. The optimal $t_1$ is determined experimentally. The bacilli are then pulsed for some time $t_2$ with exposure to drug to elicit a transcriptional response. The optimal $t_2$ is determined experimentally. Finally, all samples are processed and analyzed by expression profiling and confirmed by quantitative RT-PCR.
Figure 21:
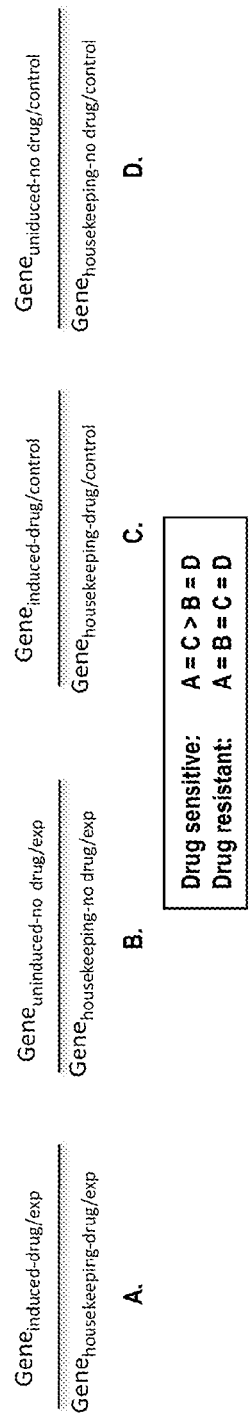
FIG. 21 is an exemplary method to compare expression ratios of genes to distinguish drug sensitive and resistant bacilli. Using quantitative RT-PCR, mRNA levels are measured for genes that are candidates for inclusion in an expression signature. The mRNA levels of a gene of interest are measured in a sample designated "experimental (exp)" (i.e., clinical isolate) in the presence of drug (induced-drug) and the absence of drug (uninduced-no drug). The mRNA levels of a standard housekeeping gene are also measured in the presence (housekeeping-drug) and absence (housekeeping-no drug) of drug. The ratio of the levels of the gene of interest and the housekeeping gene allow for normalization of expression in the presence of drug (A) and in the absence of drug (B). It is anticipated that for some drug sensitive strains, A>B and for drug resistant strains, A=B. Finally, the same corresponding ratios are generated for control strains (C and D) that are known to be drug sensitive and drug resistant. These control values act as standards for the comparison of experimental ratios obtained from unknown strains.

In addition to the above characteristics for ideal genes to be included in the signature (i.e., conserved across TB strains, specific for TB genome), several other characteristics are prioritized in gene selection for signatures of drug resistance. Because drug resistance will be determined by the difference between transcript induction in drug sensitive and drug resistant strains, ideal gene candidates will be highly induced in drug sensitive strains upon exposure to a given drug. Ideally, these genes are induced early and quickly, as this time period will determine to a large extent, the rapidity of the overall diagnostic test. Based on data using qRT-PCR, a transcriptional response to drug exposure is observed in as little as 1-2 hours (FIG. 19). Given the half-lives of mRNA molecules, exploiting gene induction rather than gene repression provides a more rapid and detectable response.

For all the described experiments involving isoniazid and streptomycin, TB strain H37Rv was used in a BSL3 setting in which a set of singly resistant strains has been generated to be used to compare to the wild-type, fully drug sensitive H37Rv. To ensure that rifampin remains a treatment option in the unlikely event of a laboratory-acquired infection, rifampin resistant mutants will be generated in an auxotrophic strain of TB (lysA, panC) that requires the addition of lysine and pantothenate for growth.

Finally, signatures that are unique to each antibiotic have been identified rather than a general stress response to any or all antibiotics. The rationale for this specificity is that in a clinical setting, many patients will have already been empirically treated with different antibiotics and thus some general stress response may have already been activated in the bacilli within a sputum sample. However, drug specific responses are preserved for testing and analysis.

i. Expression profiling in response to antibiotic exposure. Expression profiling to identify candidate genes that distinguish transcriptional responses in drug sensitive and resistant strains of H37Rv has been performed. Because the replication state or transcriptional activity of the bacilli in sputum is unknown, additional experiments are performed on non-replicating (induced through a 5 week carbon starvation model) bacilli. It will determined if the non-replicating bacilli require a short period ($t_1$) of "growth stimulation" in rich media (7H9/OADC) in order to stimulate some basal transcription that can then be responsive to drug exposure (FIG. 20). The optimal period of time ($t_2$) that is required for drug exposure in order to obtain robust signature to distinguish drug sensitive and resistant strains and the optimal drug concentration is also determined to obtain a robust, reproducible response. These experiments will be performed for each of the individual antibiotics.

A completely non-replicating state is the "worst case scenario" (i.e., the longest period that would be required) if bacilli in sputum is in a non-replicating, dormant state. In fact, based on published work examining expression profiles from bacilli in patient sputum, this period will be extremely short if necessary at all, given that expression profiles were obtained directly from sputum bacilli. (Of note, this published data will also be incorporated into the analysis to provide initial insight into possible gene candidates in bacteria in sputum.) A matrix of profiling experiments are performed, varying the time of exposure to rich 7H9/OADC media ($t_1$) from 0, 1, and 2 hours; for each $t_1$, and the time of exposure to each antibiotic ($t_2$). For each set of $t_1$ and $t_2$, the antibiotic concentration is varied from 1×, 3×, and 5× the minimum inhibitory concentration (MIC) for each antibiotic, for both sensitive and resistant H37Rv strains to determine the optimal parameters. Expression profiling will be used to identify optimal conditions for producing robust, reproducible profiles.

Based on the optimized conditions ($t_1$ and $t_2$), expression profiling is performed on drug sensitive and resistant H37Rv strains under these conditions. Bioinformatic analysis is performed to identify genes for each drug in which the level of induction is high in drug sensitive strains relative to drug resistant strains (with the exception of rifampin in which the level of repression is high in drug sensitive strains relative to drug resistant strains). The levels of expression will be compared between drug sensitive and drug resistant strains and confirmed by quantitative RT-PCR.

ii. Develop analysis algorithm to identify drug resistance. An optimal algorithm is determined to analyze expression ratios for sets of genes that distinguish sensitive and resistant strains (as defined by standard MIC measurements). One of the strengths of this method is that for the majority of cases (i.e., those cases which have not been pre-exposed to TB antibiotics), a comparison can be done between the gene expression levels of the same strain not exposed and exposed to a given antibiotic. Quantitative RT-PCR is used to measure mRNA levels from H37Rv under conditions that include 1. exposure to no antibiotic, 2. exposure to isoniazid, 3. exposure to rifampin, 4. exposure to ethambutol, 5. exposure to streptomycin, and 6. exposure to moxifloxacin. The level of expression from a given gene after exposure to antibiotic will be normalized to the level of expression from a set of steady-state, housekeeping genes (i.e., sigA, which encodes the principal sigma factor that stimulates the transcription of housekeeping genes, and rpoB, which encodes a synthetic subunit of RNA polymerase) and compared to the same normalized level of expression of the same gene in the absence of antibiotic exposure. Comparisons will also be made to standard sensitive and resistant control strains (FIG. 21). Ideally, exposure to a particular drug will induce gene expression in drug sensitive strains to high levels, A>>B while for drug resistant strains, which are insensitive to the drug exposure, A=B. (The exception will be for rifampin, in which gene repression of the mRNAs with shortest half-life is detected, given the mechanism of rifampin, i.e., A=C<<B=D.) Because of the large dynamic range of transcription levels, genes are selected for which the ratio of C/D is maximal, thus allowing for clear robust differentiation of sensitive and resistant strains. In addition, optimal, unique set of genes have been selected for each individual antibiotic so that there is no overlap in induced responses with other antibiotics.

iii. Analysis of impact of pre-antibiotic exposure on TB bacilli signatures. To determine the efficacy of these signatures to identify resistance patterns even in the event that a patient has been pre-treated with antibiotics, drug sensitive and resistant TB bacilli (replicating, non-replicating, within macrophages) are pre-expose to amoxicillin, cephalosporins, trimethoprim-sulfamethoxazole, and erythromycin which are common antibiotics to which a patient may be exposed in TB endemic settings, prior to application of this test. Pre-exposure of TB bacilli to different combinations of current TB drugs is also performed to determine if such pre-exposure also interferes with the transcriptional response our ability to detect such a response. Unique signatures should be preserved, thus not impairing our ability to determine resistance. Gene expression levels of a set of genes of interest will be determined using quantitative RT-PCR.

iv. Probe selection of expression signature to identify resistance profile. Based on the data obtained in Sub-aim Bi, a set of candidate genes have been selected that will create a signature for transcriptional response to antibiotic exposure. Two 50 base-pair regions for each gene are selected within regions that are highly conserved across TB genomes. The probes are selected bioinformatically to fit within a 5 degree melting temperature window and with minimal mRNA secondary structure. These probes will be used to compare drug sensitive and resistant strains using available technology under conditions described above, including bacilli in axenic culture that are initially replicating or nonreplicating, intracellular bacilli in a cell culture macrophage infection model that we have currently in our laboratory, and bacteria pre-exposed to different antibiotic combinations. All results will be compared to data obtained by quantitative RT-PCR. Improvement and refinement of the set will occur in an iterative manner.

C. Optimization of Sample Processing for Digital Gene Expression with Molecular Bar Codes.

In addition to defining probe sets for identification of expression signatures, the second major challenge is to optimize processing of samples in order to measure digital gene expression from bacilli present within the sample. Because the majority of TB cases is pulmonary in origin and the majority of samples to be processed is patient sputum, processing of sputum samples to obtain mRNA measurements from infecting TB bacilli is optimized. A spiked sputum model is used in which sputum collected from healthy, uninfected patients (who have not been treated with antibiotics) was spiked with TB bacilli that are either in a replicating or non-replicating (carbon starved) state. Issues that will be addressed include dealing with the variable viscosity of sputum and efficiently lysing the TB bacilli within a sputum sample. One of the major advantages of digital gene expression is the ability to hybridize the mRNAs to their respective probes in extremely crude samples, including crude cell lysates, fixed tissue samples, cells in whole blood and urine, cells from crude lysates of ticks, and samples containing 400 mM guanidinium isothiocyanate (GITC), polyacrylamide, and trizol. Thus, initial indications suggest that no purification step will be required after lysing the bacteria within the sputum, as no purification has been required from whole blood, urine, or fixed tissue samples. The only requirement is sufficient mixing to allow contact between the probes and the mRNAs.

For these experiments, uninfected sputum is obtained from the Brigham and Women's Hospital (BWH) specimen bank. The specimen bank is an IRB regulated unit directed by Lyn Bry, M D, PhD of the BWH pathology department. Discarded sputum will be obtained after all processing is completed in the laboratory (generally within 12-24 hours of collection). Sputum is only collected from subjects who have not received any antibiotics in the previous 48 hours. All samples will be de-identified and no protected health information is collected. Based on the current load of the specimen lab, the necessary amount of sputum (25-50 mL) is obtained within a matter of weeks.

i. Sputum processing. Sputum samples vary in bacterial load, consistency, and viscosity. Several approaches are tested to maximize the rapidity with which the bacteria come into contact with bactericidal levels of antibiotic in media conditions and exposure to oligomer probes for hybridization. Several methods of processing sputum, including no processing, passage of sputum through a syringe needle, treatment with lysozyme and/or DNase, Sputalysin (Calbiochem; 0.1% DTT) which is standardly used to treat sputum from cystic fibrosis patients, or simple dilution of the sample into some minimal denaturant (i.e., GITC) are used. Sputum spiked with H37Rv and processed by a variety of methods to alter its viscosity are performed to determine if any of these methods interferes with the technology.

ii. Bacterial lysis in sputum spiked with TB bacilli. Several approaches to efficiently lyse bacterial cells, arrest transcription and enzyme-based mRNA degradation, and make mRNA accessible to the probes are used in the assay. Previous studies examining the transcriptional responses of bacteria in sputum have first added GTC or similar reagents to the samples to arrest the transcriptional response. Centrifugation can then be used to concentrate bacteria from sputum samples after GTC treatment. Lysis of mycobacteria is generally accomplished through physical means, i.e. homogenization with 0.1 ml glass or zirconium beads. Such physical means are explored to disrupt the bacteria within processed sputum to analyze bacilli that has been spiked into uninfected human sputum using the designed probe set from 1A to detect TB bacilli.

Alternative methods are used for lysis that may be more amenable to field-based considerations, including phage lysis. Addition of phage, or more optimally, purified phage lysin(s), may provide a low-cost, simple, and non-electrical option for bacterial lysis. The Fischetti lab (Rockefeller University) has recently demonstrated the rapid and thorough lysis of several Gram-positive species using purified bacteriophage lysins, which enzymatically hydrolyse peptidoglycan, leading to osmotic lysis. The Hatfull lab (University of Pittsburgh) is currently working to characterize the activity and optimize the performance of LysA enzymes from several lytic mycobacteriophages. In the absence of purified lysins, investigations are performed to determine whether high MOI-infection of TB with a lytic bacteriophage such as D29 can efficiently lyse TB in sputum. It is currently unclear how this approach will affect the transcriptional profile of the bacteria, since it will likely need to occur in the absence of denaturants that would impair the binding, entry, and subsequent lytic properties of the phage. The mycobacteriophage TM4 also expresses a structural protein, Tmp, with peptidoglycan hydrolase activity, which may allow it to be used as a rapid means of cell lysis at high MOI. Once lysed, the mRNA is stabilized with GITC, RNAlater, or other reagents that will inactivate endogenous RNAse activity.

Example 5

Bacterial and fungal culture: *E. coli, K. pneumoniae, P. aeruginosa, Providencia stuartii, P. mirabilis, S. marcescens, E. aerogenes, E. cloacae, M. morganii, K. oxytoca, C. freundii*, or *C. albicans* were grown to an $OD_{600}$ of ~1 in Luria-Bertani medium (LB). For mixing experiments, equal numbers of bacteria as determined by $OD_{600}$ were combined prior to lysis for NanoString™ analysis. *Mycobacterium* isolates were grown in Middlebrook 7H9 medium to mid-log phase prior to harvest or antibiotic exposure as described below.

Derivation of resistant laboratory bacterial strains: *E. coli* laboratory strain J53 with defined fluoroquinolone-resistant chromosomal mutations in gyrA (gyrA1-G81D; gyrA2-S83L) were obtained from the Hooper lab, Massachusetts General Hospital, Boston, Mass. Plasma-mediated quinolone resistance determinants (oqxAB, qnrB, aac6-Ib) were purified from clinical isolates previously determined to contain these plasmids. *E. coli* parent strain J53 was transformed with these plasmids, and their presence was confirmed with PCR.

Viral and *plasmodium* infections: HeLa cells ($1 \times 10^6$), 293T cells ($2 \times 10^5$), and human peripheral blood monocytes ($5 \times 10^5$), were infected with HSV-1 strain KOS and HSV-1 strain 186 Syn+, influenza A P R8, or HIV-1 NL-ADA, respectively, at the noted MOIs. Primary red blood cells ($5 \times 10^9$) were infected with *P. falciparum* strain 3D7 until they reached the noted levels of parasitemia. At the indicated times, the cells were washed once with PBS and harvested.

Antibiotic exposure: Cultures of *E. coli* or *P. aeruginosa* were grown to an $OD_{600}$ of ~1 in LB. Cultures were then divided into two samples, one of which was treated with antibiotic (*E. coli* for 10 minutes: ciprofloxacin 4-8 µg/ml or 300 ng/ml, gentamicin 64 or 128 µg/ml, or ampicillin 500 µg/ml; *P. aeruginosa* for 30 minutes: ciprofloxacin 16

µg/ml). Both treated and untreated portions were maintained at 37° C. with shaking at 200 rpm. Cultures of S. aureus or E. faecium were grown to an $OD_{600}$ of ~1 in LB. Cultures were then exposed to cloxacillin (25 µg/mL) or vancomycin (128 µg/mL), respectively, for 30 minutes.

Cultures of M. tuberculosis were grown to mid-log phase then normalized to $OD_{600}$ of 0.2. 2 ml of each culture were treated with either no antibiotic or one of the following (final concentration): isoniazid 0.2-1.0 µg/ml; streptomycin 5 µg/ml, rifampicin 0.5 µg/ml, or ciprofloxacin 5 µg/ml. The plates were sealed and incubated without shaking for 3 or 6 hours. Lysates were then made and analyzed as described above, using probes listed in Table 6.

Sample processing: For Gram negative isolates, 5-10 µl of culture was added directly to 100 µl RLT buffer and vortexed. For clinical specimens, 20 µl of urine from patients determined by a clinical laboratory to have E. coli urinary tract infection was added directly to 100 µl of RLT buffer. For mycobacteria, 1.5 ml of culture was centrifuged, then resuspended in Trizol (Gibco) with or without mechanical disruption by bead beating, and the initial aqueous phase was collected for analysis. Viral and parasite RNA were similarly prepared using Trizol and chloroform. For all lysates, 3-5 µl were used directly in hybridizations according to standard NanoString™ protocols. Raw counts were normalized to the mean of all probes for a sample, and fold induction for each gene was determined by comparing antibiotic-treated to untreated samples.

Selection of organism identification probes: To select NanoString™ probes for differential detection of organisms, all publically available sequenced genomes for relevant organisms were compared. Genes conserved within each species were identified by selecting coding sequences (CDS) having at least 50% identity over at least 70% of the CDS length for all sequenced genomes for that species. The CDS was broken into overlapping 50-mers and retained only those 50-mers perfectly conserved within a species and having no greater than 50% identity to a CDS in any other species in the study. Available published expression data in Gene Expression Omnibus was reviewed, and genes with good expression under most conditions were selected. To identify unique M. tuberculosis probes, published microarray data was used to identify highly expressed genes falling into one of two classes: those unique to the M. tuberculosis complex (>70% identity to any other gene in the non-redundant database using BLASTN and conserved across all available M. tuberculosis and M. bovis genomes), as well as those with >85% identity across a set of clinically relevant mycobacteria including M. tuberculosis, M. avium, and M. paratuberculosis. C. albicans probes were designed against 50-mer segments of C. albicans genome unique in comparison with the complete genomes of ten additional pathogenic organisms that were included in its probe set. Viral probes were designed against highly conserved genes within a virus (i.e. all HSV-2 or HIV-1 isolates) that were less conserved among viruses within the same family, (i.e between HSV-1 and HSV-2). Plasmodium falciparum probes were designed against genes expressed abundantly in each of the blood stages of the parasite life cycle. All probes were screened to avoid cross hybridization with human RNA.

Probe Sets: For Gram-negative organism identification, a pooled probe-set containing probes for E. coli, K. pneumoniae, and P. aeruginosa were used. For mycobacterial organism identification, species-specific probes for M. tuberculosis and broader mycobacterial genus probes were among a larger set of probes against microbial pathogens.

Figure 23:
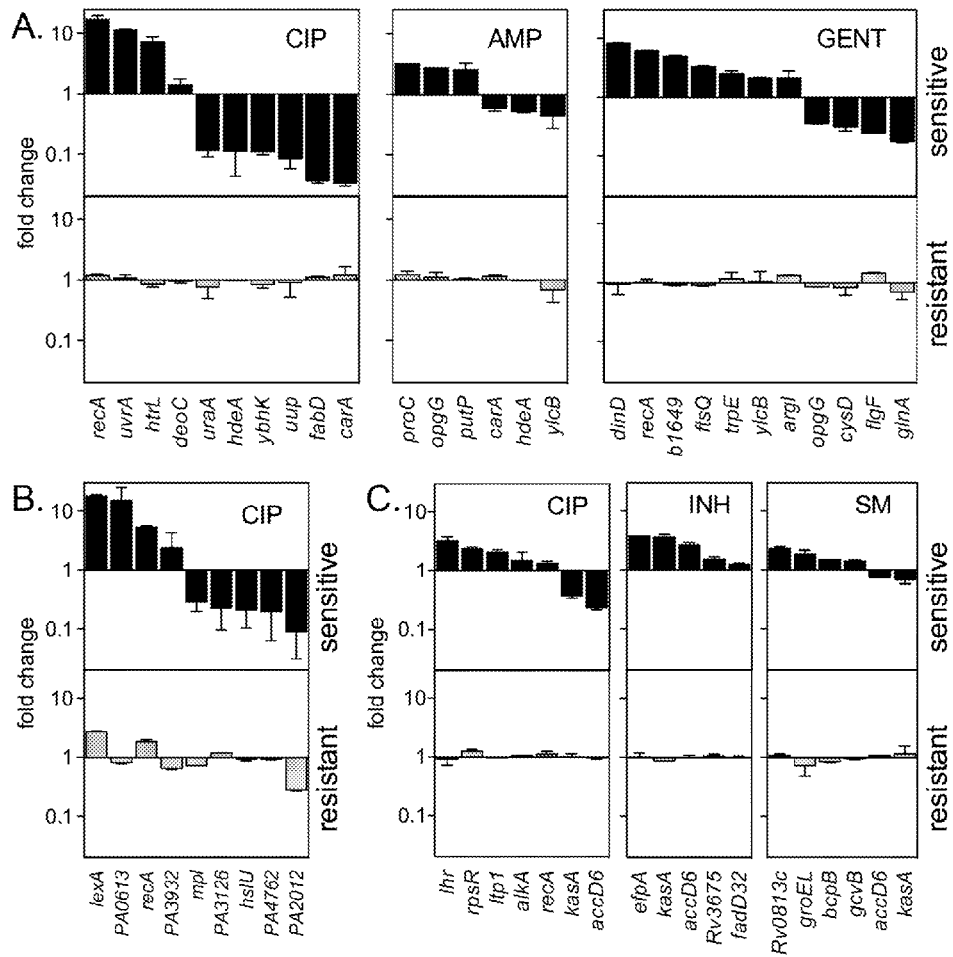
FIG. 23 is a panel of seven bar graphs showing RNA expression signatures that distinguish sensitive from resistant bacteria upon antibiotic exposure. Sensitive or resistant bacterial strains were grown to log phase, briefly exposed to antibiotic, lysed, and analyzed using NanoString™ probe-sets designed to quantify transcripts that change in response to antibiotic exposure. Raw counts were normalized to the mean of all probes for a sample, and fold induction was determined by comparing drug-exposed to unexposed samples. Y-axis: fold-change; X-axis: gene name. Signatures for susceptible strains (black; top panel) or resistant strains (grey; bottom panel) upon exposure to (A) *E. coli*: ciprofloxacin (CIP), ampicillin (AMP), or gentamicin (GM), (B)

Probes were designed for genes that are differentially regulated upon exposure to various antimicrobial agents to measure the presence or absence of a response (Sangurdekar et al., Genome Biology 7, R32 (2006); Anderson et al., Infect. Immun. 76, 1423-1433, (2008); Brazas and Hancock, Antimicrob. Agents Chemother. 49, 3222-3227, (2005)). Following 10-30 minute exposures of wild-type E. coli K-12 to ciprofloxacin, gentamicin, or ampicillin, the expected changes in transcript levels that together define the drug-susceptible expression signature for each antibiotic were observed (FIGS. 23A and 23B, Table 7). These signatures were not elicited in the corresponding resistant strains (FIGS. 23A and 23B).

Rapid phenotypic drug-susceptibility testing would make a particularly profound impact in tuberculosis, as established methods for phenotypic testing take weeks to months (Minion et al., Lancet Infect Dis 10, 688-698, (2010)). Expression signatures in response to anti-tubercular agents isoniazid, ciprofloxacin, and streptomycin were able to distinguish susceptible and resistant isolates after a 3 to 6 hour antibiotic exposure (FIG. 23C). Some genes in the transcriptional profiles are mechanism-specific (i.e., recA, alkA, and 1 hr for ciprofloxacin; groEL for streptomycin; and kasA and accD6 for isoniazid). Other genes, particularly those involved in mycolic acid synthesis or intermediary metabolism, are down-regulated in response to multiple antibiotics, indicating a shift away from growth towards damage control.

To condense these complex responses into a single, quantitative metric to distinguish susceptible and resistant strains, the metric of the mean-squared distance (MSD) of the expression response was utilized from each experimental sample from the centroid of control, antibiotic-susceptible samples. Antibiotic-susceptible strains cluster closely, thus possessing small MSDs. Conversely, antibiotic-resistant strains have larger values, the result of numerous genes failing to respond to antibiotic in a manner similar to the average susceptible strain. MSD is reported as dimensionless Z-scores, signifying the number of standard deviations a sample lies from the average of sensitive isolates of E. coli (FIGS. 24A, 24B, 27, and 28) or M. tuberculosis (FIGS. 24C and 29).

Because expression profiles reflect phenotype rather than genotype, resistance mediated by a variety of mechanisms can be measured using a single, integrated expression signature. The transcriptional responses of ciprofloxacin-susceptible E. coli strain J53 were compared with a series of isogenic mutants with different mechanisms of resistance: two with single mutations in the fluoroquinolone-target gene topoisomerase gyrA (G81D or S83L) and three carrying episomal quinolone resistance genes including aac(6')-Ib (an acetylating, inactivating enzyme), qnrB (which blocks the active site of gyrA), and oqxAB (an efflux pump). In comparison with the parent strain, all J53 derivatives had large Z-scores, reflective of resistance (FIG. 24B).

Response to isoniazid was compared in a series of sensitive clinical and laboratory isolates and two isoniazid resistant strains, including an H37Rv-derived laboratory strain carrying a mutation in katG (S315T), a catalase necessary for pro-drug activation, and a clinical isolate with a mutation in the promoter of inhA (C-15T), the target of isoniazid. Due to their disparate resistance mechanisms, these two strains have differing levels of resistance to isoniazid, with the katG mutant possessing high level resistance (>100-fold increase in minimal inhibitory concentration (MIC) to >6.4 µg/mL), while the inhA promoter mutation confers only an 8-fold increase in the MIC to 0.4 µg/mL.

Exposure to low isoniazid concentrations (0.2 μg/mL) failed to elicit a transcriptional response in either resistant strain, but at higher isoniazid concentrations (1 μg/mL), the inhA mutant responds in a susceptible manner in contrast to the katG mutant (FIG. 24C). Thus, this method is not only mechanism-independent, but can also provide a relative measure to distinguish high and low-level resistance.

Finally, because RNA is almost universal in pathogens ranging from bacteria, viruses, fungi, to parasites, RNA detection can be integrated into a single diagnostic platform applicable across a broad range of infectious agents. Using a large pool of mixed pathogen probes, we were able to directly and specifically detect signals to identify the fungal pathogen *Candida albicans* (FIG. 25A); human immunodeficiency virus (HIV), influenza virus, and herpes simplex virus-2 (HSV-2) in cell culture in a dose dependent manner (FIGS. 25B-D); and the different stages of the *Plasmodium falciparum* life cycle in infected erythrocytes (FIG. 25E).

NanoString™ data analysis and calculation of distance metric mean squared distance for drug-sensitivity: For all drug-treated samples, raw NanoString™ counts for each probe were first normalized to the mean of all relevant (i.e., species-appropriate) probes for each sample. Fold-change in transcript levels was determined by comparing the normalized counts for each probe in the antibiotic-treated samples with the corresponding counts in the untreated baseline sample for each test condition.

To transform qualitative expression signatures into a binary outcome of sensitive or resistant, an algorithm was developed to calculate mean squared distance (MSD) of a sample's transcriptional profile from that of sensitive strains exposed to the same drug. The MSD metric in drug-sensitivity experiments was calculated as follows:

1. Variation in sample amount is corrected for by normalizing raw values to the average number of counts for all relevant probes in a sample.

2. A panel of NanoString™ probes, which we denote $P_j$, is selected. The subscript j runs from 1 to $N_{probes}$, the total number of selected probes. The analysis is restricted to probes that changed differentially between drug-sensitive and drug-resistant isolates.

3. Replicates of the drug-sensitive strain are defined as $N_{samp}$. For each replicate, normalized counts for each probe $P_j$ before or after drug treatment were denoted $C_{i,P_j}^{before}$ or $C_{i,P_j}^{after}$, with i signifying the sample index.

4. "Log induction ratio" is next computed:

$$S_{i,P_j} = \ln[C_{i,P_j}^{before}/C_{i,P_j}^{after}]$$

Log transforming the ratio in this way prevents any single probe from dominating the calculated MSD.

5. The average induction ratio of the drug sensitive samples, $\overline{S_j}$, is calculated by summing over the different biological replicates and normalizing by the number of samples:

$$\overline{S_j} = \frac{\sum_{i=1}^{N_{samp}} S_{i,P_j}}{N_{samp}}$$

6. MSD is next calculated for the each of the replicates of the drug sensitive strain (of index i), a number that reflects how different a sample is from the average behavior of all drug sensitive samples:

$$MSD_i^R = \frac{\sum_{P_j=1}^{N_{probes}} (S_{i,P_j} - \overline{S_j})^2}{N_{probes}}$$

7. Induction ratios for resistant strains, $R_{i,P_j}$, are calculated similarly to those of sensitive strains:

$$R_{i,P_j} = \ln[C_{i,P_j}^{before}/C_{i,P_j}^{after}]$$

8. The MSD for the drug resistant strains is calculated relative to the centroid of the drug-sensitive population:

$$MSD_i^R = \frac{\sum_{P_j=1}^{N_{probes}} (R_{i,P_j} - \overline{S_j})^2}{N_{probes}}$$

Because most sensitive strains behave similarly to the average sensitive strain the typical value for $MSD_i^S$ is small compared to the typical value for a resistant strain, $MSD_i^S$.

Finally, statistical significance of the measured MSD values were assigned. Because the $MSD_i^S$ values are the sum of a number of random deviations from a mean, they closely resemble a normal distribution, a consequence of the Central Limit Theorem. Therefore, z-scores, which reflect the number of standard deviations away a given sample is relative to the drug sensitive population, were computed for each sample:

$$\bar{z}_i \equiv \frac{MSD_i - \overline{MSD^S}}{\sigma_{MSD^S}}$$

where the standard deviations and means are defined as:

$$\sigma_{MSD^S} \equiv \sqrt{\frac{1}{N_{samp}} \sum_{i=1}^{N_{samp}} (MSD_i^S - \overline{MSD^S})^2}$$

and:

$$\overline{MSD^S} = \sum_{i=1}^{N_{samp}} MSD_i^S$$

This metric was applied to the analysis of numerous laboratory and clinical isolates that were tested against different antibiotics and the data are shown in FIGS. 24, 27, 28, and 29.

Calculation of distance metric for organism identification: To transform the information from multiple probes into a binary outcome, raw counts for each probe were log-transformed. Log transforming the ratio in this way prevents any single probe from dominating the analysis. These log-transformed counts were then averaged between technical replicates.

A panel of NanoString™ probes, which are denoted $P_j$, is selected as described. The subscript j runs from 1 to $N_{probes}$, the total number of selected probes.

$$S_{i,P_j} = \ln[C_{i,P_j}]$$

Because organism identification depends on an ability to detect transcripts relative to mocks or different organisms, background level of NanoString™ counts in samples prepared without the organism of interest was thus used to define a control centroid. The centroid of these control samples, $\overline{S}_j$, is calculated by summing over the different biological replicates and normalizing by the number of samples:

$$\overline{S}_j = \frac{\sum_{i=1}^{N_{samp}} S_{i,P_j}}{N_{samp}}$$

MSD is next calculated for the averaged technical replicates of the experimental samples (of index i), a number that reflects how different a sample is from the average behavior of all control samples:

$$MSD_i^R = \frac{\sum_{P_j=1}^{N_{probes}} (S_{i,P_j} - \overline{S}_j)^2}{N_{probes}}$$

Finally, statistical significance was assigned to the measured MSD values. Because the $MSD_i^S$ values are the sum of a number of random deviations from a mean, they closely resemble a normal distribution, a consequence of the Central Limit Theorem. We therefore computed z-scores for each sample, which reflect the number of standard deviations away a given sample is relative to the control population:

$$z_i \equiv \frac{MSD_i - \overline{MSD^S}}{\sigma_{MSD^S}}$$

where the standard deviations and means are defined as:

$$\sigma_{MSD^S} \equiv \sqrt{\frac{1}{N_{samp}} \sum_{i=1}^{N_{samp}} (MSD_i^S - \overline{MSD^S})^2}$$

and:

$$\overline{MSD^S} = \sum_{i=1}^{N_{samp}} MSD_i^S$$

This metric was applied to the analysis of numerous laboratory strains and clinical isolates that were tested for the relevant bacterial species as shown in FIG. 26 and Table 4. A strain was identified as a particular organism if the MSD>2 for that organism.

TABLE 4

Numbers of laboratory and clinical isolates tested with organism identification probes.

| Organism | Laboratory strains tested | Clinical isolates tested |
|---|---|---|
| E. coli | 2 | 17 |
| K. pneumoniae | 0 | 4 |
| P. aeruginosa | 1 | 9 |
| M. tuberculosis | 1 | 10 |

TABLE 5

Genes used for bacterial organism identification.

| Organism | Gene | Annotated function |
|---|---|---|
| E. coli | ftsQ | Divisome assembly |
| | murC | Peptidoglycan synthesis |
| | putP | Sodium solute symporter |
| | uup | Subunit of ABC transporter |
| | opgG | Glucan biosynthesis |
| K. pneumoniae | mraW | S-adenosyl-methyltransferase |
| | ihfB | DNA-binding protein |
| | clpS | Protease adaptor protein |
| | lrp | Transcriptional regulator |
| P. aeruginosa | mpl | Ligase, cell wall synthesis |
| | proA | Gamma-glutamyl phosphate reductase |
| | dacC | Carboxypeptidase, cell wall synthesis |
| | lipB | Lipoate protein ligase |
| | sltB1 | Transglycosylase |
| Conserved Mycobacterium | carD | Transcription factor |
| | infC | Translation initiation factor |
| M. tuberculosis | Rv1398c | Hypothetical protein |
| | mptA | Immunogenic protein 64 |
| | hspX | Heat shock protein |

TABLE 6

Laboratory and clinical isolates tested for susceptibility profiling. Clinical isolates are designated CI.

| Organism | Antibiotic | Sensitive (S) or Resistant (R) | Strain | MIC* |
|---|---|---|---|---|
| E. coli | Ciprofloxacin | S | K12 | 30 ng/ml |
| | | S | J53 | 30 ng/ml |
| | | S | CIEC9955 | <0.1 µg/ml |
| | | S | CICr08 | <.1 µg/ml |
| | | R | CIEC1686 | 50 µg/ml |
| | | R | CIEC9779 | 50 µg/ml |
| | | R | CIEC0838 | 50 µg/ml |
| | | R | CIqnrS | 6.25 µg/ml |
| | | R | CIaac6-Ib | >100 µg/ml |
| | | R | CIqnrA | 12.5 µg/ml |
| | | R | CIqnrB | 6.25 µg/ml |
| E. coli | Gentamicin | S | K12 | 8 µg/ml |
| | | S | CIEC1676 | 8 µg/ml |
| | | S | CIEC9955 | 16 µg/ml |
| | | S | CIEC1801 | 8 µg/ml |
| | | R | CIEC4940 | >250 µg/ml |
| | | R | CIEC9181 | >250 µg/ml |
| | | R | CIEC2219 | 125 µg/ml |
| E. coli | Ampicillin | S | K12 | 4 µg/ml |
| | | | J53 | 4 µg/ml |
| | | | DH5α | 8 µg/ml |
| | | R | CIEC9955 | >250 µg/ml |
| | | | CIEC2219 | >250 µg/ml |
| | | | CIEC0838 | >250 µg/ml |
| | | | CIEC9181 | >250 µg/ml |
| P. aeruginosa | Ciprofloxacin | S | PAO-1 | 1 µg/ml |
| | | S | CIPA2085 | 0.4 µg/ml |
| | | S | CIPA1189 | 0.4 µg/ml |
| | | S | CIPA9879 | 0.4 µg/ml |
| | | R | CIPA2233 | 50 µg/ml |
| | | R | CIPA1839 | 25 µg/ml |
| | | R | CIPA1489 | 25 µg/ml |
| M. tuberculosis | Isoniazid | S | H37Rv | 0.05 µg/ml |
| | | S | AS1 (CI) | <0.2 µg/ml |
| | | S | AS2 (CI) | <0.2 µg/ml |
| | | S | AS3 (CI) | <0.2 µg/ml |
| | | S | AS4 (CI) | <0.2 µg/ml |
| | | S | AS5 (CI) | <0.2 µg/ml |
| | | S | AS10 (CI) | <0.2 µg/ml |
| | | R | A50 | >6.25 µg/ml |
| | | R | BAA-812 | 0.4 µg/ml |
| M. tuberculosis | Ciprofloxacin | S | mc²6020 | 0.5 µg/ml |
| | | S | AS1 (CI) | <1 µg/ml |
| | | S | AS2 (CI) | <1 µg/ml |

TABLE 6-continued

Laboratory and clinical isolates tested for susceptibility profiling. Clinical isolates are designated CI.

| Organism | Antibiotic | Sensitive (S) or Resistant (R) | Strain | MIC* |
|---|---|---|---|---|
| | | S | AS3 (CI) | <1 µg/ml |
| | | S | AS4 (CI) | <1 µg/ml |
| | | S | AS5 (CI) | <1 µg/ml |
| | | S | AS10 (CI) | <1 µg/ml |
| | | R | C5A15 | 16 µg/ml |
| M. tuberculosis | Streptomycin | S | H37Rv | 1 µg/ml |
| | | S | AS1 (CI) | <2 µg/ml |
| | | S | AS2 (CI) | <2 µg/ml |
| | | S | AS3 (CI) | <2 µg/ml |
| | | S | AS4 (CI) | <2 µg/ml |
| | | S | AS5 (CI) | <2 µg/ml |
| | | R | CSA1 | >32 µg/ml |

TABLE 7

Genes associated with antibiotic sensitivity signatures in E. coli, P. aeruginosa, and M. tuberculosis.

| Organism | Antibiotic | Gene | Annotated function |
|---|---|---|---|
| E. coli | Ciprofloxacin | dinD | DNA-damage inducible protein |
| | | recA | DNA repair, SOS response |
| | | uvrA | ATPase and DNA damage recognition protein |
| | | uup | predicted subunit of ABC transporter |
| | Gentamicin | pyrB | aspartate carbamoyltransferase |
| | | recA | DNA repair, SOS response |
| | | wbbK | lipopolysaccharide biosynthesis |
| | Ampicillin | hdeA | stress response |
| | | proC | pyrroline reductase |
| | | opgG | glucan biosynthesis |
| P. aeruginosa | Ciprofloxacin | PA_4175 | probable endoprotease |
| | | mpl | peptidoglycan biosynthesis |
| | | proA | Glutamate-semialdehyde dehydrogenase |
| M. tuberculosis | Ciprofloxacin | lhr | helicase |
| | | rpsR | ribosomal protein S18-1 |
| | | ltp1 | lipid transfer |
| | | alkA | base excision repair |
| | | recA | recombinase |
| | | kasA | mycolic acid synthesis |
| | | accD6 | mycolic acid synthesis |
| | Isoniazid | efpA | efflux pump |
| | | kasA | mycolic acid synthesis |
| | | accD6 | mycolic acid synthesis |
| | | Rv3675 | Possible membrane protein |
| | | fadD32 | mycolic acid synthesis |
| | Streptomycin | Rv0813 | conserved hypothetical protein |
| | | groEL | Heat shock protein |
| | | bcpB | peroxide detoxification |
| | | gcvB | glycine dehydrogenase |
| | | accD6 | mycolic acid synthesis |
| | | kasA | mycolic acid synthesis |

The direct measurement of RNA expression signatures described herein can provide rapid identification of a range of pathogens in culture and directly from patient specimens. Significantly, phenotypic responses to antibiotic exposure can distinguish susceptible and resistant strains, thus providing an extremely early and rapid determination of susceptibility that integrates varying resistance mechanisms into a common response. This principle represents a paradigm shift in which pathogen RNA forms the basis for a single diagnostic platform that could be applicable in a spectrum of clinical settings and infectious diseases, simultaneously providing pathogen identification and rapid phenotypic antimicrobial susceptibility testing.

REFERENCES

1. Global tuberculosis control—surveillance, planning, financing. WHO Report 2008. WHO/HTM/TB/2008.393.

2. Moore D A, Mendoza D, Gilman R H, Evans C A, Hollm Delgado M G, Guerra J, Caviedes L, Vargas D, Ticona E, Ortiz J, Soto G, Serpa J; Tuberculosis Working Group in Peru. 2004. Microscopic observation drug susceptibility assay, a rapid, reliable diagnostic test for multidrug-resistant tuberculosis suitable for use in resource-poor settings. J Clin Microbiol. 42(10):4432-7.

3. Jacobs W R Jr, Barletta R G, Udani R, Chan J, Kalkut G, Sosne G, Kieser T, Sarkis G J, Hatfull G F, Bloom B R. 1993. Rapid assessment of drug susceptibilities of Mycobacterium tuberculosis by means of luciferase reporter phages. Science. 260(5109):819-22.

4. Piuri M, Jacobs W R Jr, Hatfull G F. 2009. Fluoromycobacteriophages for rapid, specific, and sensitive antibiotic susceptibility testing of Mycobacterium tuberculosis. PLoS ONE. 4(3):e4870.

5. Angeby K A, Klintz L, Hoffner S E. 2002. Rapid and inexpensive drug susceptibility testing of Mycobacterium tuberculosis with a nitrate reductase assay. J Clin Microbiol. 40(2):553-5.

6. García de Viedma D. 2003. Rapid detection of resistance in Mycobacterium tuberculosis: a review discussing molecular approaches. Clin Microbiol Infect. 9(5):349-59.

7. Boshoff H I, Myers T G, Copp B R, McNeil M R, Wilson M A, Barry C E 3rd. 2004. The transcriptional responses of Mycobacterium tuberculosis to inhibitors of metabolism: novel insights into drug mechanisms of action. J Biol. Chem. 279(38):40174-84.

8. Fu L M, Shinnick T M. 2007. Understanding the action of INH on a highly INH-resistant Mycobacterium tuberculosis strain using Genechips. Tuberculosis (Edinb) 87(1):63-70.

9. Geiss G K, Bumgarner R E, Birditt B, Dahl T, Dowidar N, Dunaway D L, Fell H P, Ferree S, George R D, Grogan T, James J J, Maysuria M, Mitton J D, Oliveri P, Osborn J L, Peng T, Ratcliffe A L, Webster P J, Davidson E H, Hood L, Dimitrov K. 2008. Direct multiplexed measurement of gene expression with color-coded probe pairs. Nat. Biotechnol. 26(3):317-25.

10. Mdluli K, Slayden R A, Zhu Y, Ramaswamy S, Pan X, Mead D, Crane D D, Musser J M, Barry C E 3rd. 1998. Inhibition of a Mycobacterium tuberculosis beta-ketoacyl ACP synthase by isoniazid. Science. 280(5369):1607-10.

11. Schnappinger D, Ehrt S, Voskuil M I, Liu Y, Mangan J A, Monahan I M, Dolganov G, Efron B, Butcher P D, Nathan C, Schoolnik G K. 2003. Transcriptional Adaptation of Mycobacterium tuberculosis within Macrophages: Insights into the Phagosomal Environment. J Exp Med. 198(5):693-704.

12. Schwab U, Rohde K H, Wang Z, Chess P R, Notter R H, Russell D G. 2009. Transcriptional responses of Mycobacterium tuberculosis to lung surfactant. Microb Pathog. 46(4):185-93

13. Wayne L G, Hayes L G. 1996. An in vitro model for sequential study of shiftdown of Mycobacterium tuberculosis through two stages of nonreplicating persistence. Infect Immun 64:2062-2069.

14. Sambandamurthy V K, Derrick S C, Jalapathy K V, Chen B, Russell R G, Morris S L, Jacobs W R Jr. 2005. Long-term protection against tuberculosis following vaccination with a severely attenuated double lysine and pantothenate auxotroph of *Mycobacterium tuberculosis*. Infect Immun. 73(2):1196-203.

15. Garton N J, Waddell S J, Sherratt A L, Lee S M, Smith R J, Senner C, Hinds J, Rajakumar K, Adegbola R A, Besra G S, Butcher P D, Barer M R. 2008. Cytological and transcript analyses reveal fat and lazy persister-like bacilli in tuberculous sputum. PLoS Med. 5(4):e75.

16. Schuch R, Nelson D, Fischetti V A. 2002. A bacteriolytic agent that detects and kills *Bacillus anthracis*. Nature 418(6900):884-9.

17. Loeffler J M, Nelson D, Fischetti V A. 2001. Rapid killing of *Streptococcus pneumoniae* with a bacteriophage cell wall hydrolase. Science 294(5549):2170-2.

18. Fischetti V A. 2005. Bacteriophage lytic enzymes: novel anti-infectives. Trends Microbiol. 13(10):491-6

19. Piuri M, Hatfull G F. 2006. A peptidoglycan hydrolase motif within the mycobacteriophage TM4 tape measure protein promotes efficient infection of stationary phase cells. Mol. Microbiol. 62(6):1569-85.

20. Anderson G G, Moreau-Marquis S, Stanton B A, O'Toole G A. In vitro analysis of tobramycin-treated *Pseudomonas aeruginosa* biofilms on cystic fibrosis-derived airway epithelial cells. Infect Immun 2008 April; 76(4): 1423-33.

21. Brazas M. D. and Hancock R. E. W. Ciprofloxacin induction of a susceptibility determinant in *Pseudomonas aeruginosa*. AAC 2005 August; 49(8):3222-3227.

22. Sangurdekar D P, Srienc F, Khodursky A B. A classification based framework for quantitative description of large-scale microarray data. Genome Biol 2006; 7(4): R32.

23. Gmuender, H, Kuratli, K, DiPadova K, Gray, G P, Keck W, Evers S. Gene expression changes triggered by Exposure of *Haemophilus Influenzae* to Novobiocin or Ciprofloxacin: Combined Transcription and Translation Analysis. Genome Res. 2001; 11(1):28-42.

24. Klevens R M, Edwards J R, Richards C L, Jr., Horan T C, Gaynes R P, Pollock D A, Cardo D M. Estimating health care-associated infections and deaths in U.S. hospitals, 2002. Public Health Rep. 2007; 122(2):160-6. PMCID: 1820440.

25. Klevens R M, Edwards J R, Gaynes R P. The impact of antimicrobial-resistant, health care-associated infections on mortality in the United States. Clin Infect Dis. 2008; 47(7):927-30.

26. Scott R D. The Direct Medical Costs of Healthcare-Associated Infection in U.S. Hospitals and the Benefits of Prevention. In: Division of Healthcare Quality Promotion NCfP, Detection and Control of Infectious Diseases, editor. Atlanta: CDC; 2009.

27. US action plan to combat antimicrobial resistance. Infect Control Hosp Epidemiol. 2001; 22(3):183-4.

28. Harbarth S, Garbino J, Pugin J, Romand J A, Lew D, Pittet D. Inappropriate initial antimicrobial therapy and its effect on survival in a clinical trial of immunomodulating therapy for severe sepsis. Am J. Med. 2003; 115(7):529-35.

29. Harries A D, Hargreaves N J, Kemp J, Jindani A, Enarson D A, Maher D, Salaniponi F M. Deaths from tuberculosis in sub-Saharan African countries with a high prevalence of HIV-1. Lancet. 2001; 357(9267):1519-23.

30. Lawn S D, Shattock R J, Griffin G E. Delays in the diagnosis of tuberculosis: a great new cost. Int J Tuberc Lung Dis. 1997; 1(5):485-6.

31. Carroll K C. Rapid diagnostics for methicillin-resistant *Staphylococcus aureus*: current status. Mol Diagn Ther. 2008; 12(1):15-24.

32. Fischer H P, Brunner N A, Wieland B, Paquette J, Macko L, Ziegelbauer K, Freiberg C. Identification of antibiotic stress-inducible promoters: a systematic approach to novel pathway-specific reporter assays for antibacterial drug discovery. Genome Res. 2004; 14(1):90-8. PMCID: 314284.

33. Bianchi A A, Baneyx F. Stress responses as a tool To detect and characterize the mode of action of antibacterial agents. Appl Environ Microbiol. 1999; 65(11):5023-7. PMCID: 91676.

34. Shapiro E, Baneyx F. Stress-based identification and classification of antibacterial agents: second-generation *Escherichia coli* reporter strains and optimization of detection. Antimicrob Agents Chemother. 2002; 46(8):2490-7. PMCID: 127359.

35. Freiberg C, Fischer H P, Brunner N A. Discovering the mechanism of action of novel antibacterial agents through transcriptional profiling of conditional mutants. Antimicrob Agents Chemother. 2005; 49(2):749-59. PMCID: 547252.

36. Hutter B, Schaab C, Albrecht S, Borgmann M, Brunner N A, Freiberg C, Ziegelbauer K, Rock C O, Ivanov I, Loferer H. Prediction of mechanisms of action of antibacterial compounds by gene expression profiling. Antimicrob Agents Chemother. 2004; 48(8):2838-44. PMCID: 478524.

37. Utaida S, Dunman P M, Macapagal D, Murphy E, Projan S J, Singh V K, Jayaswal R K, Wilkinson B J. Genome-wide transcriptional profiling of the response of *Staphylococcus aureus* to cell-wall-active antibiotics reveals a cell-wall-stress stimulon. Microbiology. 2003; 149(Pt 10): 2719-32.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

Specimens, clinical syndromes, and pathogens that can be tested with the present methods 1. Sputum
   a. Pneumonia
      i. Bacterial:
         1. *Streptococcus pneumoniae*
         2. *Haemophilus influenza*
         3. *Moraxella catarrhalis*
         4. *Chlamydia pneumoniae*
         5. *Staphylococcus aureus*
         6. *Pseudomonas aeruginosa*
         7. *Stenotrophomonas maltophila*
         8. *Burkholdaria cepaciae*
         9. *Mycobacterium tuberculosis*
         10. *Mycobacterium kansasii*
         11. *Mycobacterium abscessus*
         12. *Mycobacterium avium* complex
         13. *Mycoplasma pneumoniae*
         14. *Legionella* species
         15. *Acinetobacter baumannii*
         16. *Enterobacter*
         17. *Serratia*
         18. *Klebsiella*
      ii. Viral:
         1. Influenza
         2. Respiratory syncytial virus
         3. Parainfluenza
         4. Adenovirus TABLE 1-continued Specimens, clinical syndromes, and pathogens that can be tested with the present methods

- 5. Rhinovirus
- 6. Coronavirus
- 7. Metapneumovirus
- 8. Coxsackievirus
- 9. Echovirus
- 10. Hantavirus
- 11. Varicella Zoster
- 12. CMV
- iii. Fungal:
  1. *Cryptococcus neoformans*
  2. *Blastomycosis*
  3. *Histoplasma capsulatum*
  4. *Coccidiodes immitis*
  5. *Aspergillus* species
  6. *Rhizopus* species
  7. *Mucor* species
  8. *Pneumocystis jirovecii*
  9. *Pseudoaleshceria boydii*
  10. *Scedosproium* spp
- iv. Aspiration pneumonia
  1. *Bacteroides*
  2. *Fusobacterium*
  3. *Peptosteptococcus*
  4. *Peptrococcus*
  5. *prevotella*
- b. Bronchitis and bronchiolitis
  1. Viral:
     a. Influenze
     b. Adenovirus
     c. Rhinovirus
     d. Coronavirus
     e. Parainfluenza virus
     f. Metapneumovirus
     g. Respiratory syncitial virus
     h. Coxsackievirus
  2. Bacterial
     a. *Bordatella pertussis*
     b. *Mycoplasma pneumoniae*
     c. *Chlamydia pneumonia*
2. Urine
   a. Cystitis
      i. Bacterial:
         1. *Escherechia coli*
         2. *Klebsiella oxytoca*
         3. *Proteus*
         4. *pseudomonas*
         5. *Enterobacter*
         6. *Citrobacter*
         7. *Enterococcus*
         8. *Staphylococcus saprophyticus*
      ii. Fungal:
         1. *Candida* species
   b. Pyelonephritis
      i. Bacterial:
         1. *Escherechia coli*
         2. *Klebsiella oxytoca*
         3. *Enterobacter*
         4. *Citrobacter*
         5. *Enterococcus*
         6. *Candida albicans*
      ii. Viral:
         1. BK virus
         2. adenovirus
   c. prostatitis
      i. *Neisseria gonorrhea*
      ii. *E. coli*
      iii. *Klebsiella*
      iv. *Enterobacter*
      v. *Citrobacter*
      vi. *Proteus mirabilis*
      vii. *Chlamydia trachomatis*
      viii. *Ureaplasma*
3. Blood
   a. Endocarditis (native valve and prosthetic valve endocarditis)
      i. Bacterial
         1. *Staphylococcus aureus*
         2. *Streptococcus viridans*
         3. *Enterococcus faecalis*
         4. *Enterococcus faecium*
         5. Coagulase negative *Staphylococcus*
         6. *Streptococcus bovis*
         7. *Pseudomonas aeruginosa*
         8. *Haemophilus parainfluenzae*
         9. *Haemophilus aphrophilus*
         10. *Actinobacillus*
         11. *Cardiobacterium hominis*
         12. *Eikenella corrodens*
         13. *Kingella kingii*
         14. *Bartonella* species
         15. *Coxiella burnetii*
         16. *Chlamydia psittaci*
         17. *Mycoplasma*
         18. *Legionella pneumophila*
         19. *Brucella* species
         20. *Tropheryma whipplei*
         21. *Propionobacterium acnes*
      ii. Fungal
         1. *Candida albicans*
         2. *Candida krusei*
         3. *Candida tropicalis*
         4. *Candida glabrata*
         5. *Candida parapsilosis*
         6. *Candida guillermondii*
   b. Bacteremia
      1. *Staphylococcus aureus*
      2. *Streptococcus viridans*
      3. *Enterococcus faecalis*
      4. *Enterococcus faecium*
      5. Coagulase negative *staphylococcus*
      6. *Streptococcus bovis*
      7. *Pseudomonas aeruginosa*
      8. *Stenotrophomonas*
      9. *Burkholdaria cepacia*
      10. *Acinetobacter* species
      11. *E. coli*
      12. *Salmonella*
      13. *Streptococcus pneumoniae*
      14. *Enterobacter*
      15. *Seratia marcesens*
      16. *Klebsiella* sp
      17. *Proteus*
      18. *Citrobacter*
      19. *Propionobacterium acnes*
   c. Fungemia:
      i. *Candida* species
      ii. *Fusarium* species
      iii. *Aspergillus* species
      iv.
   d. Lemierre's disease
      i. *fusobacterium*
   e. Fever of unknown origin
      i. Malaria
         1. *Plasmodium falciparum*
         2. *Plasmodium malariae*
         3. *Plasmodium ovale*
         4. *Plasmodium vivax*
      ii. Hepatitis:
         1. Hepatitis A
         2. Hepatitis E
      iii. Dengue fever
      iv. Typhoid fever
      v. Tick typhus
         1. *Ricketsia rickettii*
      vi. Scrub typhus
         1. *Orientia tsutsufamushi*
      vii. Ehrlichia
         1. *Ehrlichia* species
         2. *Anaplasma* species
      viii. babesia
      ix. Rocky mountain spotted fever
         1. *Rickettsia rickettsii*
      x. Lyme disease
         1. *Borrelia bergdorferi*

TABLE 1-continued

Specimens, clinical syndromes, and pathogens that can be tested with the present methods

- xi. Syphilis
    1. *Treponema pallidum*
- xii. Bartonellosis- *bartonella* species
- xiii. Leprospirosis- *leptospira interrogans*
- xiv. Relapsing fever
- xv. HIV 4. joint fluid
   a. prosthetic joint infection
      i. *staphylococcus aureus*
      ii. coagulase negative *staphylococcus*
      iii. *streptococcus viridans*
      iv. *pseudomonas aeruginosa*
      v. *enterococcus faecium*
      vi. *enterococcus faecalis*
      vii. *E. coli*
      viii. *Klebsiella pneumoniae*
      ix. *Klebsiella oxytoca*
      x. *Candida albicans*
      xi. *Candida krusei*
      xii. *Candida glabrata*
      xiii. *Propionobacteriuma acnes*
      xiv. *peptostreptococcus*
   b. septic arthritis
      i. *staphylococcus aureus*
      ii. *streptococcus pyogenes*
      iii. *streptococcus agalactiae*
      iv. *neisseria gonorrhea*
      v. *e. coli*
      vi. *pseudomonas aeruginosa*
   c. Lyme arthritis
      i. Lyme disease –> *borrelia bergdorferi*

5. CSF
   a. Meningitis
      i. Bacterial
         1. *Streptococcus pneumoniae*
         2. *Neissseria meningitides*
         3. *Haemophilus influenzae*
         4. *Listeria monocytogenes*
         5. *E. coli*
         6. *Streptococcus agalactiae*
         7. *Propionobacterium acnes*
         8. *Staphylococcus aureus*
         9. Coagulase negative *staphylococcus*
         10. *Enterococcus*
         11. *Klebsiella pneumoniae*
         12. *Pseudomonas aeruginosa*
         13. *Salmonella* species
         14. *Acinetobacter* species
         15. *Streptococcus viridans*
         16. *Streptococcus bovis*
         17. *Fusobacterium* species
         18. *Nocardia* species
         19. *Mycobacterium tuberculosis*
         20. *Streptococcus pyogenes*
      ii. Viral:
         1. Herpes viruses
         2. Enteroviruses
      iii. Spirochetal
         1. Lyme disease
            a. *Borrelia bergdorferi*
         2. Syphilis
            a. *Treponema pallidum*
      iv. Parasites:
         1. *Naegleria fowleri*
         2. *Angiostrongylus cantonensis*
         3. *Bayliascaris procyonis*
         4. *Strongyloides stercoralis*
      v. Fungal
         1. *Croptococcus* species
         2. *Coccidiodes immitis*
         3. *histoplasma*
   b. Encephalitis
      i. Viral:
         1. herpes simplex I
         2. herpes simplex II
         3. human herpes virus 6
         4. varicella zoster virus TABLE 1-continued Specimens, clinical syndromes, and pathogens that can be tested with the present methods 5. Lymphocytic choriomeningitis
         6. Enterovirus
         7. Eastern equine encephalitis virus
         8. Western equine encephalitis virus
         9. Venezuelan equine encephalitis virus
         10. West nile virus
         11. St louis encephalitis virus
         12. Murray valley encephalitis virus
         13. Japanese encephalitis virus
         14. Dengue virus
         15. La crosse virus
         16. Rift valley fever virus
         17. Nipah virus
         18. Lassa fever virus
         19. Rabies virus
         20. Adenovirus
         21. Epstein barr virus 6. Cervical/vaginal swab:
   a. Cervicitis
      i. *Neisseria gonorrhea*
      ii. *Chlamydia trachomatis*
      iii. *trichomoniasis*
   b. Colonization (risk for neonatal sepsis/meningitis)
      i. *Streptococcus agalactiae*

7. Stool:
   a. Antibiotic associated diarrhea:
      i. *Clostridium difficile* associated diarrhea
         1. *Clostridium difficile*
      ii. *Klebsiella oxytoca* associated diarrhea
         1. *Klebsiella oxytoca*
   b. Dysentery
      i. Bacterial:
         1. *Salmonella typhimurium*
         2. *Shigella species*
         3. *Campylobacter jejuni*
      ii. Parasitic:
         1. *Entamoeba hystolytica*
   c. Diarrhea:
      i. Bacterial:
         1. *E. coli*
         2. *Bacillus cereus*
         3. *Vibrio cholera*
         4. *Vibrio parahaemolyticus*
         5. *Clostridium perfringens*
      ii. Parasitic:
         1. *Giardia lamblia*
         2. *Cryptosporidia*
         3. *Microsporidia*
         4. *Isospora belli*
         5. *cyclospora*
         6. *Entamoeba histolytica*
      iii. Viral:
         1. Enteroviruses
         2. Noroviruses
         3. Rota viruses
         4. Astroviruses
         5. caliciviruses
         6. Adenovirus 8. Biliary fluid
   a. Cholangitis
      i. Bacterial:
         1. *Klebsiella oxytoca*
         2. *Escherechia coli*
         3. *Enterococcus* species
         4. *enterobacter*
      ii. Parasitic:
         1. *Clonorchis sinensis*
         2. *Opisthorchis* species
         3. *Fasciola hepatica*
         4. *Ascaris lumbrigoides*

9. Pleural fluid
   a. Empyema

10. Bone biopsy:
    a. Osteomyelitis
       i. Bacterial:
          1. *Staphylococcus auerus*
          2. Coagulase negative *Staphylococcus*

TABLE 1-continued

Specimens, clinical syndromes, and pathogens that can be tested with the present methods

- 3. *Enterococcus* species
- 4. *Streptococcus* species
- 5. *Pseudomonas aeruginosa*
- 6. *Enterobacter* species
- 7. *Proteus* species
- 8. *E. coli*
- 9. *Serratia* species
- 10. *Peptostreptococcus* species
- 11. *Clostridium* species
- 12. *Bacteroides* species
- 13. *Mycobacterium tuberculosis*
- 14. *Mycobacterium avium complex*
- 15. *Salmonella* species
- 16. *Actinomyces* species
  - ii. Fungal:
    1. *Candida* species
    2. *Blastomyces*
    3. *coccidioides*
11. Peritoneal fluid
    a. Bacterial peritonitis (primary and peritoneal dialysis associated]
       i. *E. coli*
       ii. *Klebsiella pneumoniae*
       iii. *Streptococcus pneumoniae*
       iv. *Staphylococcus aureus*
       v. Coagulase negative *staphylococcus*
       vi. *Bacteroides* species
       vii. *Clostridium perfringens*
       viii. *Acinetobacter*
       ix. *Enterobacter*
       x. *Proteus mirabilisa*
       xi. *Pseudomonas aeruginosa*
    b. Fungal peritonitis
       i. *Candida* species
12. Pericardial fluid:
    a. Infectious pericarditis
       i. Bacteria:
          1. *Staphylococcus aureus*
          2. *Streptococcus pneumoniae*
          3. *Neisseria meningitides*
          4. *Haemophilus influenzea*
          5. *Salmonella* species
          6. *Pseudomonas aeruginosa*
          7. *Mycobacterium tuberculosis*
       ii. Fungal:
          1. *Histoplasma capsulatum*
          2. *Candida* species
          3. *Aspergillus* species
          4. *Cryptococcus neoformans*
       iii. Viral:
          1. HIV
          2. Influenza
          3. Mumps
          4. Varicella zoster virus
          5. Epstein barr virus
13. Liver biopsy tissue:
    a. Hepatitis:
       i. Viral:
          1. Hepatitis A
          2. Hepatitis B
          3. Hepatitis C
          4. Hepatitis D
          5. Hepatitis E
          6. Hepatitis G
          7. Herpes simplex virus
          8. Cytomegalovirus
14. Lung biopsy:
    a. Pulmonary nodule
       i. Bacterial:
          1. *Nocardia* species
          2. *Mycobacterium tuberculosis*
          3. *Mycobacterium avium complex*
          4. *Mycobacterium abscessus*
          5. *Actinomyces* species
       ii. Fungal:
          1. *Cryptococcus neoformans*
          2. *Blastomyces*
          3. *Histoplasma capsulatum*

TABLE 1-continued

Specimens, clinical syndromes, and pathogens that can be tested with the present methods 4. *Coccidiodes immitis*
          5. *Aspergillus* species
          6. *Rhizopus* species
          7. *Mucor* species
15. Brain biopsy: mass lesion
    a. Bacterial abscess/lesion:
       i. *Streptococcus anginosis*
       ii. *Bacteroides* species
       iii. *Prevotella* species
       iv. *E. coli*
       v. *Klebsiella* species
       vi. *Enterobacter* species
       vii. *Acinetobacter* species
       viii. *Citrobacter* species
       ix. *Staphylococcus* aureus
       x. *Haemophilus influenzae*
       xi. *Fusobacterium* species
       xii. *Streptococcus pneumoniae*
       xiii. *Actinomyces* species
       xiv. *Nocardia* species
       xv. *Propionobacterium acnes*
    b. Fungi:
       i. *Aspergillus* species
       ii. *Mucor* species
       iii. *Blastomyces*
       iv. *Candida* species
    c. Parasites:
       i. *Schistosomiasis*
       ii. *Toxoplasma gondii*
16. Lymph node biopsy:
    a. Lymphadenitis:
       i. Bacterial:
          1. *Mycobacterium tuberculosis*
          2. *Mycobacterium avium* complex
          3. *Mycobacteriums scrofulaceum*
          4. *Brucella* spcesis
          5. *Treponema pallidum*
          6. *Yersinia pestis*
          7. *Francisella tularensis*
          8. *Bartonella henslae*
          9. *Lymphogranuloma venereum*
             a. *Chlamydia trachomatis*
17. Esophageal biopsy
    a. Esophageal biopsy
       i. Esophagitis
          1. Fungal:
             a. *Candida* species
          2. Viral
             a. Herpes simplex virus
             b. Cytomegalovirus
18. Colonic biopsy:
    a. Diarrhea:
       i. Cytomegalovirus
19. Gastric biopsy:
    a. Peptic ulcer disease and gastritis
       i. *Helicobacter pylori*
20. small bowel biopsy:
    a. whipple's disease: *tropheryma whipplei*
21. myocardial biopsy:
    a. myocarditis:
       i. viral:
          1. coxsackie viruses
          2. echoviruses
          3. adenovirus
          4. Epstein barr virus
          5. Cytomegalovirus
          6. HIV
       ii. Parasites:
          1. *Toxoplasma gondii*
          2. *Trypanosoma cruzi*
          3. *Trichinella spiralis*
          4. *Toxocara canis*
22. Skin biopsy:
    a. disseminated fungal infection:
       i. *coccidioides*
       ii. *fusarium* species
       iii. *blastomyces*

TABLE 1-continued

Specimens, clinical syndromes, and pathogens that can be tested with the present methods iv. *histoplasma*
v. *aspergillus* species
vi. *Cryptococcus*
vii. *Penicillium marneffei*
viii. *Mucor* species 23. Sinus biopsy:
   a. Mucormycosis:
      i. *Mucor* species

TABLE 2

| Organism | RefSeq | nt | Gene | alternate name | GeneID |
|---|---|---|---|---|---|
| *E. coli* organism ID | NC_000913.2 | 103155 to 103985 | ftsQ | | 944823 |
| | NC_0009132 | 100765 to 102240 | murC | | 946153 |
| | NC_000913.2 | 1108558 to 1110093 | opgG | | 945005 |
| | NC_000913.2 | 1078528 to 1080036 | putP | | 945602 |
| | NC_000913.2 | 108279 to 110984 | secA | | 944821 |
| | NC_000913.2 | 1009187 to 1011094 | uup | | 945566 |
| *Staphylococcus aureus* organism ID | NC_007793.1 | 1229595 to 1230521 | fabD | | 3914203 |
| | NC_007793.1 | 1604865 to 1605650 | proC | | 3914537 |
| | NC_007793.1 | 586097 to 589648 | rpoB | | 5776819 |
| | NC_007793.1 | 215727 to 216911 | rocD | | 3914607 |
| | NC_007793.1 | 986970 to 987365 | spxA | | 3913388 |
| | NC_007793.1 | 994970 to 995779 | ppnK | | 3914724 |
| | NC_007793.1 | 1010345 to 1011907 | prfC | | 3914032 |
| | NC_007793.1 | 1142688 to 1144469 | uvrC | | 3913389 |
| | NC_007793.1 | 1187077 to 1189830 | ileS | | 3914067 |
| | NC_007793.1 | 1195628 to 1196509 | pyrB | | 3913022 |
| | NC_007793.1 | 1245088 to 1245972 | rbgA | | 3914854 |
| *Klebsiella pneumoniae* organism ID genes | NC_011283.1 | 3688745 to 3689062 | clpS | | 6935035 |
| | NC_011283.1 | 3652997 to 3653284 | ihfB | | 6936866 |
| | NC_011283.1 | 3679404 to 3679898 | lrp | | 6938832 |
| | NC_011283.1 | 4693235 to 4694176 | mraW | | 6936882 |
| *Pseudomonas aeruginosa* organism ID | NC_002516.2 | 4478979 to 4480139 | dacC | | 878956 |
| | NC_002516.2 | 4477974 to 4478627 | lipB | | 878952 |
| | NC_002516.2 | 4498488 to 4499843 | mpl | | 879000 |
| | NC_002516.2 | 4486847 to 4488112 | proA | | 878970 |
| | NC_002516.2 | 4481230 to 4482252 | sltB1 | | 878946 |
| *Enterococcus faecalis* organism ID | NC_004668.1 | 2760409 to 2761338 | fabD | | 1201730 |
| | NC_004668.1 | 923358 to 925273 | pyrroline reductase | | 1199849 |
| | NC_004668.1 | 3108782 to 3112405 | rpoB | | 1202073 |
| *Streptococcus pyogenes* organism ID | NC_002737.1 | 1129645 to 1130586 | birA | | 901436 |
| | NC_002737.1 | 1161365 to 1162393 | queA | | 901464 |
| | NC_002737.1 | 10951 to 12237 | hpt | | |
| | NC_002737.1 | 1340476 to 1341417 | cysM | | 901866 |
| | NC_002737.1 | 1509476 to 1510441 | scrR | | 902038 |
| | NC_002737.1 | 139268 to 141043 | ntpA | | 900480 |
| | NC_002737.1 | 1528370 to 1530823 | recD | | |
| | NC_002737.1 | 163947 to 164651 | araD | | 900502 |
| *Streptococcus pneumoniae* organism ID | NC_011900.1 | 2048720 to 2049427 | phoP | | 7328038 |
| | NC_011900.1 | 2125295 to 2126311 | arcB | | 7328652 |
| | NC_011900.1 | 291547 to 291864 | ftsL | | 7328131 |
| | NC_011900.1 | 634520 to 635149 | thiE | | 7329171 |
| | NC_011900.1 | 822368 to 823843 | speA | | 7328880 |
| | NC_011900.1 | 878953 to 879894 | prsA | | 7328909 |
| | NC_011900.1 | 967841 to 969100 | murZ | | 7328985 |
| | NC_011900.1 | 1095074 to 1096423 | vicK | | 7329431 |
| *Haemophilus influenzae* organism ID | NC_000907.1 | 1033019 to 1034473 | panF | | 950256 |
| | NC_000907.1 | 1013845 to 1014501 | slmA | | 949937 |
| | NC_000907.1 | 1027535 to 1027984 | aroQ | | 949969 |
| | NC_000907.1 | 1026452 to 1027477 | menC | | 949968 |
| | NC_000907.1 | 1063986 to 1064345 | rnpA | | 950612 |
| | NC_000907.1 | 1086136 to 1087137 | bioB | | 950009 |
| | NC_000907.1 | 1098172 to 1099116 | serB | | 949401 |
| | NC_000907.1 | 104277 to 105274 | hitA | | 950998 |
| *M. tuberculosis* species-specific organism ID | NC_000962.2 | 2223343 to 2224029, complement | Rv1980c | | 885925 |
| | NC_000962.2 | 1574510 to 1574767, complement | rv1398c | | 886759 |
| | NC_000962.2 | 2278498 to 2278932, complement | rv2031c | | 887579 |
| *M. avium/paratuberculosis* organism ID | AE016958 | 2349935 to 2350858 | MAP_2121c | | |
| | NC_008595.1 | 3393700 to 3394494 | MAV_3252 (MAP_1263) | | |
| | NC_008595.1 | 3340393 to 3359031 | MAV_3239 (MAP1242) | | |
| | NC_008595.1 | 1561314 to 1562966 | MAV_1600 (MAP2380) | | |

TABLE 2-continued

| Organism | RefSeq | nt | Gene | alternate name | GeneID |
|---|---|---|---|---|---|
| *M. tuberculosis, M. avium,* | NC_000962.2 | 1852273 to 1852878 | rv1641 (MAP1352, MAV_3127) | | 885478 |
| *M. kansasii* organism ID | NC_000962.2 | 4025056 to 4025544, complement | Rv3583c (MAV_0570, MAP0475) | | 887854 |
| malaria organism ID | AF179422.1 | | Pfg27 | | |
| (*P. falciparum*) | AF356146 .1 | | Pfs48/45 | | |
| | PFI1020c.1 | | PFI1020c | | 813484 |
| | PFA0660w.1 | | PFA0660w | | 813268 |
| | PFA0635c.1 | | PFA0635c | | 813262 |
| | PFA0130c.1 | | PFA0130c | | 813163 |
| | PF11_0282.1 | | PF11_0282 | | 810829 |
| | PFE0660c.1 | | PFE0660c | | 812947 |
| | PFC0800w.1 | | PFC0800w | | 814495 |
| | PFL2520w.1 | | PFL2520w | | 811554 |
| | XM_001349171.1 | | PF07_0128 | | 2654998 |
| | PF10_0346.1 | | PF10_0346 | | 810503 |
| | PF13_0233.1 | | PF13_0233 | | 814200 |
| | PFA0110w.1 | | PFA0110w | | 813159 |
| | PFD1170c.1 | | PFD1170c | | 812429 |
| | PF07_0006.1 | | PF07_0006 | | 2654973 |
| | PF11_0512.1 | | PF11_0512 | | 811044 |
| influenza organism ID | CY052331 | | matrix+ A | | |
| | CY052331 | | matrix+ B | | |
| | CY052331 | | matrix+ C | | |
| | CY052331 | | matrix− A | | |
| | CY052331 | | matrix− B | | |
| | CY052331 | | matrix− C | | |
| HIV organism ID | AF033819 | 336-1838 | gag A | | 155030 |
| | AF033819 | 336-1838 | gag B | | 155030 |
| | AF033819 | 336-1838 | gag C | | 155030 |
| | AF033819 | 336-1838 | gag D | | 155030 |
| | AF033819 | 5516-5591; 7925-8199 | rev A | | 155908 |
| | AF033819 | 5516-5591; 7925-8199 | rev B | | 155908 |
| | AF033819 | 5516-5591; 7925-8199 | rev C | | 155908 |
| | AF033819 | 5516-5591; 7925-8199 | rev D | | 155908 |
| HSV2 organism ID | EU106421 | | gpG A | | |
| | EU106421 | | gpG B | | |
| | EU106421 | | gpG C | | |
| | EU106421 | | gpG D | | |
| *E. coli* ampicillin | NC_000913.2 | 1724047 to 1724646 | b1649 | | 946166 |
| resistance genes | NC_000913.2 | 354146 to 355405 | codB | | 944994 |
| | NC_000913.2 | 2873443 to 2874351 | cysD | | 947217 |
| | NC_000913.2 | 3815783 to 3816607 | dinD | | 948153 |
| | NC_000913.2 | 594823 to 596196 | ylcB | | 946288 |
| *E. coli* aminoglycoside | NC_000913.2 | 1133025 to 1133780 | flgF | | 945639 |
| resistance genes | NC_000913.2 | 2873443 to 2874351 | cysD | | 947217 |
| | NC_000913.2 | 4054648 to 4056057 | glnA | | 948370 |
| | NC_000913.2 | 1108558 to 1110093 | opgG | | 945005 |
| | NC_000913.2 | 103155 to 103985 | ftsQ | | 944823 |
| | NC_000913.2 | 1724047 to 1724646 | b1649 | | 946166 |
| | NC_000913.2 | 2820730 to 2821791 | recA | | 947170 |
| | NC_000913.2 | 3815783 to 3816607 | dinD | | 948153 |
| *E. coli* fluoroquinolone | NC_000913.2 | 29651 to 30799 | carA | | 949025 |
| resistance genes | NC_000913.2 | 4610434 to 4618849 | deoC | | 948902 |
| | NC_000913.2 | 1133025 to 1133780 | flgF | | 945639 |
| | NC_000913.2 | 3790849 to 3791706 | htrL | | 948137 |
| | NC_000913.2 | 2820730 to 2821791 | recA | | 947170 |
| | NC_000913.2 | 4269072 to 4271894 | uvrA | | 948559 |
| | NC_000913.2 | 2101415 to 2102533 | wbbK | | 946555 |
| | NC_000913.2 | 814962 to 815870 | ybhK | | 945390 |
| | NC_000913.2 | 1009187 to 1011094 | uup | | 945566 |
| | NC_000913.2 | 1148951 to 1149880 | fabD | | 945766 |
| *E. coli* normalizing genes | NC_000913.2 | 1148951 to 1149880 | fabD | | 945766 |
| | NC_000913.2 | 404059 to 404868 | proC | | 945034 |
| | NC_000913.2 | 4183296 to 4179268 | rpoB | | 948488 |
| *Pseudomonas aeruginosa* | NC_002516.2 | 899830 to 900165 | PA 0825 | | 880620 |
| fluoroquinolone resistance | NC_002516.2 | 106321 to 1067817 | PA 0985 | | 877569 |
| | NC_002516.2 | 1385668 to 1384361 | cobB | | 881727 |
| | NC_002516.2 | 4088904 to 4090094 | dxr | | 880464 |
| | NC_002516.2 | 1167488 to 1168237 | flgF | | 878576 |
| | NC_002516.2 | 3367903 to 3368517 | lexA | | 879875 |
| | NC_002516.2 | 4385900 to 4386352 | moaE | | 878985 |
| | NC_002516.2 | 4051564 to 4052604 | recA | | 880173 |
| *Pseudomonas aeruginosa* | NC_002516.2 | 317966 to 318148 | PA 0284 | | 879699 |
| tobramycin resistance genes | NC_002516.2 | 674667 to 675026 | PA 0613 | | 878382 |
| | NC_002516.2 | 2200685 to 2202652 | PA 2012 | | 879012 |
| | NC_002516.2 | 3508717 to 3509166 | PA 3126 | | 882640 |
| | NC_002516.2 | 4407760 to 4408734 | PA 3932 | | 879072 |

TABLE 2-continued

| Organism | RefSeq | nt | Gene | alternate name | GeneID |
|---|---|---|---|---|---|
| | NC_002516.2 | 4671319 to 4672707 | PA 4175 | | 880208 |
| | NC_002516.2 | 5349201 to 5349761 | PA 4762 | | 881766 |
| | NC_002516.2 | 5693138 to 5694481 | hslU | | 881050 |
| *Pseudomonas aeruginosa* normalizing genes | NC_002516.2 | 3326145 to 3327083 | fabD | | 880434 |
| | NC_002516.2 | 434830 to 435651 | proC | | 878413 |
| | NC_002516.2 | 4776544 to 4780627 | rpoB | | 881699 |
| *Staphylococcus aureus* methicillin resistance genes | NC_007793.1 | 39127 to 44133 | mecA | | 3913904 |
| | NC_007793.2 | 39128 to 44133 | mecA | | 3913904 |
| *Enterococcus faecalis* vancomycin resistance genes | NC_008768.1 | 11489 to 12520 | EF vanA | | |
| | NC_008768.1 | 11489 to 12520 | EF vanA | | |
| | NC_008768.1 | | EF vanB | | |
| | NC_008768.1 | | EF vanB | | |
| *Mycobacterium tuberculosis* streptomycin resistance | NC_000962.2 | 907338 to 908018, complement | Rv0813c.1 | Rv0813 | 885395 |
| | NC_000962.2 | 1807298 to 1807762, complement | Rv1608c.1 | bcpB | 885530 |
| | NC_000962.2 | 2075877 to 2078702 | Rv1832.1 | gcvB | 885716 |
| | NC_000962.2 | 3835272 to 3836891, complement | Rv3417c.1 | groEL | 887877 |
| *Mycobacterium tuberculosis* rifampicin resistance | NC_000962.2 | 1777859 to 1778539 | Rv1570.1 | bioD | 886338 |
| | NC_000962.2 | 1805653 to 1806000 | Rv1606 .1 | hisI | 886011 |
| | NC_000962.2 | 2567504 to 2568406 | Rv2296.1 | | 887796 |
| | NC_000962.2 | 2645771 to 2646673, complement | Rv2364c.1 | era | 886027 |
| *Mycobacterium tuberculosis* isoniazid resistance | NC_000962.2 | 2518115 to 2519365 | Rv2245.1 | kasA | 887269 |
| | NC_000962.2 | 2520743 to 2522164 | Rv2247 .1 | accD6 | 887671 |
| | NC_000962.2 | 3153039 to 3154631, complement | Rv2846c.1 | efpA | 888575 |
| | NC_000962.2 | 4116002 to 4116379 | Rv3675 .1 | Rv3675 | 885155 |
| | NC_000962.2 | 4261153 to 4263066, complement | Rv3801c.1 | fadD32 | 886130 |
| *Mycobacterium tuberculosis* fluoroquinolone resistance | NC_000962.2 | 2518115 to 2519365 | Rv2245.1 | kasA | 887269 |
| | NC_000962.2 | 2520743 to 2522164 | Rv2247.1 | accD6 | 887671 |
| | NC_000962.2 | 59122 to 59376 | Rv0055.1 | rpsR | 887022 |
| | NC_000962.2 | 1477628 to 1479118, complement | Rv1317c.1 | alkA | 886916 |
| | NC_000962.2 | 3049052 to 3051424, complement | Rv2737c.1 | recA | 888371 |
| | NC_000962.2 | 3098964 to 3100169, complement | Rv2790c.1 | ltp1 | 888585 |
| | NC_000962.2 | 3676775 to 3681316 | Rv3296.1 | lhr | 887503 |
| *M. tuberculosis* ethambutol | NC_000962.2 | 2279129 to 2280124 | rv2032 | | 887582 |
| | NC_000962.2 | 3134596 to 3135483, complement | rv2827c | | 887707 |
| | NC_000962.2 | 4360199 to 4360546, complement | rv3880c | | 886205 |
| *M. tuberculosis* normalization controls | NC_000962.2 | 759807 to 763325 | Rv0667.1 | rpoB | 888164 |
| | NC_000962.2 | 2223343 to 2224029, complement | Rv1980c.1 | mpt64 | 885925 |
| | NC_000962.2 | 3017835 to 3019421 | Rv2703.1 | sigA | 887477 |
| *Streptococcus agalactiae* organism ID | NC_004368.1 | 113813 to 113862 | tig | gbs0104 | |
| | NC_004368.1 | 116727 to 116776 | pyrG | gbs0106 | |
| | NC_004368.1 | 1796241 to 1796290 | scrR | gbs1736 | |
| | NC_004368.1 | 1930084 to 1930133 | hslO | gbs1865 | |
| | NC_004368.1 | 27753 to 277602 | SglyS | gbs0260 | |
| | NC_004368.1 | 293911 to 293960 | proB | gbs0273 | |
| | NC_004368.1 | 296033 to 296082 | mraW | gbs0275 | |
| | NC_004368.1 | 296975 to 297024 | ftsL | gbs0276 | |
| *Serratia proteamaculans* organism ID | NC_009832 | 1003727 to 1003776 | dkgB | Spro_0904 | 5603647 |
| | NC_009832 | 1043868 to 1043917 | mtnK | Spro_0946 | 5603764 |
| | NC_009832 | 106923 to 106972 | xylF | Spro_0099 | 5605677 |
| | NC_009832 | 1066040 to 1066089 | proA | Spro_0968 | 5605339 |
| | NC_009832 | 1119783 to 1119832 | aroL | Spro_1018 | 5603038 |
| | NC_009832 | 11924 to 11973 | phosphate ABC transporter periplasmic substrate-binding protein PstS | Spro_0012 | 5603657 |
| | NC_009832 | 1170021 to 1170070 | secD | Spro_1063 | 5606770 |
| | NC_009832 | 1181606 to 1181655 | ribD | Spro_1072 | 5606850 |
| *Streptococcus mitis* organism ID | NC_013853.1 | 741 to 790 | dnaA | smi_0001 | 8797427 |
| | NC_013853.1 | 1121903 to 1121952 | mscL | smi_1137 | 8798101 |
| | NC_013853.1 | 298410 to 298459 | purR | smi_0302 | 8799383 |
| | NC_013853.1 | 317077 to 317126 | amiA | smi_0322 | 8799444 |
| | NC_013853.1 | 539539 to 539588 | nanA | smi_0601 | 8797777 |
| | NC_013853.1 | 637090 to 637139 | codY | smi_0687 | 8799389 |
| | NC_013853.1 | 683274 to 683323 | pstS | smi_0732 | 8797867 |

TABLE 2-continued

| Organism | RefSeq | nt | Gene | alternate name | GeneID |
|---|---|---|---|---|---|
| Candida albicans organism ID | NC_007436.1 | 102175 to 102224 | CaJ7_0076 | | 3704032 |
| | NC_007436.1 | 174830 to 174879 | CaJ7_0103 | | 3703998 |
| | NC_007436.1 | 376124 to 376173 | CaJ7_0197 | | 3704134 |
| | NC_007436.1 | 465177 to 465226 | CaJ7_0245 | | 3703842 |
| | NC_007436.1 | 658412 to 658461 | CaJ7_0344 | | 3703873 |
| | NC_007436.1 | 771224 to 771273 | CaJ7_0399 | | 3704050 |
| Acinetobacter baumanii organism ID | NC_009085.1 | 1008527 to 1008576 | fusA | A1S_0868 | 4918267 |
| | NC_009085.1 | 1155941 to 1155990 | lysS | A1S_0998 | 4918633 |
| | NC_009085.1 | 1168069 to 1168118 | isocitrate lyase | A1S_1008 | 4919056 |
| | NC_009085.1 | 1173092 to 1173141 | ureC | A1S_1014 | 4917976 |
| | NC_009085.1 | 1330602 to 1330651 | rnhB | A1S_1140 | 4917576 |
| | NC_009085.1 | 1395212 to 1395261 | pyrB | A1S_1190 | 4919730 |
| | NC_009085.1 | 155583 to 155632 | guaA | A1S_0130 | 4920269 |
| | NC_009085.1 | 1820125 to 1820174 | cmk | A1S_1571 | 4917197 |
| Proteus mirabilis organism ID | NC_010554.1 | 106142 to 106191 | secD | PMI0078 | 6801011 |
| | NC_010554.1 | 1061810 to 1061859 | map1 | PMI0997 | 6802785 |
| | NC_010554.1 | 1070228 to 1070277 | ftnA | PMI1007 | 6802218 |
| | NC_010554.1 | 1078862 to 1078911 | Prc | PMI1016 | 6802734 |
| | NC_010554.1 | 109131 to 109180 | nrdR | PMI0080 | 6802391 |

| Gene | Sequence | SEQ ID NO: |
|---|---|---|
| ftsQ | CGACAGTGTTGGTGAGCGGCTGGGTCGTGTTGGGCTGGATGGAAGATGCGCAACGCCTGCCGCTCTCAAAGCTGGTGTTGACCGGTGAACGCCATTACAC | 1 |
| murC | GAATTGTTACCGCGAGTGGGGCGTCAGACCACGACTTACGGCTTCAGCGAAGATGCCGACGTGCGTGTAGAAGATTATCAGCAGATTGGCCCGCAGGGGC | 2 |
| opgG | TTGTGGATGTGCAGTCGAAAATCTATCTGCGCGATAAAGTCGGCAAACTGGGGGTTGCACCGTTAACCAGTATGTTCCTGTTTGGGCCGAACCAACCGTC | 3 |
| putP | TAGTGTTTAGTTTGCTGGGTAAAGCGCCGTCAGCGGCGATGCAAAAACGCTTTGCCGAGGCCGATGCGCACTATCATTCGGCTCCGCCGTCACGGTTGCA | 4 |
| secA | CTCGGAAATGTATAAACGCGTGAATAAAATTATTCCGCACCTGATCCGTCAGGAAAAAGAAGACTCCGAAACCTTCCAGGGCGAAGGCCACTTCTCGGTG | 5 |
| uup | AACGCTATCACGATATTTCGCGCCTGGTGATGAACGACCCGAGCGAGAAAAATCTCAACGAACTGGCGAAGGTTCAGGAACAGCTGGATCACCACAACCT | 6 |
| fabD | GAGCTAGTAGAAAAAGGTAAATCATTAGGTGCAAAACGTGTCATGCCTTTAGCAGTATCTGGACCATTCCATTCATCGCTAATGAAAGTGATTGAAGAAG | 7 |
| proC | TAACAGCTATCACCGGAAGCGGCCCAGCATTTTTATATCATGTATTCGAGCAATATGTTAAAGCTGGTACGAAACTTGGTCTAGAAAAAGAACAAGTTGA | 8 |
| rpoB | GGAGAAATGGCATTAGGTAGAAACGTAGTAGTTGGTTTCATGACTTGGGACGGTTACAACTATGAGGATGCCGTTATCATGAGTGAAAGACTTGTGAAAG | 9 |
| rocD | AAAGATCCTGAAGGCAATAAATATATGGATATGTTATCTGCATATTCCGC | 10 |
| spxA | AATATTAAAAATGACTGAAGACGGTACTGATGAAATCATTTCTACACGTT | 11 |
| ppnK | ACAGGTCATTTAGGATTTTATGCGGATTGGTTACCTCATGAAGTTGAAAA | 12 |
| prfC | AAATTAGACCGAGTAGGTAAAGAACCATTTGAATTATTAGATGAAATCGA | 13 |
| uvrC | AAATATTTCGGACCGTATCCGAATGCATATTCTGCTCAAGAAACTAAAAA | 14 |
| ileS | AAATTCAAGAAAATGGGATGCAGAAGATCAATACCATAAAGCGTTAGAA | 15 |
| pyrB | AAATATACAAACTTATCCAAAAGGCAAGTCAATTTAAATCTGGTGAACGT | 16 |
| rbgA | AAACCCTATGATAGATGAAGTTATTAACCAAAAACCACGTGTTGTTATAT | 17 |
| clpS | CAACTGATGCTCACGGTTCACTATGAAGGTAAGGCGATTTGTGGCGTGTTTACCGCGGAAGTGGCGGAGACCAAAGTCGCTATGGTGAATCAGTACGCGA | 18 |
| ihfB | CTCGCACCGGACGTAACCCGAAAACTGGTGATAAAGTCGAACTGGAAGGTAAGTACGTTCCGCACTTTAAGCCCGGGAAAGAATTACGTGACCGCGCCAA | 19 |

| Gene | Sequence | SEQ ID NO: |
|---|---|---|
| lrp | TCATCTGGTTTCCGGTGATTTCGACTATCTGTTGAAAACCCGTGTACCGGATATGTCAGCGTATCGTAAATTACTGGGCGAGACCTTGCTGCGCCTGCCG | 20 |
| mraW | TCATTCGCTGGAAGATCGCATTGTGAAGCGCTTTATGCGTGAGCAAAGCCGCGGTCCGCAGGTTCCGGCGGGAATACCGATGACCGAAGCGCAGCTCAAA | 21 |
| dacC | GCGATCTACGCGCAGAAGGAATTCCTCTGGAACAACATCAAGCAGCCGAACCGCAACCTGCTGCTGTGGCGCGACAAGACCGTCGACGGCCTGAAGACCG | 22 |
| lipB | CCTGCGGCTACGCCGGGATGCCCATGACCCAACTGCGCGACCTGGTTGGGCCGGTGGATTTTGCCGAGGTGTGTACCCGATTGCGCGCTGAGCTCGTCTC | 23 |
| mpl | ACCGCCCGCGCACGGCGATCCTGAACAACCTGGAATTCGACCACGCGGATATCTTCCCCGACCTCGCGGCCATCGAGCGGCAGTTCCACCATCTGGTGCG | 24 |
| proA | AAGTGGATTCCGCTTCGGTGATGGTCAACGCCTCGACCCGCTTCGCCGACGGCTTCGAGTACGGCCTCGGCGCCGAGATCGGGATTTCCACCGACAAGCT | 25 |
| sltB1 | CGATGCGTTTCGTCGGCGACAAGGGCATCGAGTATTGGGTCGGTTTGCCGAACTTCTACGTGATCACCCGCTATAATCGCAGCGCCATGTATGCCATGGC | 26 |
| fabD | AGCTGGTGTGAAGCGAATGATTCCGTTAAATGTGAGTGGCCCTTTCCATACGGCGCTGTTACAACCAGCATCAAAAAAATTGGCTCAGGATTTAGCAAAA | 27 |
| pyrroline reductase | CAAGAAGCACAAATGGCTCTTGGCAATAAAGAAGCCAAAGTTGTTCATGCCATTCCTAATACACCAGTTAGCGTGAATCAAGGCGTGATTGGCGTAGCCT | 28 |
| rpoB | CACAGTTATACAGTTCATGGACCAAACAAACCCATTAGGTGAGTTAACCCATAAACGTCGTCTATCAGCCTTAGGGCCTGGTGGTTTGACTCGTGACCG | 29 |
| birA | AGCCAAGAAGCTGCCAAAGGACGCCTCGATCGGCAATTTTTTTCAGCTAG | 30 |
| queA | ATGGTCATGTGGAATTGCTTTTGCTTAAAAATACACAAGGAGATCAATGG | 31 |
| hpt | ATCAAGAAAAAAATCCGCTTATGATTGGTGTATTAAAAGGATCAGTTCCT | 32 |
| cysM | AACTTTAGCAATAGAACTAGGTGCTTGGATGCCTATGCAATTTAATAACC | 33 |
| scrR | ATTGGGCTACAAGCCTAACAATCTCGCTAGAAGTTTGCAAGGTAAATCAA | 34 |
| ntpA | AGAAATGTTTGACGGTATTCAGCGACCGCTTGATCGTTTTCAAAAAGCAA | 35 |
| recD | ACCATTGACCATATTTTAGAAGACCCAAGCAAATTAGAAACTATCTCTGG | 36 |
| araD | AAATTTACGTGGGGCAATGTCTCTGAAGTTTGTCGTGAATTAGGACGTAT | 37 |
| phoP | ACGACATGGTCGCCAAGCACCGGCAACTGGCCGAGATCATCGCCAGCGAC | 38 |
| arcB | TCACTTGAAAGATTTGAAAAAACGCAATATTCAACACCACTACCTTGCTG | 39 |
| ftsL | CGCGTGTGGAAAAAGCTTTTTACTTTTCCATTGCTGTAACCACTCTTATT | 40 |
| thiE | TGGCGTACATGTAGGTCAAGATGATATTGGTGTTGATGAAATTAGAAAAT | 41 |
| speA | GATTGGTGGAACAACTTCATCGGTGCAGACTATGATTCTGGCAACCTGCA | 42 |
| prsA | AGTTTTTGAAAACAATATGGCTCAGAGCTTGATGATAAAGAGGTTGATG | 43 |
| murZ | ATTTTTATGGGAGCCTCTTAGGCCGTTTTGGTGAAGCGACAGTTGGTCTA | 44 |
| vicK | ATTTGATTGCAGGAGATTATTCCAAGGTTCTTGATATGCAAGGTGGGTCT | 45 |
| panF | AAAGAAGCGGGCAATATGGTGGATCTCGACTCCAACCCGACCAAGTTGAT | 46 |
| slmA | AGCAAGTGCTTACAGTATTGATACATATGCTTCATTCTGAACGTGGAATG | 47 |
| aroQ | CTTAAATATGTTAGGGGCTCGCGAGCCAAAACATTATGGCAGTATTTCTC | 48 |
| menC | ATCCCCGTTGATAGCCAACTTATTCTGCGTGATCGTTTTTTAAAACGCCG | 49 |
| rnpA | AAATTACAATCCTTGCTAGAAAAAATAATCTTGAACATCCGCGTTTAGGT | 50 |
| bioB | CATCCAAGTGTAGAATATTGGTCTGTTTGCAAAGTTGAGGCGTTATTTGA | 51 |
| serB | ATACGGCACAAAGTTGGACATAACTAAGCTAGAAAAATTTCAACAAAGT | 52 |

-continued

| Gene | Sequence | SEQ ID NO: |
|---|---|---|
| hitA | AGCCGCTACGGCTGTGGCAAAAGCCTTTGAACAGGAAACAGGCATTAAAG | 53 |
| Rv1980c | ATCGATAGCGCCGAATGCCGGCTTGGACCCGGTGAATTATCAGAACTTCGCAGTCACGAACGACGGGGTGATTTTCTTCTTCAACCCCGGGGGAGTTGCTG | 54 |
| rv1398c | GGGACGACCTTGCATCGGACCTGCAGGCTATAAACGATTCGTTCGGCACGCTTCGCCACCTGGATCCGCCGGTGCGTCGCTCCGGTGGTCGTGAACAGCA | 55 |
| rv2031c | AGCGCCACCCGCGGTCCCTCTTCCCCGAGTTTTCTGAGCTGTTCGCGGCCTTCCCGTCATTCGCCGGACTCCGGCCCACCTTCGACACCCGGTTGATGCG | 56 |
| MAP_2121c | ACCTGGCGCGGTATTCCGCTGATCCCGTCGGACAAGGTGCCGGTGGAGGACGGCAAGACGAAGTTCATCCTGGTCCGCACCGGCGAGGAACGTCAGGGCG | 57 |
| MAV_3252 (MAP_1263) | CGGCGCCCAGAGTGTCTACGGCGTGGTCCCCATGTGCGCGGTGATATCGGCGCTCTTCGGCTCCCTCGGCAACTCGGTGGGCATCACCATGGACCGCCAG | 58 |
| MAV_3239 (MAP1242) | ATCGACCCCGGATTGCCCTCGGCGCGAATCGATTTCATGCTCGCCGACGCCGTGCCCGTCGTCACGGTCACCACCGCCGAACTGCGCGCTTCGGCCGGCG | 59 |
| MAV_1600 (MAP2380) | GTCGACGCCGGAGAATTGATCGCCCACGCATCGAATTCGCTGGCGCGCTACAAGCTTCCCAAGGCGATCGTGTTCCGTCCGGTGATCGAGCGCAGCCCGT | 60 |
| rv1641 (MAP1352, MAV_3127) | GTCAAAGAACAAAAGCTGCGACCAAAGATTGACGATCACGATTACGAGACCAAAAAGGGTCACGTCGTCCGCTTCTTGGAGGCGGGATCGAAGGTCAAGG | 61 |
| Rv3583c (MAV_0570, MAP0475) | GAACAAAAGAGTATCTCGTCTTGAAAGTTGCGCAGGGCGACCTGACAGTACGAGTTCCCGCTGAAAACGCCGAATACGTCGGTGTTCGCGATGTCGTCG | 62 |
| Pfg27 | GGTACAAAAGGATAGTGCCAAGCCCTTGGATAAATTTGGAAATATCTATGATTATCACTATGAGCATGAAACACATGCCCCTCTCTCACCTCGTATTAGA | 63 |
| Pfs48/45 | AGAGTTGAAACTGATATATCGGAATTAGGTTTAATTGAATATGAAATAGAAGAAAATGATACAAACCCTAATTATAATGAAAGGACAATAACTATATCTC | 64 |
| PFI1020c | AATATGACAGATAACATAACGCTAAAAACACCGGTAATATCATCCTATGGATACAGTAACGGGACATAAGATGTCAATAGCTTTAGCTTTGAGCGGTG | 65 |
| PFA0660w | ACATATACAAATAGATGAGGTGGTAAAACCTGACACAAAGAAGGTTATAAAAAATGAAGGAATGCCTTACTCAAGAGATCAAGTATTAGAGGAAATTTG | 66 |
| PFA0635c | ACAGGGAAATGATAAACATATAGATAGTGAACATAATGGAATAAATAAAATGTACAAAGAAACAATACATAAAACACTAACATCTGATGTATCAACAGAA | 67 |
| PFA0130c | CCCAATACCTACATGTGGAGCTTCTAGGGTTATGGAGAAATGTCAAAAGATGTATAAGGTGGTTATAAAACCGAAGGAGAAGGACGATAAAGTGGATAAT | 68 |
| PF11_0282 | CGCTTAGCTAATTCAATTGGACTAATTGATGCAGGTTATAGAGGAGAAATTATTGCCGCCTTGGATAATACTAGTGACCAAGAGTATCACATTAAAAAAA | 69 |
| PFE0660c | GGGACGAAGGGGATTTCGACAACAATTTAGTTCCTCACCAATTAGAAAATATGATTAAAATAGCCTTAGGAGCATGTGCAAAATTAGCAACCAAATATGC | 70 |
| PFC0800w | ATTATCTTACCTGTGAATATAAAAAATGCTATGGAAAAACAAGCTGAAGCAGAAAGAAGAAAAAGAGCTGAAATTTTACAAAGTGAAGGAGAAAGAGAAA | 71 |
| PFL2520w | TACTTTATCCCGTGATGGTAAGAATGATATTGAAGAAGAAGAAGAAGATGAGGAAGATGAAAAAAATATAAACAACTCCCAAGATACCACATTAAGT | 72 |
| PF07_0128 | TGAAGGACCAAAAGGAAATGAACAAAAAAACGTGATGACGATAGTTTGAGTAAAATAAGTGTATCACCAGAAATTCAAGACCTGAAACTGATGCTAAA | 73 |
| PF10_0346 | GAGGTGCTCCTCAAAATGGAGCTGCAGAAGATAAAAAGACAGAATATTTACTAGAACAAATAAAAATTCCATCATGGGATAGAAATAACATCCCCGATGA | 74 |
| PF13_0233 | ATACACCACTGCTGTTCCCCTTATTGTTGCAATAAACCCATACAAGGATTTAGGAAACACAACTAATGAATGGATTCGTAGATATCGTGATACAGCTGAT | 75 |
| PFA0110w | AGAACCAACTGTTGCTGAAGAACACGTAGAAGAACCAGCTAGTGATGTTCAACAAACTTCAGAAGCAGCTCCAACAATTGAAATCCCCGATACATTATAT | 76 |
| PFD1170c | ACTATTAAAGCTATGGAAATTATATGGGAAGCTACCATGAACAATGAAAGGAGAAATATGCTGCCACTAAACGTAGCATGCTCAGATATTATGATGATT | 77 |

-continued

| Gene | Sequence | SEQ ID NO: |
|---|---|---|
| PF07_0006 | ATATACCAGAAAGTAGTAGTACATATACAAATACAAGGTTAGCAGCAAATAACAGTACAACTACAAGCACTACAAA AGTAACAGATAATAATAAAACAAA | 78 |
| PF11_0512 | ATTCAAACCACTTATCGTAGATGATGAACTACTTGAATACAACCAAAAGGTTCATAACATAGGAAGAAATGGAGAA GACATTTTAACTGCTATGCAAACA | 79 |
| matrix + A | CTCACCGTGCCCAGTGAGCGAGGACTGCAGCGTAGACGCTTTGTCCAAAATGCCCTTAATGGGAATGGGGATCCAA ATAATATGGACAGAGCAGTTAAAC | 80 |
| matrix + B | ATCGAAAGCTTAAGAGGGAGATAACATTCCATGGGGCCAAAGAAATAGCACTCAGTTATTCTGCTGGTGCACTTGC CAGTTGTATGGGACTCATATACAA | 81 |
| matrix + C | GCAGGCAATGAGAGCCATTGGGACTCATCCTAGCTCTAGCACTGGTCTGAAAAATGATCTCCTTGAAAATTTGCAG GCCTATCAGAAACGAATGGGGGTG | 82 |
| matrix - A | GCTGACAAAATGACCATCGTCAGCATCCACAGCATTCTGCTGTTCCTCTCGATATTCTTCCCTCATAGACTCTGGT ACTCCTTCCGTAGAAGGCCCTCTT | 83 |
| matrix - B | GGTTGTTGTTACCATTTGCCTATGAGACTTATGCTGGGAGTCGGCAATCTGTTCACAGGTTGCGCATATAAGGCCA AATGCTGATTCGGTGGTCACAGCC | 84 |
| matrix - C | ACACAAATCCTAAAATCCCCTTAGTCAGAGGTGACAGGATCGGTCTTGTCTTTAGCCATTCCATGAGAGCCTCAAG ATCGGTATTCTTTCCAGCAAAGAC | 85 |
| gag A | AAACATATAGTATGGGCAAGCAGGGAGCTAGAACGATTCGCAGTTAATCCTGGCCTGTTAGAAACATCAGAAGGCT GTAGACAAATACTGGGACAGCTAC | 86 |
| gag B | CAGCTGACACAGGACACAGCAATCAGGTCAGCCAAAATTACCCTATAGTGCAGAACATCCAGGGGCAAATGGTACA TCAGGCCATATCACCTAGAACTTT | 87 |
| gag C | ATCAGAAGGAGCCACCCCACAAGATTTAAACACCATGCTAAACACAGTGGGGGGACATCAAGCAGCCATGCAAATG TTAAAAGAGACCATCAATGAGGAA | 88 |
| gag D | TAGAGACTATGTAGACCGGTTCTATAAAACTCTAAGAGCCGAGCAAGCTTCACAGGAGGTAAAAAATTGGATGACA GAAACCTTGTTGGTCCAAAATGCG | 89 |
| rev A | GAGACAGCGACGAAGAGCTCATCAGAACAGTCAGACTCATCAAGCTTCTCTATCAAAGCAACCCACCTCCCAACCC CGAGGGGACCCGACAGGCCCGAAG | 90 |
| rev B | CGACAGGCCCGAAGGAATAGAAGAAGAAGGTGGAGAGAGAGACAGAGACAGATCCATTCGATTAGTGAACGGATCC TTGGCACTTATCTGGGACGATCTG | 91 |
| rev C | CTTATCTGGGACGATCTGCGGAGCCTGTGCCTCTTCAGCTACCACCGCTTGAGAGACTTACTCTTGATTGTAACGA GGATTGTGGAACTTCTGGGACGCA | 92 |
| rev D | GAACTTCTGGGACGCAGGGGTGGGAAGCCCTCAAATATTGGTGGAATCTCCTACAGTATTGGAGTCAGGAACTAA AGAATAG | 93 |
| gpG A | TGGCGCACCCAACGCAACGTATGCGGCCCATGTGACGTACTACCGGCTCACCCGCGCCTGCCGTCAGCCCATCCTC CTTCGGCAGTATGGAGGGTGTCGC | 94 |
| gpG B | CTGCTGGTGCCGATCTGGGACCGCGCCGCGGAGACATTCGAGTACCAGATCGAACTCGGCGGCGAGCTGCACGTGG GTCTGTTGTGGGTAGAGGTGGGCG | 95 |
| gpG C | CCTACCACGCGTCGCTTTTGCTCCCCAGAGCCTGCTGGTGGGATTACGGGCCGCACGTTTATTCGGATGGCACGA CCCACGGAAGACGGGGTCCTGCCG | 96 |
| gpG D | CCCCTGTTCTGGTTCCTAACGGCCTCCCCTGCTCTAGATATCCTCTTTATCATCAGCACCACCATCCACACGGCGG CGTTCGTTTGTCTGGTCGCCTTGG | 97 |
| b1649 | GCTAAGCGAATTACTAAAAACCGCTGAAGTGCCGAAAGGGTCCTTCTATCACTACTTTCGCTCTAAAGAAGCGTTT GGCGTTGCCATGCTTGAGCGTCAT | 98 |
| codB | GTCGGCTGGTTGACCTTCCTTTCGGCAGCTATTCCTCCAGTGGGTGGCGTGATCATCGCCGACTATCTGATGAACC GTCGCCGCTATGAGCACTTTGCGA | 99 |
| cysD | CAAATCCGGTGATGCTCTACTCTATCGGTAAAGATTCCAGCGTCATGCTGCATCTGGCGCGCAAGGCGTTTTATCC AGGTACGCTGCCTTTCCCGTTGCT | 100 |
| dinD | TGGATTAGATCAGAAAGCTATTCATCAGCGGAAGGGGCTGAAAAAGAATCAGAAGATCCTGGATCATATGGGTTCA ACAGAACTGGCGGCTAATCTCTTT | 101 |
| ylcB | GAATACCGCCACGACACGGGAGTTTTCGACCGGCCTTAACGCCAGCTTTGACCTCGATTTTTTCGGTCGCTTAAAG AACATGAGCGAAGCCGAGCGACAA | 102 |

| Gene | Sequence | SEQ ID NO: |
|---|---|---|
| flgF | GAAGGCAGTAACGTCAATGCCGTTGCGGCAATGAGCGACATGATTGCCAGCGCGCGGCGTTTTGAAATGCAGATGAAGGTGATCAGCAGCGTCGATGATA | 103 |
| cysD | CAAATCCGGTGATGCTCTACTCTATCGGTAAAGATTCCAGCGTCATGCTGCATCTGGCGCGCAAGGCGTTTTATCCAGGTACGCTGCCTTTCCCGTTGCT | 104 |
| glnA | TTCGGTAAAACCGCGACCTTTATGCCAAAACCGATGTTCGGTGATAACGGCTCCGGTATGCACTGCCACATGTCTCTGTCTAAAAACGGCGTTAACCTGT | 105 |
| opgG | TTGTGGATGTGCAGTCGAAAATCTATCTGCGCGATAAAGTCGGCAAACTGGGGGTTGCACCGTTAACCAGTATGTTCCTGTTTGGGCCGAACCAACCGTC | 106 |
| ftsQ | CGACAGTGTTGGTGAGCGGCTGGGTCGTGTTGGGCTGGATGGAAGATGCGCAACGCCTGCCGCTCTCAAAGCTGGTGTTGACCGGTGAACGCCATTACAC | 107 |
| b1649 | GCTAAGCGAATTACTAAAAACCGCTGAAGTGCCGAAAGGGTCCTTCTATCACTACTTTCGCTCTAAAGAAGCGTTTGGCGTTGCCATGCTTGAGCGTCAT | 108 |
| recA | AACACGCTGCTGATCTTCATCAACCAGATCCGTATGAAAATTGGTGTGATGTTCGGTAACCCGGAAACCACTACCGGTGGTAACGCGCTGAAATTCTACG | 109 |
| dinD | TGGATTAGATCAGAAAGCTATTCATCAGCGGAAGGGGCTGAAAAAGAATCAGAAGATCCTGGATCATATGGGTTCAACAGAACTGGCGGCTAATCTCTTT | 110 |
| carA | GATGAAGAATCTTCTCAGGTACATGCACAAGGTCTGGTGATTCGCGACCTGCCGCTGATTGCCAGCAACTTCCGTAATACCGAAGACCTCTCTTCTTACC | 111 |
| deoC | CAATCGCCTACGGTGCTGATGAAGTTGACGTTGTGTTCCCGTACCGCGCGCTGATGGCGGGTAACGAGCAGGTTGGTTTTGACCTGGTGAAAGCCTGTAA | 112 |
| flgF | GAAGGCAGTAACGTCAATGCCGTTGCGGCAATGAGCGACATGATTGCCAGCGCGCGGCGTTTTGAAATGCAGATGAAGGTGATCAGCAGCGTCGATGATA | 113 |
| htrL | CCCGATCTCTTCAACCTAAACTATCTGGGGAGAGGAAAATGGTTCGATTTGTTTCGCTGCTTCAGGAGTAACACTTTAGGGGCAAAAATGCAGGCGCTGA | 114 |
| recA | AACACGCTGCTGATCTTCATCAACCAGATCCGTATGAAAATTGGTGTGATGTTCGGTAACCCGGAAACCACTACCGGTGGTAACGCGCTGAAATTCTACG | 115 |
| uvrA | GCTGCCTGCTATCTCCGACATGAGCATTGGTCATGCGATGGAATTCTTCAACAATCTCAAACTCGCAGGTCAGCGGGCGAAGATTGCAGAAAAAATCCTT | 116 |
| wbbK | TTTCCCTCTAGGTTAGAAACATGGGGATTGCCGTTGTCTGAAGCTAAAGAGCGAGGTAAGTGGGTATTAGCATCAGATTTCCCATTTACTAGAGAAACTC | 117 |
| ybhK | AACGGAACCGAGCGTCGCCTCCGCGATGTTTGAATACCGTTTTGGTGGCAATGGCGAACTTTCCGGTCATAATCTCGGAAACTTGATGTTAAAGGCGCTG | 118 |
| uup | AACGCTATCACGATATTTCGCGCCTGGTGATGAACGACCCGAGCGAGAAAAATCTCAACGAACTGGCGAAGGTTCAGGAACAGCTGGATCACCACAACCT | 119 |
| fabD | TGCCATCCGTGACGCACTGGTACGTCAGTTGTATAACCCGGTTCAGTGGACGAAGTCTGTTGAGTACATGGCAGCGCAAGGCGTAGAACATCTCTATGAA | 120 |
| fabD | TGCCATCCGTGACGCACTGGTACGTCAGTTGTATAACCCGGTTCAGTGGACGAAGTCTGTTGAGTACATGGCAGCGCAAGGCGTAGAACATCTCTATGAA | 121 |
| proC | AAACCTGGCATCATGATTAAAGTGCTTAGCGAAATCACCTCCAGCCTGAATAAAGACTCTCTGGTCGTTTCTATTGCTGCAGGTGTCACGCTCGACCAGC | 122 |
| rpoB | ACTAACGAATACGGCTTCCTTGAGACTCCGTATCGTAAAGTGACCGACGGTGTTGTAACTGACGAAATTCACTACCTGTCTGCTATCGAAGAAGGCAACT | 123 |
| PA 0825 | TGTGGTTCTTCCTGGGCGGTTTCGGCGCACACCGCTTCTACCTGGGGAAAACCGGCACGGCGGTTACCCAACTGATCATCACGCTGATCGGTTGTTTCAC | 124 |
| PA 0985 | CCACAAACAATACTCTTATCAAGAATTCCCCAACCCCTCTAGAAAAGCAGAAAGCCATCTACAATGGTGAGCTACTTGTGGATGAGATAGCCAGTCTACA | 125 |
| cobB | GAACACGGCGGAGGCGGTGTTCCGTCTTGGCCGGCTGACGGCTTCCTATATCCATTTCTACCTGCCTTCCAACCCGCAGGCCGCCGCTGCGTTGCTGGCG | 126 |
| dxr | CCCGGCCATGCTGAATGCCGCGAACGAGGTGGCCGTGGCCGCATTTCTCGAGCGGCACATCCGCTTCAGCGACATCGCGGTTATCATCGAGGACGTGCTG | 127 |

-continued

| Gene | Sequence | SEQ ID NO: |
|---|---|---|
| flgF | TCTCGACCAGCGGCTTTCGTCGCGACTTCGAGCAGGCGCGTTCGATGCAGGTGTTCGGCGACAGCTTCCCGGCGCGGGTATTCGCCATGAGCGAGCGGCC | 128 |
| lexA | GCAGCAAGGTCTGGCTGCTGGCGGAAAACCCTGAGTTCGCTCCGATCGAAGTCGATCTGAAGGAGCAGGAACTGATCATCGAAGGCTTGAGCGTCGGCGT | 129 |
| moaE | CGGGGCAGGAGCTTAACGCCCTGCATGCGCAGAACGTCGGCATCGGCGCGGTGGTCGGCTTCGTCGGCTACGTGCGCGACTTCAACGACGGTCGCGAGGT | 130 |
| recA | GGTGAAGAACAAGGTTTCCCCGCCGTTCCGCCAGGCCGAGTTCCAGATCCTCTACGGTAAGGGCATCTACCGTACCGGCGAGATCATCGATCTGGGCGTG | 131 |
| PA 0284 | CTTCGGCGCCGTCGAGATCACCGTGCACAACGGCCAGGTGGTGCAGATCGAGCGCAAGGAAAAATTCCGTCTGCAGCAACCGGCCGTCAAGCAGGCCTGA | 132 |
| PA 0613 | GAGCACTATCTCAATCGCGACAGCTTCCCCGAGCAGAAGTACCGCCACTGCGGTTGCAGCCGCAACACCTTTTATCTGCGCCTGCATGTGGCGCACCAGG | 133 |
| PA 2012 | CCTGCTGAAGCGCGCCACGTGGAGATCCAGGTATTCGCCGACCGCCATGGCCACTGCCTGTACCTCAACGAACGCGACTGTTCGATCCAGCGCCGCCAC | 134 |
| PA 3126 | TTCAACGATCTGTTCGAGTCGGCCCTGCGTAATGAGGCCGGGAGTACCTACCCGCCCTACAACGTCGAAAAGCACGGTGACGACGAGTATCGCATCGTTA | 135 |
| PA 3932 | ACGGCCGCCTGAGCCTGCCGCCATTGCGCGAACGTCCGGGAGACATCCTGCCGCTGGCGGAATACTTCATCGGCGTCTATGCCCAGCGCCTGGACCTGCC | 136 |
| PA 4175 | ACGCTGCAGACCATCTGGTTCTACAACACCACCCAGTGCTACGGCGACGCCTCGACCATCAACCAGAGCGTCACCGTGCTGACCGGCGGGGCGAATATCC | 137 |
| PA 4762 | CCTGGAGATGTCCGATCCCAACGACGAGGCGATCAAGCCGATGCGCGAAGGGATGGAACTGACCCTGAAGATGTTCGACGACACCCTGCGCCGCTACCAG | 138 |
| hs1U | TATGTCGGACGCGACGTCGAATCGATCATCCGCGATCTCGCCGACGCCGCGGTGAAGATGCTCCGCGAACAGGAGATCCAGAAGGTCAAGTATCGCGCCG | 139 |
| fabD | GGTGGCGTTGCCAGTCAGCGTGCCGTCGCATTGCGAACTGATGCGTCCGGCCGCCGAGCAGTTCGCCGCCTCGGTCGAAAGCCTGCAGTGGCAGGCGCCG | 140 |
| proC | CCTGTGGCTGGACGACGAAGCGCAGATCGACGCGGTGACCGCAGTGTCGGGCAGCGGCCCCGGCGTATTTCTTCCTGCTGATGCAGGCCATGACCGACGCC | 141 |
| rpoB | ACCTTCGCCGTACCGCTGCGCGTGAAAGTTCGCCTGATCATCTTCGACCGCGAGTCGTCGAACAAGGCGATCAAGGACATCAAGGAACAAGAAGTCTACA | 142 |
| mecA | AACATGATGATGGCTATTAATGTTAAAGATGTACAAGATAAAGGAATGGCTAGCTACAATGCCAAAATCTCAGGTAAAGTGTATGATGAGCTATATGAGA | 143 |
| mecA | AGAATATAAAGGCTATAAAGATGATGCAGTTATTGGTAAAAAGGGACTCGAAAAACTTTACGATAAAAAGCTCCAACATGAAGATGGCTATCGTGTCACA | 144 |
| EF vanA | TGATAGGCCGGTGGCAGCTACGTTTACCTATCCTGTTTTTGTTAAGCCGGCGCGTTCAGGCTCATCCTTCGGTGTGAAAAAAGTCAATAGCGCGGACGAA | 145 |
| EF vanA | GGAGCGAGGACGGATACAGGAAACGGCAAAAAAAATATATAAAGCGCTCGGCTGTAGAGGTCTAGCCCGTGTGGATATGTTTTTACAAGATAACGGCCGC | 146 |
| EF vanB | GAGGACGCTTACCTACCCTGTCTTTGTGAAGCCGGCACGGTCAGGTTCGTCCTTTGGCGTAACCAAAGTAAACAGTACGGAAGAACTAAACGCTGCGATA | 147 |
| EF vanB | AATCCGGTTGAGCCACGGTATCTTCCGCATCCATCAGGAAAACGAGCCGGAAAAAGGCTCAGAGAATGCGATGATTATCGTTCCAGCAGACATTCCGGTC | 227 |
| Rv0813c.1 | ACCAGGCTTACGAGAAGCGGGATTCTGGCGGTTCGTCGCCGACCCGTACGATCCGAGCGAGTCTCAGGCGATCGAGTTGCTATTGGCGCATTCGGCCGGT | 148 |
| Rv1608c.1 | CCGCCCAATTCGGGGTCAAGCGCGGTCTGTTGGGCAAGTTGATGCCGGTCAAACGCACGACCTTTGTCATCGACACCGACCGTAAGGTGCTCGACGTGAT | 149 |
| Rv1832.1 | GTCGATTACCTGGCCTGAATTCGGGCGTCAGCATCCATTTGCCCCGGCATCTGATACCGCTGGGCTGCGTCAACTTGTTGCCGACCTACAGAGTTGGCTG | 150 |
| Rv3417c.1 | CGTTGATCCTGCTGCACCAAGACAAGATCAGCTCGCTTCCCGATCTGTTGCCATTGCTGGAAAAGGTTGCAGGAACGGGTAAGCCACTACTGATCGTGGC | 151 |

-continued

| Gene | Sequence | SEQ ID NO: |
|---|---|---|
| Rv1570.1 | CAGCTGGCCGGCTTGGCGCGATATCCGCAGCCGATGGCCCCGGCCGCCGCCGCCGAACACGCCGGGATGGCGTTGCCCGCCCGCGATCAGATCGTGCGG | 152 |
| Rv1606.1 | GGTGCGCCTGGATTGTGACGGCGACGCCGTATTGTTGACGGTTGACCAGGTCGGCGGTGCCTGCCATACCGGCGATCACAGTTGCTTCGATGCCGCGGTG | 153 |
| Rv2296.1 | CCGCGCAGGGGCGCACCCCACTCCCCTTCTACGTGTGGCGGGCGTTTGCGCGCTATTCTCCGGTGCTTCCCGCTGGCCGTCTGGTGAACTTCGGCACCGT | 154 |
| Rv2364c.1 | GGTGGATTGTCGAGCAGCTTCGTTCGACCGGCCCTGCCAATACGACACTGGTGGTCATCGTCACCAAGATTGACAAGGTGCCGAAAGAAAAAGTGGTCGC | 155 |
| Rv2245.1 | CGGCATCCACGCACTCGAAGACGAGTTCGTCACCAAGTGGGATCTAGCGGTCAAGATCGGCGGTCACCTCAAGGATCCGGTCGACAGCCACATGGGCCGA | 156 |
| Rv2247.1 | CGGCGAGTGCACCGTTCCGCGGGTCACGCTGGTCACCCGAAAGACCTACGGCGGGGCATACATTGCGATGAACTCCCGGTCGTTGAACGCGACCAAGGTG | 157 |
| Rv2846c.1 | GTGTGTCCTCGCAGCTGGTGTCCCGGTTTTCGCCACGGGTGTTGACCATCGGCGGCGGATATCTGCTATTCGGCGCCATGCTGTACGGCTCATTTTTCAT | 158 |
| Rv3675.1 | GCAGGCCGAGGCCGTGGATGTGCATACGCTCGCTCGGAATGGAATGCCGGAGGCGCTGGATTACCTGCATCGACGTCAAGCCCGGCGAATCACCGATTCA | 159 |
| Rv3801c.1 | GAGAGAGTGGGATGGCGTACCACAACCCCGTTCATCGTGAATGGAAAGATCAGGTTCCCAGCCAACACCAACCTGGTTCGTCACGTCGAAAAGTGGGCGAA | 160 |
| Rv2245.1 | CGGCATCCACGCACTCGAAGACGAGTTCGTCACCAAGTGGGATCTAGCGGTCAAGATCGGCGGTCACCTCAAGGATCCGGTCGACAGCCACATGGGCCGA | 161 |
| Rv2247.1 | CGGCGAGTGCACCGTTCCGCGGGTCACGCTGGTCACCCGAAAGACCTACGGCGGGGCATACATTGCGATGAACTCCCGGTCGTTGAACGCGACCAAGGTG | 162 |
| Rv0055.1 | CAAGTCCAGCAAGCGGCGCCCGGCTCCGGAAAAGCCGGTCAAGACGCGTAAATGCGTGTTCTGCGCGAAGAAGGACCAAGCGATCGACTACAAGGACACC | 163 |
| Rv1317c.1 | CGGCCGCCCGATTCGAGTCTGCCACCGCATCAGCGGGCACGGTGTCGCTGCGGCTACCCGTCCGTGCACCATTCGCCTTCGAGGGTGTTTTCGGCCATCT | 164 |
| Rv2737c.1 | TCGTCAACGGTCGACGGATCCAGAGCAAACGTCAAGTGTTCGAGGTCCGGATCTCGGGTATGGATAACGTCACGGCATTCGCGGAGTCAGTTCCCATGTG | 165 |
| Rv2790c.1 | AACAACCCGTATGCACAGTTTCAGGACGAATACACCCTGGACGACATCTTGGCCTCAAAGATGATTTCCGACCCGCTGACCAAATTGCAGTGCTCTCCCA | 166 |
| Rv3296.1 | CCGCTACCGCAGTGGTACCCACCGACAGCACATTGTTGGTCGAGCGGTTTCGTGACGAGCTGGGCGATTGGCGGTGATCTTGCATTCGCCGTATGGGCT | 167 |
| rv2032 | TCGCTGCGGCTCTACGATTCGTCGTATCATGCCGAACTCTTTTGGTGGACAGGGGCTTTTGAGACTTCTGAGGGCATACCGCACAGTTCATTGGTATCGG | 168 |
| rv2827c | CGGCACACCGAAGTGATGCCGGTGACTCGATTCACCACCGCGCACAGCCGCGACCGTGGCGAGAGTGTCTGGGCTCCCGAGTATCAGCTTGTCGACGAGC | 169 |
| rv3880c | CGGTTTCAGTCGGCCCTAGACGGGACGCTCAATCAGATGAACAACGGATCCTTCCGCGCCACCGACGAAGCCGAGACCGTCGAAGTGACGATCAATGGGC | 170 |
| Rv0667.1 | AAGAGGTGCTCTACGAGCTGTCTCCGATCGAGGACTTCTCCGGGTCGATGTCGTTGTCGTTCTCTGACCCTCGTTTCGACGATGTCAAGGCACCCGTCGA | 171 |
| Rv1980c.1 | CGCCGAATGCCGGCTTGGACCCGGTGAATTATCAGAACTTCGCAGTCACGAACGACGGGGTGATTTTCTTCTTCAACCCCGGGGGAGTTGCTGCCCGAAGC | 172 |
| Rv2703.1 | AGCGACCAAAGCAAGCACGGCGACCGATGAGCCGGTAAAACGCACCGCCACCAAGTCGCCCGCGGCTTCCGCGTCCGGGGCCAAGACCGGCGCCAAGCGA | 173 |
| tig | AAGCACTCTACGAAAATGCATTGAATTTAGTGTTGCCAAAGGCTTACGAA | 174 |
| pyrG | AAATTGTTTGTGATCACTTGAAGCTTGAGACACCTGCTGCTGATATGACA | 175 |
| scrR | AACTATCTTATGTAATAGTGAAAAGGATCCTATCAAAGAAAAAGAATACC | 176 |
| hslO | AAATAGTAAAGTAACTGTCAAGGTTATTGGAGATAGCTCTTTTGGTCATA | 177 |
| SglyS | AAGGGAATTTTTCTAAAGCAGCCCAAGGTTTTGTTCGCGGAAAAGGTTTA | 178 |

-continued

| Gene | Sequence | SEQ ID NO: |
|---|---|---|
| proB | AAGCGTCCTCAAGAAATATCACAACAACAAGCAGTTTCTAGCGTAGGACA | 179 |
| mraW | AAGGCTATTGACAATGCTCATATACGTTTAAAGAAATATGTGGATACCGG | 180 |
| ftsL | AAGTTAAACAAGAAGTAAATCAATTAAATAGTAAAATCAACGATAAACAG | 181 |
| dkgB | AACCAAATCGAGCTGTCGCCATATCTGCAGAACCGCAAAGTGGTGGAATT | 182 |
| mtnK | AACCCTGTTGATTCACGGCGGTTTTTGCCCAAGGCATACGGTAAAGGTAC | 183 |
| xylF | AACCGCTGATTGACGGCGGGAAAATCAAAGTGGTGGGCGATCAGTGGGTC | 184 |
| proA | AAACTGGAAGCCGAAAGCGAAGTGATTTTACAGGCTAACGAACAGGACAT | 185 |
| aroL | AAAGCATTGCTCTGCAAACGGTCACTCAACCGTCAACTGTAGTTGCCACT | 186 |
| PstS | AAAAATGGAACGACCCGGCGATCACCAAGCTCAACCCAGGCGTTAAGCTG | 187 |
| secD | AACGTGACATGGTGTTCTCTGCCAACGGCACCAACACCCTGAAAGCCAAC | 188 |
| ribD | AACCTGCGTCAACCGTTGCGCATTATTCTGGATAGCCAAAATCGCGTCAC | 189 |
| dnaA | AATTGTTCTGACTAGTGATCGTAGTCCTAAACACTTAGAGGGCCTTGAAG | 190 |
| mscL | AAGGAATTGAAAAAGCTCAAAGCCTTACTAAGAAAGAAGAAGCTGCTGAG | 191 |
| purR | ACTGGTGCTGGTGGTGGTGTCATTTTCACACCATCAATCTCAAGCCATGA | 192 |
| amiA | AAGATGGTTTATTCAATTTTCTGGCCATTAAACGAAGAATTTGAAAAATC | 193 |
| nanA | AGCGATGACCTATACCACCTATGATAGTGGTAATAGTGGTCAACAAACAG | 194 |
| codY | AACATGATTTACGATACAGAAGCCAATCTGACAGTTGATCATGATTTGAG | 195 |
| pstS | ACAACTCCGTAGTATCTTCACAGGTCAAGTGACCAACTGGAAAGAAGTCG | 196 |
| CaJ7_0076 | AAAGCTGCTAAATCTGCCAAGACTGCTGCTGCTGGTGGTAAGAAGGAAGC | 197 |
| CaJ7_0103 | AAAATGCTACTACATCTCCATCATACTTTACTACTATTCATCCCGAAACA | 198 |
| CaJ7_0197 | ACATAGTCCAATAACAAATAAACTTGAGGATCATGATGATGAAATTGGAT | 199 |
| CaJ7_0245 | AAAACAAACAATCAACTGGTGATGAAGTCAAGAGCAAGAGAAAATCGGCA | 200 |
| CaJ7_0344 | AATGATTTATGATACGTTTAATAAATTACAAGAATCTAGTGATCAGTCGA | 201 |
| CaJ7_0399 | ACACAAAACTGAAGACAAAGGGACTAGCACTTCATCCAAGGAAGAACCAT | 202 |
| fusA | ACTGGTGTAGTTGACCTTATCGAAATGAAGGCAATTATCTGGGATGAAGC | 203 |
| lysS | AATTGTGAATGAAGAAACGCGTAAGACTTTTGAAATTCGTGCCAAAGTCG | 204 |
| isocitrate lyase | AAAAAGTATTTCGGTACGACAAGCAAACGTTATATCTACCTTTCTGGTTG | 205 |
| ureC | ACACAACTAATTGCACCTGAAGCACAAATTTTAACACCTCGTGCTATTGA | 206 |
| rnhB | AAATTGATGAGCTGAATATCTTGCAGGCAACTTTTTTGGCTATGCAACGT | 207 |
| pyrB | AAAACTCCACCCGTACTCGTACTACTTTTGAAGCAGCAGCAAAACGTTTG | 208 |
| guaA | ACCGCAAGTGGTGTTTGAATTAGGCGTTCCAGTATTGGGTATTTGCTATG | 209 |
| cmk | AGTTGCAGGGTATGGGCTAGATGCTAAAATAAACGACATTTTAGCTAAT | 210 |
| secD | AAAATTGAAGCGAAATCAATCGCCCTTGAAAATGGTGCGATTTTGGCTCG | 211 |
| map1 | AAAAAGTAAAGATATTATTAATGTCGATATTACACTAGAAAAAAATGGTT | 212 |
| ftnA | AAAACTTATGAGCACGAGAAGTTTATTACAGCTGAAATTAATAAACTAGC | 213 |
| Prc | AAAACAGGTGAATTACCTCCTTTATATGATCTGTTTAACCTTGCGCAAAA | 214 |
| nrdR | AAAACGCCCTGTGAGTTCTGATGATGTTGAAGCTGCTATTAATCATATCA | 215 |
| ackA | AAAGGTATTGAGGCGGCTATTCCATTTGCCCCATTACATAACCCAGCTCA | 216 |

| Gene | Sequence | SEQ ID NO: |
|---|---|---|
| Pta | AAAAAAGATGTTCTGATGGAAGAAATTGTTGCTAGATATCACGAAAATAC | 217 |
| fadL | AAATGGGCAATTGGTGCATCAGGTACTACTAACTTTGGTTTAGCTACCGA | 218 |
| purF | ATCGTCGGCAACCAGAACGTCGCCGGGCAGTTGTATGACGGCTTGACCGT | 219 |
| clpP | ATCGACATCCACGCGCGTGAGATCCTGACCCTGCGTTCGCGCCTGAACGA | 220 |
| sdhA | CAAGATCTACCAGCGTCCGTTCGGTGGCATGACCACCAAGTACGGCGAAG | 221 |
| dnaK | AAGCGCCTGATCGGCCGCAAGTTCACCGACGCCGAAGTGCAGAAGGACAT | 222 |
| secD | ATGCTCGAATTTCCACGCTGGAAGTACGTCGTCATCCTGATCGTACTGGC | 223 |
| cmk | CGAGCGCCGGCATAAGCAGTTGAAAGACAAGGGGGTTTCTGTTAACTTTG | 224 |
| purC | CCTGCCCGACCCGATCCCGGGCAAGGGCGAGATGCTCTGCCAGGTCTCCA | 225 |
| pantothenate kinase | CGCCGAAGGCATGGCCGGACAGCCGCCGCACAGCCTGCCCAGCGGCACCA | 226 |

TABLE 3

24-gene probeset for pilot experiments

| Name | Gene# | Purpose | Magnitude of induction/repression in prior microarray-based assays[1] | | | |
|---|---|---|---|---|---|---|
| | | | ETH/INH | SM | RIF | FQ |
| Rv0667 | rpoB | control | −0.8 | 1.4 | 0.1 | 0.5 |
| Rv1980c | mpt64 | control | 0.2 | 0.4 | −1.2 | 0.1 |
| Rv2703 | sigA | control | 0.0 | 0.4 | −1.4 | −0.8 |
| Rv3583c | Rv3583c | control | 0.6 | 1.0 | −1.8 | 1.6 |
| Rv0055 | rpsR | FQ | 1.4 | 1.7 | −0.9 | 3.6 |
| Rv1317c | alkA | FQ | 1.0 | 0.4 | 0.5 | 5.5 |
| Rv2737c | recA | FQ | −0.2 | −0.1 | −0.6 | 4.6 |
| Rv2790c | ltp1 | FQ | −0.9 | −1.1 | −0.7 | 4.2 |
| Rv3296 | lhr | FQ | 0.3 | 0.1 | 0.2 | 4.1 |
| Rv2245 | kasA | INH | 7.4 | −1.9 | −1.0 | −1.1 |
| Rv2247 | accD6 | INH | 5.1 | −0.8 | −0.8 | −1.3 |
| Rv2846c | efpA | INH | 6.2 | −0.7 | −0.9 | 0.2 |
| RV3675 | Rv3675 | INH | 2.4 | 0.0 | 0.0 | −0.4 |
| Rv3801c | fadD32 | INH | 3.3 | 0.8 | −0.6 | −0.2 |
| Rv0984 | moaB2 | RIF | −0.9 | −1.1 | 1.7 | 0.1 |
| RV1570 | bioD | RIF | 0.2 | −0.3 | 1.2 | 0.2 |
| RV1606 | hisI | RIF | −0.1 | −0.4 | 1.5 | −0.1 |
| Rv2296 | haloalkane | RIF | −0.7 | 0.1 | 1.2 | −0.1 |
| Rv2364c | era | RIF | −1.0 | −0.6 | 1.4 | 0.0 |
| Rv0813c | CHP | SM | 0.3 | 3.8 | 0.3 | 0.1 |
| Rv1511 | gmdA | SM | 0.4 | 1.6 | −0.3 | 0.5 |
| Rv1608c | bcpB | SM | 0.9 | 2.2 | 0.3 | 0.2 |
| Rv1832 | gcvB | SM | −0.4 | 1.3 | −0.4 | −0.4 |
| Rv3417c | groEL | SM | −0.3 | 1.6 | −0.9 | −0.8 |

[1]The transcriptional responses of Mycobacterium tuberculosis to inhibitors of metabolism: novel insights into drug mechanisms of action. Boshoff H I, Myers T G, Copp B R, McNeil M R, Wilson M A, Barry C E 3rd. J BiolChem. 2004 Sep. 17; 279(38): 40174-84

| Gene | Acc. No. | Sequence |
|---|---|---|
| lhr | Rv3296.1 | CCGCTACCGCAGTGGTACCCACCGACAGCACATTGTTGGTCGAGCGGTTTCGTGACGAGCTGGGCGATTGGCGGGTGATCTTGCATTCGCCGTATGGGCT |
| alkA | Rv1317c.1 | CGGCCGCCCGATTCGAGTCTGCCACCGCATCAGCGGGCACGGTGTCGCTGCGGCTACCCGTCCGTGCACCATTCGCCTTCGAGGGTGTTTTCGGCCATCT |
| ltp1 | Rv2790c.1 | AACAACCCGTATGCACAGTTTCAGGACGAATACACCCTGGACGACATCTTGGCCTCAAAGATGATTTCCGACCCGCTGACCAAATTGCAGTGCTCTCCCA |
| recombinase_ (contains_ intein) | Rv2737c.1 | TCGTCAACGGTCGACGGATCCAGAGCAAACGTCAAGTGTTCGAGGTCCGGATCTCGGGTATGGATAACGTCACGGCATTCGCGGAGTCAGTTCCCATGTG |
| bioD | Rv1570.1 | CAGCTGGCCGGCTTGGCGCGATATCCGCAGCCGATGGCCCCGGCCGCCGCCGCCGAACACGCCGGGATGGCGTTGCCCGCCCGCGATCAGATCGTCGGGC |
| bex | Rv2364c.1 | GGTGGATTGTCGAGCAGCTTCGTTCGACCGGCCCTGCCAATACGACACTGGTGGTCATCGTCACCAAGATTGACAAGGTGCCGAAAGAAAAAGTGGTCGC |

-continued

| Gene | Acc. No. | Sequence |
|---|---|---|
| hisI2 | Rv1606.1 | GGTGCGCCTGGATTGTGACGGCGACGCCGTATTGTTGACGGTTGACCA GGTCGGCGGTGCCTGCCATACCGGCGATCACAGTTGCTTCGATGCCGC GGTG |
| moaB2 | Rv0984.1 | CCGCGCAGTGTTCAAAGCTCGGATATACGGTGGCACCCATGGAACAGC GTGCGGAGTTGGTGGTTGGCCGGGCACTTGTCGTCGTCGTTGACGATC GCAC |
| epfA | Rv2846c.1 | GTGTGTCCTCGCAGCTGGTGTCCCGGTTTTCGCCACGGGTGTTGACCA TCGGCGGCGGATATCTGCTATTCGGCGCCATGCTGTACGGCTCATTTT TCAT |
| acetyl/ propionyl_CoA_ carboxylase_ b_subunit | Rv2247.1 | CGGCGAGTGCACCGTTCCGCGGGTCACGCTGGTCACCCGAAAGACCTA CGGCGGGGCATACATTGCGATGAACTCCCGGTCGTTGAACGCGACCAA GGTG |
| Rv3675 | Rv3675.1 | GCAGGCCGAGGCCGTGGATGTGCATACGCTCGCTCGGAATGGAATGCC GGAGGCGCTGGATTACCTGCATCGACGTCAAGCCCGGCGAATACACCGA TTCA |
| gcvB | Rv1832.1 | GTCGATTACCTGGCCTGAATTCGGGCGTCAGCATCCATTTGCCCCGGC ATCTGATACCGCTGGGCTGCGTCAACTTGTTGCCGACCTACAGAGTTG GCTG |
| bcpB | Rv1608c.1 | CCGCCCAATTCGGGGTCAAGCGCGGTCTGTTGGGCAAGTTGATGCCGG TCAAACGCACGACCTTTGTCATCGACACCGACCGTAAGGTGCTCGACG TGAT |
| GDP- mannose_4, 6_ dehydratase | Rv1511.1 | ACGCCGTTCTACCCGCGGTCACCGTATGGCGCCGCCAAGGTCTATTCG TACTGGGCGACCCGCAATTATCGCGAAGCGTACGGATTGTTCGCCGTT AACG |
| 60 kD chaperonin_1 | Rv3417c.1 | CGTTGATCCTGCTGCACCAAGACAAGATCAGCTCGCTTCCCGATCTGT TGCCATTGCTGGAAAAGGTTGCAGGAACGGGTAAGCCACTACTGATCG TGGC |
| mpt64 | Rv1980c.1 | CGCCGAATGCCGGCTTGGACCCGGTGAATTATCAGAACTTCGCAGTCA CGAACGACGGGGTGATTTTCTTCTTCAACCCGGGGGAGTTGCTGCCCG AAGC |
| rpoB | Rv0667.1 | AAGAGGTGCTCTACGAGCTGTCTCCGATCGAGGACTTCTCCGGGTCGA TGTCGTTGTCGTTCTCTGACCCTCGTTTCGACGATGTCAAGGCACCCG TCGA |
| Rv3583c | Rv3583c.1 | GAACAAAAAGAGTATCTCGTCTTGAAAGTTGCGCAGGGCGACCTGACA GTACGAGTTCCCGCTGAAAACGCCGAATACGTCGGTGTTCGCGATGTC GTCG |
| sigA | Rv2703.1 | AGCGACCAAAGCAAGCACGGCGACCGATGAGCCGGTAAAACGCACCGC CACCAAGTCGCCCGCGGCTTCCGCGTCCGGGGCCAAGACCGGCGCCAA GCGA |
| b- ketoacyl- ACP_ synthase_ (meromycolate_ extension) | Rv2245.1 | CGGCATCCACGCACTCGAAGACGAGTTCGTCACCAAGTGGGATCTAGC GGTCAAGATCGGCGGTCACCTCAAGGATCCGGTCGACAGCCACATGGG CCGA |
| 30S_ribosomal_ protein_ S18 | Rv0055.1 | CAAGTCCAGCAAGCGGCGCCCGGCTCCGGAAAAGCCGGTCAAGACGCG TAAATGCGTGTTCTGCGCGAAGAAGGACCAAGCGATCGACTACAAGGA CACC |
| haloalkane dehalo- genase | Rv2296.1 | CCGCGCAGGGGCGCACCCCACTCCCCTTCTACGTGTGGCGGGCGTTTG CGCGCTATTCTCCGGTGCTTCCCGCTGGCCGTCTGGTGAACTTCGGCA CCGT |
| fadD22 | Rv3801c.1 | GAGAGAGTGGGATGGCGTACCACAACCCGTTCATCGTGAATGGAAAGA TCAGGTTCCCAGCCAACACCAACCTGGTTCGTCACGTCGAAAGTGGG CGAA |
| CHP | Rv0813c.1 | ACCAGGCTTACGAGAAGCGGGATTCTGGCGGTTCGTCGCCGACCCGTA CGATCCGAGCGAGTCTCAGGCGATCGAGTTGCTATTGGCGCATTCGGC CGGT |

What is claimed is:

1. A method comprising:

contacting an uncultured clinical urine or blood sample from a mammalian subject, wherein the sample is known or suspected to comprise pathogenic bacteria comprising *Escherichia coli*, with one or more test compounds selected from the group consisting of a fluoroquinolone antibiotic, aminoglycoside antibiotic, and ampicillin, to provide a test sample;

treating the test sample under conditions that release messenger ribonucleic acid (mRNA) from any pathogenic bacteria present in the clinical urine sample into the test sample;

exposing the test sample to a plurality of nucleic acid probes, comprising a plurality of subsets of probes, wherein each subset comprises one or more probes that bind specifically to a target mRNA that is differentially expressed in organisms that are sensitive to an antibiotic test compound as compared to organisms that are resistant, wherein the target mRNA is one or more of recA, carA, deoC, figF, htrL, uvrA, ybhK, uup, fabD, cysD, glnA, opgG, ftsQ, b1649, dinD, pyrB, wbbK, or hdeA mRNA, wherein the exposure occurs for a time and under conditions in which binding between the probes and the target mRNA can occur, and wherein the mRNA is crude and unpurified when contacted with the probes and the method does not include amplifying the mRNA; and determining a level of binding between the probes and target mRNA, thereby determining a level of the target mRNA.

2. The method of claim 1, wherein the method comprises contacting the uncultured clinical urine or blood sample with two or more antibiotic test compounds.

3. The method of claim 1, wherein the uncultured clinical urine or blood sample is contacted with the one or more antibiotic test compounds for less than four hours.

4. The method of claim 1, wherein the uncultured clinical urine or blood sample comprises a plurality of different pathogenic bacteria.

5. The method of claim 1, wherein the plurality of nucleic acid probes comprises probes that bind specifically to recA mRNA and probes that bind specifically to uvrA mRNA.

6. The method of claim 1, comprising partitioning the uncultured clinical urine sample, and contacting the individual partitions with different antibiotic test compounds.

7. The method of claim 1, wherein the test compound is a fluoroquinolone or aminoglycoside antibiotic.

8. A method comprising:

contacting an uncultured clinical blood or urine sample, wherein the sample is known or suspected to comprise pathogenic bacteria comprising *Staphylococcus aureus*, from a mammalian subject with methicillin to provide a test sample;

treating the test sample under conditions that release messenger ribonucleic acid (mRNA) from any pathogenic bacteria present in the clinical blood sample into the test sample;

exposing the test sample to a plurality of nucleic acid probes, comprising a plurality of subsets of probes, wherein each subset comprises one or more probes that bind specifically to a target mRNA that is differentially expressed in organisms that are sensitive to methicillin as compared to organisms that are resistant, wherein the target mRNA is mecA, wherein the exposure occurs for a time and under conditions in which binding between the probes and the target mRNA can occur, and wherein the mRNA is crude and unpurified when contacted with the probes and the method does not include amplifying the mRNA; and determining a level of binding between the probes and target mRNA, thereby determining a level of the target mRNA.

9. The method of claim 8, wherein the uncultured clinical blood sample is contacted with the methicillin for less than four hours.

10. The method of claim 8, wherein the uncultured clinical blood or urine sample comprises a plurality of different pathogenic bacteria.

11. A method comprising:
contacting an uncultured clinical sputum, urine, or blood sample from a mammalian subject, wherein the sample is known or suspected to comprise pathogenic bacteria comprising *Mycobacterium tuberculosis*, with one or more antibiotic test compounds selected from the group consisting of isoniaid, rifampin, streptomycin, and a fluoroquinolone antibiotic, to provide a test sample;
treating the test sample under conditions that release messenger ribonucleic acid (mRNA) from any pathogenic bacteria present in the clinical urine sample into the test sample;
exposing the test sample to a plurality of nucleic acid probes, comprising a plurality of subsets of probes, wherein each subset comprises one or more probes that bind specifically to a target mRNA that is differentially expressed in organisms that are sensitive to an antibiotic test compound as compared to organisms that are resistant, wherein the target mRNA is one or more kasA, fadD32, accD6, efpA, Rv3675.1, bioD, hisl, era, Rv2296, Rv0813, rpsR, alkA, recA, ltp1, lhr, CHP, bcpB, gcvB, or groEL mRNA, wherein the exposure occurs for a time and under conditions in which binding between the probes and the target mRNA can occur, and wherein the mRNA is crude and unpurified when contacted with the probes and the method does not include amplifying the mRNA; and
determining a level of binding between the probes and target mRNA, thereby determining a level of the target mRNA.

12. The method of claim 11, wherein:
the one or more antibiotic test compounds comprise isoniazid, and the target mRNA comprises kasA, fadD32, accD6, efpA, or Rv3675.1;
the one or more antibiotic test compounds comprise Rifampin, and the target mRNA comprises bioD, hisI, era, or Rv2296;
the one or more antibiotic test compounds comprise a fluoroquinolone antibiotic, and the target mRNA comprises rpsR, alkA, recA, ltp1, lhr, kasA, or accD6; or
the one or more antibiotic test compounds comprise streptomycin, and the target mRNA comprises Rv0813, accD6, KasA, CHP, bcpB, gcvB, or groEL.

13. The method of claim 11, wherein the method comprises contacting the uncultured clinical blood or urine sample with two or more antibiotic test compounds.

14. The method of claim 11, wherein the uncultured clinical blood or urine sample is contacted with the one or more antibiotic test compounds for less than four hours.

15. The method of claim 11, wherein the uncultured clinical blood sample further comprises a plurality of different pathogenic bacteria.

16. The method of claim 11, comprising partitioning the uncultured clinical blood or urine sample, and contacting the individual partitions with different antibiotic test compounds.

17. A method comprising:
contacting an uncultured clinical urine or blood sample from a mammalian subject with ciprofloxacin, wherein the sample is known or suspected to comprise pathogenic bacteria comprising *Pseudomonas aeruginosa*, to provide a test sample;
treating the test sample under conditions that release messenger ribonucleic acid (mRNA) from any pathogenic bacteria present in the clinical urine sample into the test sample;
exposing the test sample to a plurality of nucleic acid probes, comprising a plurality of subsets of probes, wherein each subset comprises one or more probes that bind specifically to a target mRNA that is differentially expressed in organisms that are sensitive to an antibiotic test compound as compared to organisms that are resistant, wherein the target mRNA is one or more of PA 4175, mpl, or proA mRNA, wherein the exposure occurs for a time and under conditions in which binding between the probes and the target mRNA can occur, and wherein the mRNA is crude and unpurified when contacted with the probes and the method does not include amplifying the mRNA; and
determining a level of binding between the probes and target mRNA, thereby determining a level of the target mRNA.

18. The method of claim 17, wherein the uncultured clinical blood or urine sample is contacted with the ciprofloxacin for less than four hours.

19. The method of claim 17, wherein the uncultured clinical blood sample further comprises a plurality of different pathogenic bacteria.

* * * * *

UNITED STATES PATENT AND TRADEMARK OFFICE
CERTIFICATE OF CORRECTION

PATENT NO. : 9,885,088 B2
APPLICATION NO. : 13/580618
DATED : February 6, 2018
INVENTOR(S) : Deborah Hung, James Gomez and Amy Barczak It is certified that error appears in the above-identified patent and that said Letters Patent is hereby corrected as shown below:

In the Claims

In Column 153, Line 48, in Claim 1, delete "figF," and insert -- flgF, --;

In Column 155, Line 7, in Claim 11, delete "isoniaid," and insert -- isoniazid, --;

In Column 155, Line 20, in Claim 11, delete "hisl," and insert -- hisI, --;

In Column 155, Line 43, in Claim 12, delete "KasA," and insert -- kasA, --;

In Column 156, Line 30, in Claim 17, delete "PA 4175," and insert -- PA_4175, --.

Signed and Sealed this
Ninth Day of October, 2018

Andrei Iancu
*Director of the United States Patent and Trademark Office*

UNITED STATES PATENT AND TRADEMARK OFFICE
CERTIFICATE OF CORRECTION

PATENT NO. : 9,885,088 B2
APPLICATION NO. : 13/580618
DATED : February 6, 2018
INVENTOR(S) : James Gomez, Deborah Hung and Amy Barczak It is certified that error appears in the above-identified patent and that said Letters Patent is hereby corrected as shown below:

In the Specification

Column 1, Line 14:
In Federally Sponsored Research or Development, please delete "Grant Number A1057159 and Grant Number A108002" and add "Grant Numbers AI057159 and AI108002".

Signed and Sealed this
First Day of October, 2024

Katherine Kelly Vidal
*Director of the United States Patent and Trademark Office*

SEQUENCE LISTING

<160> NUMBER OF SEQ ID NOS: 251

<210> SEQ ID NO 1
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 1
cgacagtgtt ggtgagcggc tgggtcgtgt tgggctggat ggaagatgcg caacgcctgc     60
cgctctcaaa gctggtgttg accggtgaac gccattacac                          100

<210> SEQ ID NO 2
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 2
gaattgttac cgcgagtggg gcgtcagacc acgacttacg gcttcagcga agatgccgac     60
gtgcgtgtag aagattatca gcagattggc ccgcaggggc                          100

<210> SEQ ID NO 3
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 3
ttgtggatgt gcagtcgaaa atctatctgc gcgataaagt cggcaaactg ggggttgcac     60
cgttaaccag tatgttcctg tttgggccga accaaccgtc                          100

<210> SEQ ID NO 4
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 4
tagtgtttag tttgctgggt aaagcgccgt cagcggcgat gcaaaaacgc tttgccgagg     60
ccgatgcgca ctatcattcg gctccgccgt cacggttgca                          100

<210> SEQ ID NO 5
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 5
ctcggaaatg tataaacgcg tgaataaaat tattccgcac ctgatccgtc aggaaaaaga     60
agactccgaa accttccagg gcgaaggcca cttctcggtg                          100

<210> SEQ ID NO 6
<211> LENGTH: 100
<212> TYPE: DNA
<213> ORGANISM: Artificial Sequence
<220> FEATURE:
<223> OTHER INFORMATION: synthetically generated oligonucleotide

```
<400> SEQUENCE: 6
aacgctatca cgatatttcg cgcctggtga tgaacgaccc gagcgagaaa aatctcaacg    60
aactggcgaa ggttcaggaa cagctggatc accacaacct                        100

<210> SEQ ID NO 7
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 7
gagctagtag aaaaaggtaa atcattaggt gcaaaacgtg tcatgccttt agcagtatct    60
ggaccattcc attcatcgct aatgaaagtg attgaagaag                        100

<210> SEQ ID NO 8
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 8
taacagctat caccggaagc ggcccagcat ttttatatca tgtattcgag caatatgtta    60
aagctggtac gaaacttggt ctagaaaaag aacaagttga                        100

<210> SEQ ID NO 9
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 9
ggagaaatgg cattaggtag aaacgtagta gttggtttca tgacttggga cggttacaac    60
tatgaggatg ccgttatcat gagtgaaaga cttgtgaaag                        100

<210> SEQ ID NO 10
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 10
aaagatcctg aaggcaataa atatatggat atgttatctg catattccgc              50

<210> SEQ ID NO 11
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 11
aatattaaaa atgactgaag acggtactga tgaaatcatt tctacacgtt              50

<210> SEQ ID NO 12
<211> LENGTH: 50
<212> TYPE: DNA
<213> ORGANISM: Artificial Sequence
<220> FEATURE:
```

<223> OTHER INFORMATION: synthetically generated oligonucleotide

<400> SEQUENCE: 12
acaggtcatt taggatttta tgcggattgg ttacctcatg aagttgaaaa          50

<210> SEQ ID NO 13
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 13
aaattagacc gagtaggtaa agaaccattt gaattattag atgaaatcga          50

<210> SEQ ID NO 14
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 14
aaatatttcg gaccgtatcc gaatgcatat tctgctcaag aaactaaaaa          50

<210> SEQ ID NO 15
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 15
aaattcaaga aaaatgggat gcagaagatc aataccataa agcgttagaa          50

<210> SEQ ID NO 16
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 16
aaatatacaa acttatccaa aaggcaagtc aatttaaatc tggtgaacgt          50

<210> SEQ ID NO 17
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 17
aaaccctatg atagatgaag ttattaacca aaaaccacgt gttgttatat          50

<210> SEQ ID NO 18
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 18
caactgatgc tcacggttca ctatgaaggt aaggcgattt gtggcgtgtt taccgcggaa          60
gtggcggaga ccaaagtcgc tatggtgaat cagtacgcga                              100

<210> SEQ ID NO 19
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 19
ctcgcaccgg acgtaacccg aaaactggtg ataaagtcga actggaaggt aagtacgttc    60
cgcactttaa gcccgggaaa gaattacgtg accgcgccaa                         100

<210> SEQ ID NO 20
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 20
tcatctggtt tccggtgatt tcgactatct gttgaaaacc cgtgtaccgg atatgtcagc    60
gtatcgtaaa ttactgggcg agaccttgct gcgcctgccg                         100

<210> SEQ ID NO 21
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 21
tcattcgctg gaagatcgca ttgtgaagcg ctttatgcgt gagcaaagcc gcggtccgca    60
ggttccggcg ggaataccga tgaccgaagc gcagctcaaa                         100

<210> SEQ ID NO 22
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 22
gcgatctacg cgcagaagga attcctctgg aacaacatca agcagccgaa ccgcaacctg    60
ctgctgtggc gcgacaagac cgtcgacggc ctgaagaccg                         100

<210> SEQ ID NO 23
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 23
cctgcggcta cgccgggatg cccatgaccc aactgcgcga cctggttggg ccggtggatt    60
ttgccgaggt gtgtacccga ttgcgcgctg agctcgtctc                         100

<210> SEQ ID NO 24
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 24
accgcccgcg cacggcgatc ctgaacaacc tggaattcga ccacgcggat atcttcccccg        60 acctcgcggc catcgagcgg cagttccacc atctggtgcg                              100

<210> SEQ ID NO 25
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 25
aagtggattc cgcttcggtg atggtcaacg cctcgacccg cttcgccgac ggcttcgagt        60
acggcctcgg cgccgagatc gggatttcca ccgacaagct                             100

<210> SEQ ID NO 26
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 26
cgatgcgttt cgtcggcgac aagggcatcg agtattgggt cggtttgccg aacttctacg        60
tgatcacccg ctataatcgc agcgccatgt atgccatggc                             100

<210> SEQ ID NO 27
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 27
agctggtgtg aagcgaatga ttccgttaaa tgtgagtggc cctttccata cggcgctgtt        60
acaaccagca tcaaaaaaat tggctcagga tttagcaaaa                             100

<210> SEQ ID NO 28
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 28
caagaagcac aaatggctct tggcaataaa gaagccaaag ttgttcatgc cattcctaat        60
acaccagtta gcgtgaatca aggcgtgatt ggcgtagcct                             100

<210> SEQ ID NO 29
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 29
cacagttatc acagttcatg gaccaaacaa acccattagg tgagttaacc cataaacgtc        60
gtctatcagc cttagggcct ggtggtttga ctcgtgaccg                             100

<210> SEQ ID NO 30
<211> LENGTH: 50

```
<212> TYPE: DNA
<213> ORGANISM: Artificial Sequence
<220> FEATURE:
<223> OTHER INFORMATION: synthetically generated oligonucleotide

<400> SEQUENCE: 30
agccaagaag ctgccaaagg acgcctcgat cggcaatttt tttcagctag          50

<210> SEQ ID NO 31
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 31
atggtcatgt ggaattgctt ttgcttaaaa atacacaagg agatcaatgg          50

<210> SEQ ID NO 32
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 32
atcaagaaaa aaatccgctt atgattggtg tattaaaagg atcagttcct          50

<210> SEQ ID NO 33
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 33
aactttagca atagaactag gtgcttggat gcctatgcaa tttaataacc          50

<210> SEQ ID NO 34
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 34
attgggctac aagcctaaca atctcgctag aagtttgcaa ggtaaatcaa          50

<210> SEQ ID NO 35
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 35
agaaatgttt gacggtattc agcgaccgct tgatcgtttt caaaaagcaa          50

<210> SEQ ID NO 36
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 36
```
accattgacc atattttaga agacccaagc aaattagaaa ctatctctgg        50

<210> SEQ ID NO 37
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 37
aaatttacgt ggggcaatgt ctctgaagtt tgtcgtgaat taggacgtat        50

<210> SEQ ID NO 38
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 38
acgacatggt cgccaagcac cggcaactgg ccgagatcat cgccagcgac        50

<210> SEQ ID NO 39
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 39
tcacttgaaa gatttgaaaa aacgcaatat tcaacaccac taccttgctg        50

<210> SEQ ID NO 40
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 40
cgcgtgtgga aaaagctttt tactttcca ttgctgtaac cactcttatt         50

<210> SEQ ID NO 41
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 41
tggcgtacat gtaggtcaag atgatattgg tgttgatgaa attagaaaat        50

<210> SEQ ID NO 42
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 42
gattggtgga acaacttcat cggtgcagac tatgattctg gcaacctgca        50

<210> SEQ ID NO 43
<211> LENGTH: 50
<212> TYPE: DNA
<213> ORGANISM: Artificial Sequence

```
<220> FEATURE:
<223> OTHER INFORMATION: synthetically generated oligonucleotide

<400> SEQUENCE: 43
agtttttgaa aaacaatatg gctcagagct tgatgataaa gaggttgatg            50

<210> SEQ ID NO 44
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 44 attttatgg gagcctctta ggccgttttg gtgaagcgac agttggtcta             50

<210> SEQ ID NO 45
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 45
atttgattgc aggagattat tccaaggttc ttgatatgca aggtgggtct            50

<210> SEQ ID NO 46
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 46
aaagaagcgg gcaatatggt ggatctcgac tccaacccga ccaagttgat            50

<210> SEQ ID NO 47
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 47
agcaagtgct tacagtattg atacatatgc ttcattctga acgtggaatg            50

<210> SEQ ID NO 48
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 48
cttaaatatg ttaggggctc gcgagccaaa acattatggc agtatttctc            50

<210> SEQ ID NO 49
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 49
atccccgttg atagccaact tattctgcgt gatcgttttt taaaacgccg            50
```

```
<210> SEQ ID NO 50
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 50
aaattacaat ccttgctaga aaaaataatc ttgaacatcc gcgtttaggt          50

<210> SEQ ID NO 51
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 51
catccaagtg tagaatattg gtctgtttgc aaagttgagg cgttatttga          50

<210> SEQ ID NO 52
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 52
atacggcaca aagttggaca taactaagct agaaaaattt caacaaaagt          50

<210> SEQ ID NO 53
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 53
agccgctacg gctgtggcaa aagcctttga acaggaaaca ggcattaaag          50

<210> SEQ ID NO 54
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 54
atcgatagcg ccgaatgccg gcttggaccc ggtgaattat cagaacttcg cagtcacgaa          60
cgacggggtg attttcttct tcaacccggg ggagttgctg                              100

<210> SEQ ID NO 55
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 55
gggacgacct tgcatcggac ctgcaggcta taaacgattc gttcggcacg cttcgccacc          60
tggatccgcc ggtgcgtcgc tccggtggtc gtgaacagca                              100

<210> SEQ ID NO 56
<211> LENGTH: 100
```

```
<212> TYPE: DNA
<213> ORGANISM: Artificial Sequence
<220> FEATURE:
<223> OTHER INFORMATION: synthetically generated oligonucleotide

<400> SEQUENCE: 56
agcgccaccc gcggtccctc ttccccgagt tttctgagct gttcgcggcc ttcccgtcat     60
tcgccggact ccggcccacc ttcgacaccc ggttgatgcg                          100

<210> SEQ ID NO 57
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 57
acctggcgcg gtattccgct gatcccgtcg gacaaggtgc cggtggagga cggcaagacg     60
aagttcatcc tggtccgcac cggcgaggaa cgtcagggcg                          100

<210> SEQ ID NO 58
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 58
cggcgcccag agtgtctacg gcgtggtccc catgtgcgcg gtgatatcgg cgctcttcgg     60
ctccctcggc aactcggtgg gcatcaccat ggaccgccag                          100

<210> SEQ ID NO 59
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 59
atcgaccccg gattgccctc ggcgcgaatc gatttcatgc tcgccgacgc cgtgcccgtc     60
gtcacggtca ccaccgccga actgcgcgct tcggccggcg                          100

<210> SEQ ID NO 60
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 60
gtcgacgccg gagaattgat cgcccacgca tcgaattcgc tggcgcgcta caagcttccc     60
aaggcgatcg tgttccgtcc ggtgatcgag cgcagcccgt                          100

<210> SEQ ID NO 61
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 61
gtcaaagaac aaaagctgcg accaaagatt gacgatcacg attacgagac caaaaagggt     60
```
cacgtcgtcc gcttcttgga ggcgggatcg aaggtcaagg                          100

<210> SEQ ID NO 62
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 62
gaacaaaaag agtatctcgt cttgaaagtt gcgcagggcg acctgacagt acgagttccc    60
gctgaaaacg ccgaatacgt cggtgttcgc gatgtcgtcg                         100

<210> SEQ ID NO 63
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 63
ggtacaaaag gatagtgcca agcccttgga taaatttgga aatatctatg attatcacta    60
tgagcatgaa acacatgccc ctctctcacc tcgtattaga                         100

<210> SEQ ID NO 64
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 64
agagttgaaa ctgatatatc ggaattaggt ttaattgaat atgaaataga agaaaatgat    60
acaaacccta attataatga aaggacaata actatatctc                         100

<210> SEQ ID NO 65
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 65
aatatgacag ataacataac gctaaaaaca ccggtaatat catctcctat ggatacagta    60
acgggacata agatgtcaat agctttagct ttgagcggtg                         100

<210> SEQ ID NO 66
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 66
acatatacaa atagatgagg tggtaaaacc tgacacaaag aaggttataa aaaatgaagg    60
aatgccttac tcaagagatc caagtattag aggaaatttg                         100

<210> SEQ ID NO 67
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 67
acagggaaat gataaacata tagatagtga acataatgga ataaataaaa tgtacaaaga    60
aacaatacat aaaacactaa catctgatgt atcaacagaa                         100

<210> SEQ ID NO 68
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 68
cccaatacct acatgtggag cttctagggt tatggagaaa tgtcaaaaga tgtataaggt    60
ggttataaaa ccgaaggaga aggacgataa agtggataat                         100

<210> SEQ ID NO 69
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 69
cgcttagcta attcaattgg actaattgat gcaggttata gaggagaaat tattgccgcc    60
ttggataata ctagtgacca agagtatcac attaaaaaaa                         100

<210> SEQ ID NO 70
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 70
gggacgaagg ggatttcgac aacaatttag ttcctcacca attagaaaat atgattaaaa    60
tagccttagg agcatgtgca aaattagcaa ccaaatatgc                         100

<210> SEQ ID NO 71
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 71
attatcttac ctgtgaatat aaaaaatgct atggaaaaac aagctgaagc agaaagaaga    60
aaaagagctg aaattttaca aagtgaagga gaaagagaaa                         100

<210> SEQ ID NO 72
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 72
tactttatcc cgtgatggta agaatgatat tgaagaagaa gaagaagaag atgaggaaga    60
tgaaaaaaat ataaacaact cccaagatac cacattaagt                         100

<210> SEQ ID NO 73

```
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 73
tgaaggacca aaaggaaatg aacaaaaaaa acgtgatgac gatagtttga gtaaaataag      60
tgtatcacca gaaaattcaa gacctgaaac tgatgctaaa                          100

<210> SEQ ID NO 74
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 74
gaggtgctcc tcaaaatgga gctgcagaag ataaaaagac agaatattta ctagaacaaa      60
taaaaattcc atcatgggat agaaataaca tccccgatga                          100

<210> SEQ ID NO 75
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 75
atacaccact gctgttcccc ttattgttgc aataaaccca tacaaggatt taggaaacac      60
aactaatgaa tggattcgta gatatcgtga tacagctgat                          100

<210> SEQ ID NO 76
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 76
agaaccaact gttgctgaag aacacgtaga agaaccagct agtgatgttc aacaaacttc      60
agaagcagct ccaacaattg aaatccccga tacattatat                          100

<210> SEQ ID NO 77
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 77
actattaaag ctatggaaat tatatgggaa gctaccatga acaatgaaag gagaaaatat      60
gctgccacta aacgtagcat gctcagatat tatgatgatt                          100

<210> SEQ ID NO 78
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 78 ataccaga aagtagtagt acatatacaa atacaaggtt agcagcaaat aacagtacaa        60
```
ctacaagcac tacaaaagta acagataata ataaaacaaa                               100

<210> SEQ ID NO 79
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 79
attcaaacca cttatcgtag atgatgaact acttgaatac aaccaaaagg ttcataacat          60
aggaagaaat ggagaagaca ttttaactgc tatgcaaaca                               100

<210> SEQ ID NO 80
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 80
ctcaccgtgc ccagtgagcg aggactgcag cgtagacgct ttgtccaaaa tgcccttaat          60
gggaatgggg atccaaataa tatggacaga gcagttaaac                               100

<210> SEQ ID NO 81
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 81
atcgaaagct taagagggag ataacattcc atggggccaa agaaatagca ctcagttatt          60
ctgctggtgc acttgccagt tgtatgggac tcatatacaa                               100

<210> SEQ ID NO 82
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 82
gcaggcaatg agagccattg ggactcatcc tagctctagc actggtctga aaaatgatct          60
ccttgaaaat ttgcaggcct atcagaaacg aatgggggtg                               100

<210> SEQ ID NO 83
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 83
gctgacaaaa tgaccatcgt cagcatccac agcattctgc tgttcctctc gatattcttc          60
cctcatagac tctggtactc cttccgtaga aggccctctt                               100

<210> SEQ ID NO 84
<211> LENGTH: 100
<212> TYPE: DNA
<213> ORGANISM: Artificial Sequence
<220> FEATURE:

<223> OTHER INFORMATION: synthetically generated oligonucleotide

<400> SEQUENCE: 84

```
ggttgttgtt accatttgcc tatgagactt atgctgggag tcggcaatct gttcacaggt    60
tgcgcatata aggccaaatg ctgattcggt ggtcacagcc                         100
```

<210> SEQ ID NO 85
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 85

```
acacaaatcc taaaatcccc ttagtcagag gtgacaggat cggtcttgtc tttagccatt    60
ccatgagagc ctcaagatcg gtattctttc cagcaaagac                         100
```

<210> SEQ ID NO 86
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 86

```
aaacatatag tatgggcaag cagggagcta gaacgattcg cagttaatcc tggcctgtta    60
gaaacatcag aaggctgtag acaaatactg ggacagctac                         100
```

<210> SEQ ID NO 87
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 87

```
cagctgacac aggacacagc aatcaggtca gccaaaatta ccctatagtg cagaacatcc    60
aggggcaaat ggtacatcag gccatatcac ctagaacttt                         100
```

<210> SEQ ID NO 88
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 88

```
atcagaagga gccaccccac aagatttaaa caccatgcta acacagtgg ggggacatca     60
agcagccatg caaatgttaa aagagaccat caatgaggaa                         100
```

<210> SEQ ID NO 89
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 89

```
tagagactat gtagaccggt tctataaaac tctaagagcc gagcaagctt cacaggaggt    60
aaaaaattgg atgacagaaa ccttgttggt ccaaaatgcg                         100
```

<210> SEQ ID NO 90
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 90
gagacagcga cgaagagctc atcagaacag tcagactcat caagcttctc tatcaaagca    60
acccacctcc caaccccgag gggacccgac aggcccgaag                          100

<210> SEQ ID NO 91
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 91
cgacaggccc gaaggaatag aagaagaagg tggagagaga gacagagaca gatccattcg    60
attagtgaac ggatccttgg cacttatctg ggacgatctg                          100

<210> SEQ ID NO 92
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 92
cttatctggg acgatctgcg gagcctgtgc ctcttcagct accaccgctt gagagactta    60
ctcttgattg taacgaggat tgtggaactt ctgggacgca                          100

<210> SEQ ID NO 93
<211> LENGTH: 83
<212> TYPE: DNA
<213> ORGANISM: Artificial Sequence
<220> FEATURE:
<223> OTHER INFORMATION: synthetically generated oligonucleotide

<400> SEQUENCE: 93
gaacttctgg gacgcagggg gtgggaagcc ctcaaatatt ggtggaatct cctacagtat    60
tggagtcagg aactaaagaa tag                                            83

<210> SEQ ID NO 94
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 94
tggcgcaccc aacgcaacgt atgcggccca tgtgacgtac taccggctca cccgcgcctg    60
ccgtcagccc atcctccttc ggcagtatgg agggtgtcgc                          100

<210> SEQ ID NO 95
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 95
ctgctggtgc cgatctggga ccgcgccgcg gagacattcg agtaccagat cgaactcggc    60
ggcgagctgc acgtgggtct gttgtgggta gaggtgggcg                         100

<210> SEQ ID NO 96
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 96
cctaccacgc gtcgcttttg ctccccagag cctgctggtg gggattacgg gccgcacgtt    60
tattcggatg gcacgaccca cggaagacgg ggtcctgccg                         100

<210> SEQ ID NO 97
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 97
cccctgttct ggttcctaac ggcctcccct gctctagata tcctctttat catcagcacc    60
accatccaca cggcggcgtt cgtttgtctg gtcgccttgg                         100

<210> SEQ ID NO 98
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 98
gctaagcgaa ttactaaaaa ccgctgaagt gccgaaaggg tccttctatc actactttcg    60
ctctaaagaa gcgtttggcg ttgccatgct tgagcgtcat                         100

<210> SEQ ID NO 99
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 99
gtcggctggt tgaccttcct ttcggcagct attcctccag tgggtggcgt gatcatcgcc    60
gactatctga tgaaccgtcg ccgctatgag cactttgcga                         100

<210> SEQ ID NO 100
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 100
caaatccggt gatgctctac tctatcggta aagattccag cgtcatgctg catctggcgc    60
gcaaggcgtt ttatccaggt acgctgcctt tcccgttgct                         100

<210> SEQ ID NO 101
<211> LENGTH: 100
<212> TYPE: DNA
<213> ORGANISM: Artificial Sequence

```
<220> FEATURE:
<223> OTHER INFORMATION: synthetically generated oligonucleotide

<400> SEQUENCE: 101
tggattagat cagaaagcta ttcatcagcg gaaggggctg aaaaagaatc agaagatcct      60
ggatcatatg ggttcaacag aactggcggc taatctcttt                          100

<210> SEQ ID NO 102
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 102
gaataccgcc acgacacggg agttttcgac cggccttaac gccagctttg acctcgattt      60
tttcggtcgc ttaaagaaca tgagcgaagc cgagcgacaa                          100

<210> SEQ ID NO 103
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 103
gaaggcagta acgtcaatgc cgttgcggca atgagcgaca tgattgccag cgcgcggcgt      60
tttgaaatgc agatgaaggt gatcagcagc gtcgatgata                          100

<210> SEQ ID NO 104
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 104
caaatccggt gatgctctac tctatcggta aagattccag cgtcatgctg catctggcgc      60
gcaaggcgtt ttatccaggt acgctgcctt tcccgttgct                          100

<210> SEQ ID NO 105
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 105
ttcggtaaaa ccgcgacctt tatgccaaaa ccgatgttcg gtgataacgg ctccggtatg      60
cactgccaca tgtctctgtc taaaaacggc gttaacctgt                          100

<210> SEQ ID NO 106
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 106
ttgtggatgt gcagtcgaaa atctatctgc gcgataaagt cggcaaactg ggggttgcac      60
cgttaaccag tatgttcctg tttgggccga accaaccgtc                          100
```

<210> SEQ ID NO 107
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 107
cgacagtgtt ggtgagcggc tgggtcgtgt tgggctggat ggaagatgcg caacgcctgc      60
cgctctcaaa gctggtgttg accggtgaac gccattacac                          100

<210> SEQ ID NO 108
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 108
gctaagcgaa ttactaaaaa ccgctgaagt gccgaaaggg tccttctatc actactttcg      60
ctctaaagaa gcgtttggcg ttgccatgct tgagcgtcat                          100

<210> SEQ ID NO 109
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 109
aacacgctgc tgatcttcat caaccagatc cgtatgaaaa ttggtgtgat gttcggtaac      60
ccggaaacca ctaccggtgg taacgcgctg aaattctacg                          100

<210> SEQ ID NO 110
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 110
tggattagat cagaaagcta ttcatcagcg gaaggggctg aaaaagaatc agaagatcct      60
ggatcatatg ggttcaacag aactggcggc taatctcttt                          100

<210> SEQ ID NO 111
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 111
gatgaagaat cttctcaggt acatgcacaa ggtctggtga ttcgcgacct gccgctgatt      60
gccagcaact tccgtaatac cgaagacctc tcttcttacc                          100

<210> SEQ ID NO 112
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 112
caatcgccta cggtgctgat gaagttgacg ttgtgttccc gtaccgcgcg ctgatggcgg    60
gtaacgagca ggttggtttt gacctggtga aagcctgtaa                        100

<210> SEQ ID NO 113
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 113
gaaggcagta acgtcaatgc cgttgcggca atgagcgaca tgattgccag cgcgcggcgt    60
tttgaaatgc agatgaaggt gatcagcagc gtcgatgata                        100

<210> SEQ ID NO 114
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 114
cccgatctct tcaacctaaa ctatctgggg agaggaaaat ggttcgattt gtttcgctgc    60
ttcaggagta acactttagg ggcaaaaatg caggcgctga                        100

<210> SEQ ID NO 115
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 115
aacacgctgc tgatcttcat caaccagatc cgtatgaaaa ttggtgtgat gttcggtaac    60
ccggaaacca ctaccggtgg taacgcgctg aaattctacg                        100

<210> SEQ ID NO 116
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 116
gctgcctgct atctccgaca tgagcattgg tcatgcgatg gaattcttca acaatctcaa    60
actcgcaggt cagcgggcga agattgcaga aaaaatcctt                        100

<210> SEQ ID NO 117
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 117
tttccctcta ggttagaaac atggggattg ccgttgtctg aagctaaaga gcgaggtaag    60
tgggtattag catcagattt cccatttact agagaaactc                        100

<210> SEQ ID NO 118
<211> LENGTH: 100
<212> TYPE: DNA

<213> ORGANISM: Artificial Sequence
<220> FEATURE:
<223> OTHER INFORMATION: synthetically generated oligonucleotide

<400> SEQUENCE: 118
aacggaaccg agcgtcgcct ccgcgatgtt tgaataccgt tttggtggca atggcgaact    60
ttccggtcat aatctcggaa acttgatgtt aaaggcgctg                        100

<210> SEQ ID NO 119
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 119
aacgctatca cgatatttcg cgcctggtga tgaacgaccc gagcgagaaa aatctcaacg    60
aactggcgaa ggttcaggaa cagctggatc accacaacct                        100

<210> SEQ ID NO 120
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 120
tgccatccgt gacgcactgg tacgtcagtt gtataacccg gttcagtgga cgaagtctgt    60
tgagtacatg gcagcgcaag gcgtagaaca tctctatgaa                        100

<210> SEQ ID NO 121
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 121
tgccatccgt gacgcactgg tacgtcagtt gtataacccg gttcagtgga cgaagtctgt    60
tgagtacatg gcagcgcaag gcgtagaaca tctctatgaa                        100

<210> SEQ ID NO 122
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 122
aaacctggca tcatgattaa agtgcttagc gaaatcacct ccagcctgaa taaagactct    60
ctggtcgttt ctattgctgc aggtgtcacg ctcgaccagc                        100

<210> SEQ ID NO 123
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 123
actaacgaat acggcttcct tgagactccg tatcgtaaag tgaccgacgg tgttgtaact    60
gacgaaattc actacctgtc tgctatcgaa gaaggcaact                        100

<210> SEQ ID NO 124
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 124
tgtggttctt cctgggcggt ttcggcgcac accgcttcta cctggggaaa accggcacgg     60
cggttaccca actgatcatc acgctgatcg gttgtttcac                          100

<210> SEQ ID NO 125
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 125
ccacaaacaa tactcttatc aagaattccc caacccctct agaaaagcag aaagccatct     60
acaatggtga gctacttgtg gatgagatag ccagtctaca                          100

<210> SEQ ID NO 126
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 126
gaacacggcg gaggcggtgt tccgtcttgg ccggctgacg gcttcctata tccatttcta     60
cctgccttcc aacccgcagg ccgccgctgc gttgctggcg                          100

<210> SEQ ID NO 127
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 127
cccggccatg ctgaatgccg cgaacgaggt ggccgtggcc gcatttctcg agcggcacat     60
ccgcttcagc gacatcgcgg ttatcatcga ggacgtgctg                          100

<210> SEQ ID NO 128
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 128
tctcgaccag cggctttcgt cgcgacttcg agcaggcgcg ttcgatgcag gtgttcggcg     60
acagcttccc ggcgcgggta ttcgccatga gcgagcggcc                          100

<210> SEQ ID NO 129
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 129
gcagcaaggt ctggctgctg gcggaaaacc ctgagttcgc tccgatcgaa gtcgatctga    60
aggagcagga actgatcatc gaaggcttga gcgtcggcgt                         100

<210> SEQ ID NO 130
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 130
cggggcagga gcttaacgcc ctgcatgcgc agaacgtcgg catcggcgcg gtggtcggct    60
tcgtcggcta cgtgcgcgac ttcaacgacg gtcgcgaggt                         100

<210> SEQ ID NO 131
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 131
ggtgaagaac aaggtttccc cgccgttccg ccaggccgag ttccagatcc tctacggtaa    60
gggcatctac cgtaccggcg agatcatcga tctgggcgtg                         100

<210> SEQ ID NO 132
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 132
cttcggcgcc gtcgagatca ccgtgcacaa cggccaggtg gtgcagatcg agcgcaagga    60
aaaattccgt ctgcagcaac cggccgtcaa gcaggcctga                         100

<210> SEQ ID NO 133
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 133
gagcactatc tcaatcgcga cagcttcccc gagcagaagt accgccactg cggttgcagc    60
cgcaacacct tttatctgcg cctgcatgtg gcgcaccagg                         100

<210> SEQ ID NO 134
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 134
cctgctgaag ccgcgccacg tggagatcca ggtattcgcc gaccgccatg ccactgcct    60 gtacctcaac gaacgcgact gttcgatcca gcgccgccac                         100

<210> SEQ ID NO 135
<211> LENGTH: 100

```
<212> TYPE: DNA
<213> ORGANISM: Artificial Sequence
<220> FEATURE:
<223> OTHER INFORMATION: synthetically generated oligonucleotide

<400> SEQUENCE: 135
ttcaacgatc tgttcgagtc ggccctgcgt aatgaggccg ggagtaccta cccgccctac      60
aacgtcgaaa agcacggtga cgacgagtat cgcatcgtta                           100

<210> SEQ ID NO 136
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 136
acggccgcct gagcctgccg ccattgcgcg aacgtccggg agacatcctg ccgctggcgg      60
aatacttcat cggcgtctat gcccagcgcc tggacctgcc                           100

<210> SEQ ID NO 137
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 137
acgctgcaga ccatctggtt ctacaacacc acccagtgct acggcgacgc ctcgaccatc      60
aaccagagcg tcaccgtgct gaccggcggg gcgaatatcc                           100

<210> SEQ ID NO 138
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 138
cctggagatg tccgatccca acgacgaggc gatcaagccg atgcgcgaag ggatggaact      60
gaccctgaag atgttcgacg acaccctgcg ccgctaccag                           100

<210> SEQ ID NO 139
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 139
tatgtcggac gcgacgtcga atcgatcatc cgcgatctcg ccgacgccgc ggtgaagatg      60
ctccgcgaac aggagatcca gaaggtcaag tatcgcgccg                           100

<210> SEQ ID NO 140
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 140
ggtggcgttg ccagtcagcg tgccgtcgca ttgcgaactg atgcgtccgg ccgccgagca      60
```

```
gttcgccgcc tcggtcgaaa gcctgcagtg gcaggcgccg                          100
```

<210> SEQ ID NO 141
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 141

```
cctgtggctg gacgacgaag cgcagatcga cgcggtgacc gcagtgtcgg gcagcggccc    60
ggcgtatttc ttcctgctga tgcaggccat gaccgacgcc                         100
```

<210> SEQ ID NO 142
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 142

```
accttcgccg taccgctgcg cgtgaaagtt cgcctgatca tcttcgaccg cgagtcgtcg    60
aacaaggcga tcaaggacat caaggaacaa gaagtctaca                         100
```

<210> SEQ ID NO 143
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 143

```
aacatgatga tggctattaa tgttaaagat gtacaagata aaggaatggc tagctacaat    60
gccaaaatct caggtaaagt gtatgatgag ctatatgaga                         100
```

<210> SEQ ID NO 144
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 144

```
agaatataaa ggctataaag atgatgcagt tattggtaaa aagggactcg aaaaacttta    60
cgataaaaag ctccaacatg aagatggcta tcgtgtcaca                         100
```

<210> SEQ ID NO 145
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 145

```
tgataggccg gtggcagcta cgtttaccta tcctgttttt gttaagccgg cgcgttcagg    60
ctcatccttc ggtgtgaaaa aagtcaatag cgcggacgaa                         100
```

<210> SEQ ID NO 146
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 146
ggagcgagga cggatacagg aaacggcaaa aaaaatatat aaagcgctcg gctgtagagg    60
tctagcccgt gtggatatgt ttttacaaga taacggccgc                         100

<210> SEQ ID NO 147
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 147
gaggacgctt acctaccctg tctttgtgaa gccggcacgg tcaggttcgt cctttggcgt    60
aaccaaagta aacagtacgg aagaactaaa cgctgcgata                         100

<210> SEQ ID NO 148
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 148
accaggctta cgagaagcgg gattctggcg gttcgtcgcc gacccgtacg atccgagcga    60
gtctcaggcg atcgagttgc tattggcgca ttcggccggt                         100

<210> SEQ ID NO 149
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 149
ccgcccaatt cggggtcaag cgcggtctgt tgggcaagtt gatgccggtc aaacgcacga    60
cctttgtcat cgacaccgac cgtaaggtgc tcgacgtgat                         100

<210> SEQ ID NO 150
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 150
gtcgattacc tggcctgaat tcgggcgtca gcatccattt gccccggcat ctgataccgc    60
tgggctgcgt caacttgttg ccgacctaca gagttggctg                         100

<210> SEQ ID NO 151
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 151
cgttgatcct gctgcaccaa gacaagatca gctcgcttcc cgatctgttg ccattgctgg    60
aaaaggttgc aggaacgggt aagccactac tgatcgtggc                         100

<210> SEQ ID NO 152

```
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 152
cagctggccg gcttggcgcg atatccgcag ccgatggccc cggccgccgc cgccgaacac    60
gccgggatgg cgttgcccgc ccgcgatcag atcgtgcggc                          100

<210> SEQ ID NO 153
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 153
ggtgcgcctg gattgtgacg gcgacgccgt attgttgacg gttgaccagg tcggcggtgc    60
ctgccatacc ggcgatcaca gttgcttcga tgccgcggtg                          100

<210> SEQ ID NO 154
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 154
ccgcgcaggg gcgcaccca ctccccttct acgtgtggcg ggcgtttgcg cgctattctc    60
cggtgcttcc cgctggccgt ctggtgaact tcggcaccgt                          100

<210> SEQ ID NO 155
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 155
ggtggattgt cgagcagctt cgttcgaccg gccctgccaa tacgacactg gtggtcatcg    60
tcaccaagat tgacaaggtg ccgaaagaaa aagtggtcgc                          100

<210> SEQ ID NO 156
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 156
cggcatccac gcactcgaag acgagttcgt caccaagtgg gatctagcgg tcaagatcgg    60
cggtcacctc aaggatccgg tcgacagcca catgggccga                          100

<210> SEQ ID NO 157
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 157
cggcgagtgc accgttccgc gggtcacgct ggtcacccga aagacctacg gcggggcata    60
```
cattgcgatg aactcccggt cgttgaacgc gaccaaggtg                        100

<210> SEQ ID NO 158
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 158
gtgtgtcctc gcagctggtg tcccggtttt cgccacgggt gttgaccatc ggcggcggat    60
atctgctatt cggcgccatg ctgtacggct cattttcat                         100

<210> SEQ ID NO 159
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 159
gcaggccgag gccgtggatg tgcatacgct cgctcggaat ggaatgccgg aggcgctgga    60
ttacctgcat cgacgtcaag cccggcgaat caccgattca                        100

<210> SEQ ID NO 160
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 160
gagagagtgg gatggcgtac cacaacccgt tcatcgtgaa tggaaagatc aggttcccag    60
ccaacaccaa cctggttcgt cacgtcgaaa agtgggcgaa                        100

<210> SEQ ID NO 161
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 161
cggcatccac gcactcgaag acgagttcgt caccaagtgg gatctagcgg tcaagatcgg    60
cggtcacctc aaggatccgg tcgacagcca catgggccga                        100

<210> SEQ ID NO 162
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 162
cggcgagtgc accgttccgc gggtcacgct ggtcacccga aagacctacg gcggggcata    60
cattgcgatg aactcccggt cgttgaacgc gaccaaggtg                        100

<210> SEQ ID NO 163
<211> LENGTH: 100
<212> TYPE: DNA
<213> ORGANISM: Artificial Sequence
<220> FEATURE:

<223> OTHER INFORMATION: synthetically generated oligonucleotide

<400> SEQUENCE: 163

```
caagtccagc aagcggcgcc cggctccgga aaagccggtc aagacgcgta aatgcgtgtt    60
ctgcgcgaag aaggaccaag cgatcgacta caaggacacc                         100
```

<210> SEQ ID NO 164
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 164

```
cggccgcccg attcgagtct gccaccgcat cagcgggcac ggtgtcgctg cggctacccg    60
tccgtgcacc attcgccttc gagggtgttt tcggccatct                         100
```

<210> SEQ ID NO 165
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 165

```
tcgtcaacgg tcgacggatc cagagcaaac gtcaagtgtt cgaggtccgg atctcgggta    60
tggataacgt cacggcattc gcggagtcag ttcccatgtg                         100
```

<210> SEQ ID NO 166
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 166

```
aacaacccgt atgcacagtt tcaggacgaa tacaccctgg acgacatctt ggcctcaaag    60
atgatttccg acccgctgac caaattgcag tgctctccca                         100
```

<210> SEQ ID NO 167
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 167

```
ccgctaccgc agtggtaccc accgacagca cattgttggt cgagcggttt cgtgacgagc    60
tgggcgattg gcgggtgatc ttgcattcgc cgtatgggct                         100
```

<210> SEQ ID NO 168
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 168

```
tcgctgcggc tctacgattc gtcgtatcat gccgaactct tttggtggac agggggctttt    60 gagacttctg agggcatacc gcacagttca ttggtatcgg                         100
```

-continued

<210> SEQ ID NO 169
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 169
cggcacaccg aagtgatgcc ggtgactcga ttcaccaccg cgcacagccg cgaccgtggc      60
gagagtgtct gggctcccga gtatcagctt gtcgacgagc                          100

<210> SEQ ID NO 170
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 170
cggtttcagt cggccctaga cgggacgctc aatcagatga acaacggatc cttccgcgcc      60
accgacgaag ccgagaccgt cgaagtgacg atcaatgggc                          100

<210> SEQ ID NO 171
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 171
aagaggtgct ctacgagctg tctccgatcg aggacttctc cgggtcgatg tcgttgtcgt      60
tctctgaccc tcgtttcgac gatgtcaagg cacccgtcga                          100

<210> SEQ ID NO 172
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 172
cgccgaatgc cggcttggac ccggtgaatt atcagaactt cgcagtcacg aacgacgggg      60
tgattttctt cttcaacccg ggggagttgc tgcccgaagc                          100

<210> SEQ ID NO 173
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 173
agcgaccaaa gcaagcacgg cgaccgatga gccggtaaaa cgcaccgcca ccaagtcgcc      60
cgcggcttcc gcgtccgggg ccaagaccgg cgccaagcga                          100

<210> SEQ ID NO 174
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 174
aagcactcta cgaaaatgca ttgaatttag tgttgccaaa ggcttacgaa        50

<210> SEQ ID NO 175
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 175
aaattgtttg tgatcacttg aagcttgaga cacctgctgc tgatatgaca        50

<210> SEQ ID NO 176
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 176
aactatctta tgtaatagtg aaaaggatcc tatcaaagaa aaagaatacc        50

<210> SEQ ID NO 177
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 177
aaatagtaaa gtaactgtca aggttattgg agatagctct tttggtcata        50

<210> SEQ ID NO 178
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 178
aagggaattt ttctaaagca gcccaaggtt ttgttcgcgg aaaaggttta        50

<210> SEQ ID NO 179
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 179
aagcgtcctc aagaaatatc acaacaacaa gcagtttcta gcgtaggaca        50

<210> SEQ ID NO 180
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 180
aaggctattg acaatgctca tatacgtttta aagaaatatg tggataccgg       50

<210> SEQ ID NO 181
<211> LENGTH: 50
<212> TYPE: DNA
<213> ORGANISM: Artificial Sequence

```
<220> FEATURE:
<223> OTHER INFORMATION: synthetically generated oligonucleotide

<400> SEQUENCE: 181
aagttaaaca agaagtaaat caattaaata gtaaaatcaa cgataaacag              50

<210> SEQ ID NO 182
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 182
aaccaaatcg agctgtcgcc atatctgcag aaccgcaaag tggtggaatt              50

<210> SEQ ID NO 183
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 183
aaccctgttg attcacggcg gttttttgccc aaggcatacg gtaaaggtac             50

<210> SEQ ID NO 184
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 184
aaccgctgat tgacggcggg aaaatcaaag tggtgggcga tcagtgggtc              50

<210> SEQ ID NO 185
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 185
aaactggaag ccgaaagcga agtgatttta caggctaacg aacaggacat              50

<210> SEQ ID NO 186
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 186
aaagcattgc tctgcaaacg gtcactcaac cgtcaactgt agttgccact              50

<210> SEQ ID NO 187
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 187
aaaaatggaa cgacccggcg atcaccaagc tcaacccagg cgttaagctg              50
```

<210> SEQ ID NO 188
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 188
aacgtgacat ggtgttctct gccaacggca ccaacaccct gaaagccaac           50

<210> SEQ ID NO 189
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 189
aacctgcgtc aaccgttgcg cattattctg gatagccaaa atcgcgtcac           50

<210> SEQ ID NO 190
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 190
aattgttctg actagtgatc gtagtcctaa acacttagag ggccttgaag           50

<210> SEQ ID NO 191
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 191
aaggaattga aaaagctcaa agccttacta agaaagaaga agctgctgag           50

<210> SEQ ID NO 192
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 192
actggtgctg gtggtggtgt cattttcaca ccatcaatct caagccatga           50

<210> SEQ ID NO 193
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 193
aagatggttt attcaatttt ctggccatta aacgaagaat ttgaaaaatc           50

<210> SEQ ID NO 194
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 194
agcgatgacc tataccacct atgatagtgg taatagtggt caacaaacag            50

<210> SEQ ID NO 195
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 195
aacatgattt acgatacaga agccaatctg acagttgatc atgatttgag            50

<210> SEQ ID NO 196
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 196
acaactccgt agtatcttca caggtcaagt gaccaactgg aaagaagtcg            50

<210> SEQ ID NO 197
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 197
aaagctgcta atctgccaa gactgctgct gctggtggta agaaggaagc             50

<210> SEQ ID NO 198
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 198
aaaatggtac tacatgtgca tcatacttta ctactattga tccggaaaca            50

<210> SEQ ID NO 199
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 199
acatagtcca ataacaaata aacttgagga tcatgatgat gaaattggat            50

<210> SEQ ID NO 200
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 200
aaaacaaaca atcaactggt gatgaagtca agagcaagag aaaatcggca            50

<210> SEQ ID NO 201

<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 201
aatgatttat gatacgttta ataaattaca agaatctagt gatcagtcga            50

<210> SEQ ID NO 202
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 202
acacaaaact gaagacaaag ggactagcac ttcatccaag gaagaaccat            50

<210> SEQ ID NO 203
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 203
actggtgtag ttgaccttat cgaaatgaag gcaattatct gggatgaagc            50

<210> SEQ ID NO 204
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 204
aattgtgaat gaagaaacgc gtaagacttt tgaaattcgt gccaaagtcg            50

<210> SEQ ID NO 205
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 205
aaaaagtatt tcggtacgac aagcaaacgt tatatctacc tttctggttg            50

<210> SEQ ID NO 206
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 206
acagaagtaa ttgcaggtga aggacaaatt ttaacagctg gtggtattga            50

<210> SEQ ID NO 207
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 207
aaattgatga gctgaatatc ttgcaggcaa cttttttggc tatgcaacgt        50

<210> SEQ ID NO 208
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 208
aaaactccac ccgtactcgt actactttg aagcagcagc aaaacgtttg         50

<210> SEQ ID NO 209
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 209
accgcaagtg gtgtttgaat taggcgttcc agtattgggt atttgctatg        50

<210> SEQ ID NO 210
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 210
agttgcaggg tatggggcta gatgctaaaa taaacgacat tttagctaat        50

<210> SEQ ID NO 211
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 211
aaaattgaag cgaaatcaat cgcccttgaa aatggtgcga ttttggctcg        50

<210> SEQ ID NO 212
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 212
aaaaagtaaa gatattatta atgtcgatat tacactagaa aaaaatggtt        50

<210> SEQ ID NO 213
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 213
aaaacttatg agcacgagaa gtttattaca gctgaaatta ataaactagc        50

<210> SEQ ID NO 214
<211> LENGTH: 50
<212> TYPE: DNA

<213> ORGANISM: Artificial Sequence
<220> FEATURE:
<223> OTHER INFORMATION: synthetically generated oligonucleotide

<400> SEQUENCE: 214
aaaacaggtg aattaggtcc tttatatgat ctgtttaacc ttgcgcaaaa         50

<210> SEQ ID NO 215
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 215
aaaacgccct gtgagttctg atgatgttga agctgctatt aatcatatca         50

<210> SEQ ID NO 216
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 216
aaaggtattg aggcggctat tccatttgcc ccattacata acccagctca         50

<210> SEQ ID NO 217
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 217
aaaaaagatg ttctgatgga agaaattgtt gctagatatc acgaaaatac         50

<210> SEQ ID NO 218
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 218
aaatgggcaa ttggtgcatc aggtactact aactttggtt tagctaccga         50

<210> SEQ ID NO 219
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 219
atcgtcggca accagaacgt cgccgggcag ttgtatgacg gcttgaccgt         50

<210> SEQ ID NO 220
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 220
atcgacatcc acgcgcgtga gatcctgacc ctgcgttcgc gcctgaacga         50

<210> SEQ ID NO 221
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 221
caagatctac cagcgtccgt tcggtggcat gaccaccaag tacggcgaag          50

<210> SEQ ID NO 222
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 222
aagcgcctga tcggccgcaa gttcaccgac gccgaagtgc agaaggacat          50

<210> SEQ ID NO 223
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 223
atgctcgaat ttccacgctg gaagtacgtc gtcatcctga tcgtactggc          50

<210> SEQ ID NO 224
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 224
cgagcgccgg cataagcagt tgaaagacaa gggggtttct gttaactttg          50

<210> SEQ ID NO 225
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 225
cctgcccgac ccgatcccgg gcaagggcga gatgctctgc caggtctcca          50

<210> SEQ ID NO 226
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 226
cgccgaaggc atggccggac agccgccgca cagcctgccc agcggcacca          50

<210> SEQ ID NO 227
<211> LENGTH: 100
<212> TYPE: DNA
<213> ORGANISM: Artificial Sequence
<220> FEATURE:

<223> OTHER INFORMATION: synthetically generated oligonucleotide

<400> SEQUENCE: 227

```
aatccggttg agccacggta tcttccgcat ccatcaggaa aacgagccgg aaaaaggctc    60
agagaatgcg atgattatcg ttccagcaga cattccggtc                         100
```

<210> SEQ ID NO 228
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 228

```
ccgctaccgc agtggtaccc accgacagca cattgttggt cgagcggttt cgtgacgagc    60
tgggcgattg gcgggtgatc ttgcattcgc cgtatgggct                         100
```

<210> SEQ ID NO 229
<211> LENGTH: 99
<212> TYPE: DNA
<213> ORGANISM: Artificial Sequence
<220> FEATURE:
<223> OTHER INFORMATION: synthetically generated oligonucleotide

<400> SEQUENCE: 229

```
ggccgcccga ttcgagtctg ccaccgcatc agcgggcacg gtgtcgctgc ggctacccgt    60
ccgtgcacca ttcgccttcg agggtgtttt cggccatct                          99
```

<210> SEQ ID NO 230
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 230

```
aacaacccgt atgcacagtt tcaggacgaa tacaccctgg acgacatctt ggcctcaaag    60
atgatttccg acccgctgac caaattgcag tgctctccca                        100
```

<210> SEQ ID NO 231
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 231

```
tcgtcaacgg tcgacggatc cagagcaaac gtcaagtgtt cgaggtccgg atctcgggta    60
tggataacgt cacggcattc gcggagtcag ttcccatgtg                        100
```

<210> SEQ ID NO 232
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 232

```
cagctggccg gcttggcgcg atatccgcag ccgatggccc cggccgccgc cgccgaacac    60
gccgggatgg cgttgcccgc ccgcgatcag atcgtgcggc                        100
```

<210> SEQ ID NO 233
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 233
ggtggattgt cgagcagctt cgttcgaccg gccctgccaa tacgacactg gtggtcatcg    60
tcaccaagat tgacaaggtg ccgaaagaaa aagtggtcgc                         100

<210> SEQ ID NO 234
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 234
ggtgcgcctg gattgtgacg gcgacgccgt attgttgacg gttgaccagg tcggcggtgc    60
ctgccatacc ggcgatcaca gttgcttcga tgccgcggtg                         100

<210> SEQ ID NO 235
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 235
ccgcgcagtg ttcaaagctc ggatatacgg tggcacccat ggaacagcgt gcggagttgg    60
tggttggccg ggcacttgtc gtcgtcgttg acgatcgcac                         100

<210> SEQ ID NO 236
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 236
gtgtgtcctc gcagctggtg tcccggtttt cgccacgggt gttgaccatc ggcggcggat    60
atctgctatt cggcgccatg ctgtacggct catttttcat                         100

<210> SEQ ID NO 237
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 237
cggcgagtgc accgttccgc gggtcacgct ggtcacccga agacctacg gcggggcata    60 cattgcgatg aactcccggt cgttgaacgc gaccaaggtg                         100

<210> SEQ ID NO 238
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 238

```
gcaggccgag gccgtggatg tgcatacgct cgctcggaat ggaatgccgg aggcgctgga    60
ttacctgcat cgacgtcaag cccggcgaat caccgattca                         100

<210> SEQ ID NO 239
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 239
gtcgattacc tggcctgaat tcgggcgtca gcatccattt gccccggcat ctgataccgc    60
tgggctgcgt caacttgttg ccgacctaca gagttggctg                         100

<210> SEQ ID NO 240
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 240
ccgcccaatt cggggtcaag cgcggtctgt tgggcaagtt gatgccggtc aaacgcacga    60
cctttgtcat cgacaccgac cgtaaggtgc tcgacgtgat                         100

<210> SEQ ID NO 241
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 241
acgccgttct acccgcggtc accgtatggc gccgccaagg tctattcgta ctgggcgacc    60
cgcaattatc gcgaagcgta cggattgttc gccgttaacg                         100

<210> SEQ ID NO 242
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 242
cgttgatcct gctgcaccaa gacaagatca gctcgcttcc cgatctgttg ccattgctgg    60
aaaaggttgc aggaacgggt aagccactac tgatcgtggc                         100

<210> SEQ ID NO 243
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 243
cgccgaatgc cggcttggac ccggtgaatt atcagaactt cgcagtcacg aacgacgggg    60
tgattttctt cttcaacccg ggggagttgc tgcccgaagc                         100

<210> SEQ ID NO 244
<211> LENGTH: 100
<212> TYPE: DNA
<213> ORGANISM: Artificial Sequence
```

```
<220> FEATURE:
<223> OTHER INFORMATION: synthetically generated oligonucleotide

<400> SEQUENCE: 244
aagaggtgct ctacgagctg tctccgatcg aggacttctc cgggtcgatg tcgttgtcgt    60
tctctgaccc tcgtttcgac gatgtcaagg cacccgtcga                         100

<210> SEQ ID NO 245
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 245
gaacaaaaag agtatctcgt cttgaaagtt gcgcagggcg acctgacagt acgagttccc    60
gctgaaaacg ccgaatacgt cggtgttcgc gatgtcgtcg                         100

<210> SEQ ID NO 246
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 246
agcgaccaaa gcaagcacgg cgaccgatga gccggtaaaa cgcaccgcca ccaagtcgcc    60
cgcggcttcc gcgtccgggg ccaagaccgg cgccaagcga                         100

<210> SEQ ID NO 247
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 247
cggcatccac gcactcgaag acgagttcgt caccaagtgg gatctagcgg tcaagatcgg    60
cggtcacctc aaggatccgg tcgacagcca catgggccga                         100

<210> SEQ ID NO 248
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 248
caagtccagc aagcggcgcc cggctccgga aaagccggtc aagacgcgta atgcgtgtt    60 ctgcgcgaag aaggaccaag cgatcgacta caaggacacc                         100

<210> SEQ ID NO 249
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 249
ccgcgcaggg gcgcaccccca ctccccttct acgtgtggcg ggcgtttgcg cgctattctc    60
cggtgcttcc cgctggccgt ctggtgaact tcggcaccgt                         100
```

```
<210> SEQ ID NO 250
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 250
gagagagtgg gatggcgtac cacaacccgt tcatcgtgaa tggaaagatc aggttcccag      60
ccaacaccaa cctggttcgt cacgtcgaaa agtgggcgaa                           100

<210> SEQ ID NO 251
<211> LENGTH: 100
<212> TYPE: DNA
<213> ORGANISM: Artificial Sequence
<220> FEATURE:
<223> OTHER INFORMATION: synthetically generated oligonucleotide

<400> SEQUENCE: 251
accaggctta cgagaagcgg gattctggcg gttcgtcgcc gacccgtacg atccgagcga      60
gtctcaggcg atcgagttgc tattggcgca ttcggccggt                           100
```